(12) United States Patent
Bolduc et al.

(10) Patent No.: US 9,023,065 B2
(45) Date of Patent: May 5, 2015

(54) DEVICES, SYSTEMS, AND METHODS FOR SUPPORTING TISSUE AND/OR STRUCTURES WITHIN A HOLLOW BODY ORGAN

(75) Inventors: Lee Bolduc, Sunnyvale, CA (US); Andrew L. Chiang, Fremont, CA (US); Philip R. Houle, Sunnyvale, CA (US); Gilbert S. Laroya, Santa Clara, CA (US)

(73) Assignee: Aptus Endosystems, Inc., Sunnyvale, CA (US)

(*) Notice: Subject to any disclaimer, the term of this patent is extended or adjusted under 35 U.S.C. 154(b) by 0 days.

(21) Appl. No.: 13/157,242

(22) Filed: Jun. 9, 2011

(65) Prior Publication Data

US 2011/0238088 A1 Sep. 29, 2011

Related U.S. Application Data

(63) Continuation of application No. 11/365,056, filed on Mar. 1, 2006, now abandoned, which is a continuation of application No. 10/808,216, filed on Mar. 24, 2004, now abandoned, which is a continuation-in-part of application No. 10/307,226, filed on Nov. 29, 2002, now Pat. No. 8,075,570, and a continuation-in-part of application No. 10/271,334, filed on Oct. 15, 2002, now Pat. No. 6,960,217.

(60) Provisional application No. 60/333,937, filed on Nov. 28, 2001.

(51) Int. Cl.
*A61B 17/10* (2006.01)
*A61B 17/00* (2006.01)
(Continued)

(52) U.S. Cl.
CPC ........ *A61B 17/00234* (2013.01); *A61B 17/0057* (2013.01); *A61B 17/0401* (2013.01); *A61B 17/0487* (2013.01); *A61B 17/064* (2013.01); *A61B 17/068* (2013.01); *A61B 17/12122* (2013.01); *A61B 17/12172* (2013.01); *A61B 2017/00243* (2013.01); *A61B 2017/00575* (2013.01); *A61B 2017/00592* (2013.01); *A61B 2017/00606* (2013.01); *A61B 2017/00783* (2013.01); *A61B 2017/0441* (2013.01);
(Continued)

(58) Field of Classification Search
USPC ........ 623/1.1, 1.11, 1.16, 3.1, 3.16, 2.11, 2.1; 606/151, 153, 192, 194, 195, 198, 139, 606/142; 600/16–18, 37
See application file for complete search history.

(56) References Cited

U.S. PATENT DOCUMENTS 2,033,039 A 3/1936 Limpert
3,499,222 A 3/1970 Linkow et al.
(Continued)

FOREIGN PATENT DOCUMENTS

AU 2002353807 B2 6/2003
AU 2004277897 B2 4/2005
(Continued)

OTHER PUBLICATIONS

Non Final Office Action mailed on Mar. 23, 2010, U.S. Appl. No. 11/365,056, filed Mar. 1, 2006, 8 pages.
(Continued)

*Primary Examiner* — Dianne Dornbusch
(74) *Attorney, Agent, or Firm* — Schwegman Lundberg & Woessner, P.A.

(57) ABSTRACT

Devices, systems and methods support tissue in a body organ for the purpose of restoring or maintaining native function of the organ. The devices, systems, and methods do not require invasive, open surgical approaches to be implemented, but, instead, lend themselves to catheter-based, intra-vascular and/or percutaneous techniques.

7 Claims, 30 Drawing Sheets

(51) Int. Cl.
*A61B 17/04* (2006.01)
*A61B 17/064* (2006.01)
*A61B 17/068* (2006.01)
*A61B 17/12* (2006.01)
*A61F 2/24* (2006.01)

(52) U.S. Cl.
CPC ... *A61B2017/0454* (2013.01); *A61B 2017/048* (2013.01); *A61B 2017/0488* (2013.01); *A61B 2017/0496* (2013.01); *A61B 2017/0646* (2013.01); *A61B 2017/0649* (2013.01); *A61F 2/2412* (2013.01); *A61F 2/2445* (2013.01); *A61F 2/2466* (2013.01); *A61F 2/2478* (2013.01); *A61F 2/2481* (2013.01); *A61F 2/2487* (2013.01); *A61F 2002/249* (2013.01)

(56) References Cited

U.S. PATENT DOCUMENTS

| | | |
|---|---|---|
| 3,686,740 A | 8/1972 | Shiley |
| 3,799,172 A | 3/1974 | Szpur |
| 4,140,126 A | 2/1979 | Choudhury |
| 4,255,820 A | 3/1981 | Rothermel et al. |
| 4,307,722 A | 12/1981 | Evans |
| 4,580,568 A | 4/1986 | Gianturco |
| 4,586,923 A | 5/1986 | Gould et al. |
| 4,625,597 A | 12/1986 | Cast |
| 4,694,827 A | 9/1987 | Weiner et al. |
| 4,781,682 A | 11/1988 | Patel |
| 4,822,345 A | 4/1989 | Danforth |
| 4,898,577 A | 2/1990 | Badger et al. |
| 4,899,747 A | 2/1990 | Garren et al. |
| 4,921,484 A | 5/1990 | Hillstead |
| 4,990,151 A | 2/1991 | Wallsten |
| 4,994,071 A | 2/1991 | MacGregor |
| 5,030,204 A | 7/1991 | Badger et al. |
| 5,042,707 A | 8/1991 | Taheri |
| 5,044,519 A | 9/1991 | Aoyama |
| 5,071,407 A | 12/1991 | Termin et al. |
| 5,104,399 A | 4/1992 | Lazarus |
| 5,185,004 A | 2/1993 | Lashinski et al. |
| 5,192,314 A | 3/1993 | Daskalakis |
| 5,195,968 A | 3/1993 | Lundquist et al. |
| 5,199,950 A | 4/1993 | Schmitt et al. |
| 5,207,695 A | 5/1993 | Trout, III |
| 5,282,824 A | 2/1994 | Gianturco |
| 5,290,295 A | 3/1994 | Querals et al. |
| 5,318,525 A | 6/1994 | West et al. |
| 5,320,630 A | 6/1994 | Ahmed |
| 5,330,490 A | 7/1994 | Wilk et al. |
| 5,330,503 A | 7/1994 | Yoon |
| 5,334,196 A | 8/1994 | Scott et al. |
| 5,352,197 A | 10/1994 | Hammersmark et al. |
| 5,364,351 A | 11/1994 | Heinzelman et al. |
| 5,383,880 A | 1/1995 | Hooven et al. |
| 5,387,235 A | 2/1995 | Chuter |
| 5,409,498 A | 4/1995 | Braddock et al. |
| 5,456,713 A | 10/1995 | Chuter |
| 5,456,714 A | 10/1995 | Owen |
| 5,470,337 A | 11/1995 | Moss |
| 5,474,568 A | 12/1995 | Scott et al. |
| 5,480,382 A | 1/1996 | Hammerslag et al. |
| 5,480,423 A | 1/1996 | Ravenscroft et al. |
| 5,489,295 A | 2/1996 | Piplani et al. |
| 5,522,881 A | 6/1996 | Lentz |
| 5,531,686 A | 7/1996 | Lundquist et al. |
| 5,534,007 A | 7/1996 | St. Germain et al. |
| 5,562,728 A | 10/1996 | Lazarus et al. |
| 5,571,171 A | 11/1996 | Barone et al. |
| 5,571,173 A | 11/1996 | Parodi |
| 5,582,616 A * | 12/1996 | Bolduc et al. ............. 606/143 |
| 5,591,195 A | 1/1997 | Taheri et al. |
| 5,609,627 A | 3/1997 | Goicoechea et al. |
| 5,626,613 A * | 5/1997 | Schmieding ............. 606/232 |
| 5,628,788 A | 5/1997 | Pinchuk |
| 5,632,772 A | 5/1997 | Alcime et al. |
| 5,634,936 A | 6/1997 | Linden et al. |
| 5,639,278 A | 6/1997 | Dereume et al. |
| 5,662,675 A | 9/1997 | Polanskyj Stockert et al. |
| 5,662,683 A | 9/1997 | Kay |
| 5,662,700 A | 9/1997 | Lazarus |
| 5,676,696 A | 10/1997 | Marcade |
| 5,676,697 A | 10/1997 | Mcdonald |
| 5,683,450 A | 11/1997 | Goicoechea et al. |
| 5,693,084 A | 12/1997 | Chuter |
| 5,693,086 A | 12/1997 | Goicoechea et al. |
| 5,700,269 A | 12/1997 | Pinchuk et al. |
| 5,702,343 A | 12/1997 | Alferness |
| 5,702,365 A | 12/1997 | King |
| 5,702,408 A | 12/1997 | Wales et al. |
| 5,707,376 A | 1/1998 | Kavteladze et al. |
| 5,713,907 A | 2/1998 | Hogendijk et al. |
| 5,733,325 A | 3/1998 | Robinson et al. |
| 5,749,921 A | 5/1998 | Lenker et al. |
| 5,755,777 A | 5/1998 | Chuter |
| 5,762,458 A | 6/1998 | Wang et al. |
| 5,769,884 A | 6/1998 | Solovay |
| 5,776,142 A | 7/1998 | Gunderson |
| 5,782,844 A | 7/1998 | Yoon et al. |
| 5,797,933 A | 8/1998 | Snow et al. |
| 5,800,528 A | 9/1998 | Lederman et al. |
| 5,810,882 A | 9/1998 | Bolduc et al. |
| 5,814,016 A | 9/1998 | Valley |
| 5,824,008 A | 10/1998 | Bolduc et al. |
| 5,824,037 A | 10/1998 | Fogarty et al. |
| 5,824,041 A | 10/1998 | Lenker et al. |
| 5,830,221 A * | 11/1998 | Stein et al. ............. 606/157 |
| 5,830,229 A | 11/1998 | Konya et al. |
| 5,843,160 A | 12/1998 | Rhodes |
| 5,855,565 A | 1/1999 | Bar-Cohen et al. |
| 5,855,598 A | 1/1999 | Pinchuk |
| 5,861,003 A | 1/1999 | Latson et al. |
| 5,865,791 A * | 2/1999 | Whayne et al. ............. 604/500 |
| 5,876,432 A | 3/1999 | Lau et al. |
| 5,904,713 A | 5/1999 | Leschinsky |
| 5,906,619 A | 5/1999 | Olson et al. |
| 5,906,641 A | 5/1999 | Thompson et al. |
| 5,916,263 A | 6/1999 | Goicoechea et al. |
| 5,944,750 A | 8/1999 | Tanner et al. |
| 5,957,940 A | 9/1999 | Tanner et al. |
| 5,964,772 A | 10/1999 | Bolduc et al. |
| 5,968,053 A | 10/1999 | Revelas |
| 5,972,003 A | 10/1999 | Rousseau et al. |
| 5,972,023 A | 10/1999 | Tanner et al. |
| 5,980,548 A | 11/1999 | Evans et al. |
| 5,993,401 A | 11/1999 | Inbe et al. |
| 5,993,466 A | 11/1999 | Yoon |
| 5,997,556 A | 12/1999 | Tanner et al. |
| 6,016,810 A | 1/2000 | Ravenscroft |
| 6,024,703 A | 2/2000 | Zanelli et al. |
| 6,024,763 A | 2/2000 | Lenker et al. |
| 6,027,462 A | 2/2000 | Greene et al. |
| 6,070,589 A | 6/2000 | Keith et al. |
| 6,074,418 A * | 6/2000 | Buchanan et al. ............. 623/2.11 |
| 6,077,214 A * | 6/2000 | Mortier et al. ............. 600/16 |
| 6,077,297 A | 6/2000 | Robinson et al. |
| 6,086,582 A | 7/2000 | Altman et al. |
| 6,090,137 A | 7/2000 | Schmitt |
| 6,123,722 A | 9/2000 | Fogarty et al. |
| 6,126,685 A | 10/2000 | Lenker et al. |
| 6,145,509 A | 11/2000 | Tanner |
| 6,146,339 A | 11/2000 | Biagtan et al. |
| 6,152,144 A | 11/2000 | Lesh et al. |
| 6,162,168 A * | 12/2000 | Schweich et al. ............. 600/16 |
| 6,168,610 B1 | 1/2001 | Marin et al. |
| 6,174,323 B1 * | 1/2001 | Biggs et al. ............. 606/232 |
| 6,179,809 B1 | 1/2001 | Khairkhahan et al. |
| 6,197,049 B1 | 3/2001 | Shaolian et al. |
| 6,203,550 B1 | 3/2001 | Olson |
| 6,203,568 B1 | 3/2001 | Lombardi et al. |
| 6,206,827 B1 * | 3/2001 | Chin et al. ............. 600/217 |
| 6,217,597 B1 | 4/2001 | Tanner |
| 6,224,540 B1 | 5/2001 | Lederman et al. |

(56) References Cited

U.S. PATENT DOCUMENTS

| | | | |
|---|---|---|---|
| 6,231,561 B1* | 5/2001 | Frazier et al. | 604/500 |
| 6,248,118 B1 | 6/2001 | Tanner et al. | |
| 6,250,974 B1 | 6/2001 | Kerek | |
| 6,258,021 B1* | 7/2001 | Wilk | 600/16 |
| 6,258,119 B1 | 7/2001 | Hussein et al. | |
| 6,270,516 B1 | 8/2001 | Tanner et al. | |
| 6,273,858 B1 | 8/2001 | Fox et al. | |
| 6,286,514 B1 | 9/2001 | Lemelson | |
| 6,287,315 B1 | 9/2001 | Wijeratne et al. | |
| 6,287,335 B1 | 9/2001 | Drasler et al. | |
| 6,293,906 B1 | 9/2001 | Vanden Hoek et al. | |
| 6,296,656 B1 | 10/2001 | Bolduc et al. | |
| 6,302,906 B1 | 10/2001 | Goicoechea et al. | |
| 6,309,403 B1 | 10/2001 | Minor et al. | |
| 6,319,278 B1 | 11/2001 | Quinn | |
| 6,336,933 B1* | 1/2002 | Parodi | 606/139 |
| 6,343,605 B1* | 2/2002 | Lafontaine | 128/898 |
| 6,346,118 B1 | 2/2002 | Baker et al. | |
| 6,352,561 B1 | 3/2002 | Leopold et al. | |
| 6,371,919 B1 | 4/2002 | Tanner et al. | |
| 6,398,803 B1 | 6/2002 | Layne et al. | |
| 6,402,680 B2 | 6/2002 | Mortier et al. | |
| 6,402,780 B2 | 6/2002 | Williamson, IV et al. | |
| 6,406,420 B1 | 6/2002 | McCarthy et al. | |
| 6,409,757 B1 | 6/2002 | Trout, III et al. | |
| 6,416,365 B1 | 7/2002 | Iwahori | |
| 6,416,522 B1 | 7/2002 | Strecker | |
| 6,423,059 B1 | 7/2002 | Hanson et al. | |
| 6,425,856 B1 | 7/2002 | Shapland et al. | |
| 6,428,565 B1 | 8/2002 | Wisselink | |
| 6,454,796 B1 | 9/2002 | Barkman et al. | |
| 6,458,152 B1 | 10/2002 | Khosravi et al. | |
| 6,461,365 B2 | 10/2002 | Bolduc et al. | |
| 6,468,260 B1 | 10/2002 | Bumbalough et al. | |
| 6,482,224 B1 | 11/2002 | Michler et al. | |
| 6,520,974 B2 | 2/2003 | Tannerq et al. | |
| 6,544,253 B1 | 4/2003 | Tanner | |
| 6,558,425 B2 | 5/2003 | Rockwood, Jr. | |
| 6,562,051 B1 | 5/2003 | Bolduc et al. | |
| 6,565,597 B1 | 5/2003 | Fearnot et al. | |
| 6,576,009 B2 | 6/2003 | Ryan et al. | |
| 6,580,417 B2 | 6/2003 | Rosenberg et al. | |
| 6,592,593 B1* | 7/2003 | Parodi et al. | 606/108 |
| 6,592,615 B1 | 7/2003 | Marcade et al. | |
| 6,595,912 B2 | 7/2003 | Lau et al. | |
| 6,607,555 B2 | 8/2003 | Patterson et al. | |
| 6,616,684 B1* | 9/2003 | Vidlund et al. | 606/213 |
| 6,639,278 B2 | 10/2003 | Sumida et al. | |
| 6,652,555 B1 | 11/2003 | Van Tassel et al. | |
| 6,652,572 B2 | 11/2003 | Kugler et al. | |
| 6,663,558 B2 | 12/2003 | Lau et al. | |
| 6,675,809 B2 | 1/2004 | Stack et al. | |
| 6,685,620 B2 | 2/2004 | Gifford et al. | |
| 6,702,763 B2 | 3/2004 | Murphy et al. | |
| 6,702,844 B1 | 3/2004 | Lazarus | |
| 6,709,442 B2 | 3/2004 | Miller et al. | |
| 6,719,174 B1 | 4/2004 | Swift | |
| 6,730,119 B1 | 5/2004 | Smalling et al. | |
| 6,746,460 B2 | 6/2004 | Gannoe et al. | |
| 6,800,081 B2 | 10/2004 | Parodi | |
| 6,878,164 B2 | 4/2005 | Kujawski et al. | |
| 6,929,661 B2 | 8/2005 | Bolduc et al. | |
| 6,960,217 B2 | 11/2005 | Bolduc | |
| 6,984,241 B2 | 1/2006 | Lubbers et al. | |
| 6,986,775 B2* | 1/2006 | Morales et al. | 606/139 |
| 6,986,784 B1 | 1/2006 | Weiser et al. | |
| 7,033,384 B2 | 4/2006 | Gannoe et al. | |
| 7,037,343 B2 | 5/2006 | Imran | |
| 7,060,021 B1* | 6/2006 | Wilk | 600/16 |
| 7,060,023 B2 | 6/2006 | French et al. | |
| 7,081,086 B2 | 7/2006 | Lau et al. | |
| 7,081,129 B2 | 7/2006 | Chobotov | |
| 7,128,754 B2 | 10/2006 | Bolduc | |
| 7,147,657 B2 | 12/2006 | Chiang et al. | |
| 7,155,295 B2 | 12/2006 | Lau et al. | |
| 7,179,225 B2 | 2/2007 | Shluzas et al. | |
| 7,306,623 B2 | 12/2007 | Watson | |
| 7,335,213 B1* | 2/2008 | Hyde et al. | 606/151 |
| 7,361,137 B2 | 4/2008 | Taylor et al. | |
| 7,404,824 B1* | 7/2008 | Webler et al. | 623/2.36 |
| 7,422,558 B2 | 9/2008 | Lau et al. | |
| 7,491,232 B2 | 2/2009 | Bolduc et al. | |
| 7,544,198 B2 | 6/2009 | Parodi | |
| 7,563,267 B2 | 7/2009 | Goldfarb et al. | |
| 7,591,842 B2 | 9/2009 | Parodi | |
| 7,637,932 B2 | 12/2009 | Bolduc et al. | |
| 7,704,269 B2* | 4/2010 | St. Goar et al. | 606/232 |
| 7,727,189 B2 | 6/2010 | Van Tassel et al. | |
| 7,753,922 B2* | 7/2010 | Starksen | 606/144 |
| 7,811,295 B2* | 10/2010 | Kortenbach | 606/139 |
| 7,823,267 B2 | 11/2010 | Bolduc et al. | |
| 7,828,267 B2 | 11/2010 | Iwabuchi et al. | |
| 7,828,838 B2 | 11/2010 | Bolduc et al. | |
| 7,959,663 B2 | 6/2011 | Bolduc | |
| 7,959,670 B2 | 6/2011 | Bolduc | |
| 8,075,570 B2 | 12/2011 | Bolduc et al. | |
| 8,080,050 B2 | 12/2011 | Chiang et al. | |
| 8,083,752 B2 | 12/2011 | Bolduc | |
| 8,092,519 B2 | 1/2012 | Bolduc et al. | |
| 8,231,639 B2 | 7/2012 | Bolduc et al. | |
| 8,685,044 B2 | 4/2014 | Bolduc et al. | |
| 8,690,897 B2 | 4/2014 | Bolduc | |
| 2001/0041821 A1 | 11/2001 | Wilk | |
| 2002/0026144 A1 | 2/2002 | Patterson | |
| 2002/0029077 A1 | 3/2002 | Leopold et al. | |
| 2002/0058855 A1 | 5/2002 | Schweich, Jr. et al. | |
| 2002/0065485 A1 | 5/2002 | Dubois | |
| 2002/0087169 A1* | 7/2002 | Brock et al. | 606/139 |
| 2002/0099432 A1 | 7/2002 | Yee | |
| 2002/0133054 A1 | 9/2002 | Murphy et al. | |
| 2002/0156365 A1 | 10/2002 | Tsekos | |
| 2002/0156521 A1 | 10/2002 | Ryan et al. | |
| 2002/0183827 A1 | 12/2002 | Derus et al. | |
| 2003/0018358 A1* | 1/2003 | Saadat | 606/232 |
| 2003/0060674 A1* | 3/2003 | Gifford et al. | 600/16 |
| 2003/0078465 A1* | 4/2003 | Pai et al. | 600/16 |
| 2003/0100943 A1 | 5/2003 | Bolduc | |
| 2003/0105384 A1 | 6/2003 | Sharkey et al. | |
| 2003/0105519 A1* | 6/2003 | Fasol et al. | 623/2.1 |
| 2003/0130731 A1* | 7/2003 | Vidlund et al. | 623/2.37 |
| 2003/0149463 A1 | 8/2003 | Solymar et al. | |
| 2003/0158570 A1 | 8/2003 | Ferrazzi | |
| 2003/0163085 A1 | 8/2003 | Tanner et al. | |
| 2003/0233140 A1 | 12/2003 | Hartley et al. | |
| 2004/0002731 A1 | 1/2004 | Aganon et al. | |
| 2004/0039405 A1 | 2/2004 | Petrovic et al. | |
| 2004/0044364 A1 | 3/2004 | DeVries et al. | |
| 2004/0049207 A1 | 3/2004 | Goldfarb et al. | |
| 2004/0054352 A1 | 3/2004 | Adams et al. | |
| 2004/0093057 A1 | 5/2004 | Bolduc et al. | |
| 2004/0127916 A1 | 7/2004 | Bolduc et al. | |
| 2004/0138734 A1 | 7/2004 | Chobotov et al. | |
| 2004/0153143 A1 | 8/2004 | Quiachon et al. | |
| 2004/0186566 A1* | 9/2004 | Hindrichs et al. | 623/2.37 |
| 2004/0206363 A1 | 10/2004 | McCarthy et al. | |
| 2004/0210304 A1 | 10/2004 | Seguin et al. | |
| 2004/0243170 A1 | 12/2004 | Suresh et al. | |
| 2004/0254594 A1 | 12/2004 | Alfaro | |
| 2004/0260322 A1 | 12/2004 | Rudko et al. | |
| 2004/0260383 A1 | 12/2004 | Stelter et al. | |
| 2005/0038506 A1 | 2/2005 | Webler et al. | |
| 2005/0043790 A1 | 2/2005 | Seguin | |
| 2005/0070992 A1 | 3/2005 | Bolduc et al. | |
| 2005/0113906 A9 | 5/2005 | Bolduc et al. | |
| 2005/0154401 A1 | 7/2005 | Weldon et al. | |
| 2005/0177180 A1 | 8/2005 | Kaganov | |
| 2005/0187613 A1 | 8/2005 | Bolduc et al. | |
| 2005/0197716 A1 | 9/2005 | Sharkey et al. | |
| 2005/0215874 A1 | 9/2005 | Wang et al. | |
| 2005/0240258 A1 | 10/2005 | Bolduc et al. | |
| 2005/0240260 A1 | 10/2005 | Bolduc | |
| 2006/0100640 A1 | 5/2006 | Bolduc | |
| 2006/0184224 A1 | 8/2006 | Angel | |
| 2006/0253186 A1 | 11/2006 | Bates | |

(56) References Cited

U.S. PATENT DOCUMENTS

| | | |
|---|---|---|
| 2006/0259125 A1 | 11/2006 | Peacock, III |
| 2006/0287661 A1 | 12/2006 | Bolduc et al. |
| 2007/0021753 A1 | 1/2007 | Bolduc et al. |
| 2007/0021829 A1 | 1/2007 | Bolduc |
| 2007/0032860 A1 | 2/2007 | Brooks et al. |
| 2007/0073389 A1 | 3/2007 | Bolduc et al. |
| 2007/0083255 A1 | 4/2007 | Chiang et al. |
| 2008/0065117 A1 | 3/2008 | Bolduc et al. |
| 2008/0065189 A1 | 3/2008 | Bolduc |
| 2008/0097489 A1 | 4/2008 | Goldfarb et al. |
| 2008/0132996 A1 | 6/2008 | Drasler et al. |
| 2009/0082852 A1 | 3/2009 | Bolduc et al. |
| 2009/0099650 A1 | 4/2009 | Bolduc et al. |
| 2009/0112302 A1 | 4/2009 | Stafford |
| 2009/0112303 A1 | 4/2009 | Bolduc |
| 2009/0138072 A1 | 5/2009 | Gendreau |
| 2010/0094400 A1 | 4/2010 | Bolduc et al. |
| 2011/0087320 A1 | 4/2011 | Bolduc et al. |
| 2011/0276062 A1 | 11/2011 | Bolduc |
| 2012/0065661 A1 | 3/2012 | Bolduc |
| 2012/0316578 A1 | 12/2012 | Bolduc et al. |
| 2014/0194902 A1 | 7/2014 | Bolduc et al. |
| 2014/0214051 A1 | 7/2014 | Bolduc |

FOREIGN PATENT DOCUMENTS

| | | |
|---|---|---|
| AU | 2008243229 A1 | 12/2008 |
| AU | 2006305688 B2 | 12/2012 |
| AU | 2011253682 B9 | 1/2014 |
| AU | 2011224089 B2 | 7/2014 |
| CA | 2265131 A1 | 9/1999 |
| CA | 2344252 A1 | 3/2000 |
| CA | 2729464 A1 | 6/2003 |
| CA | 2539265 A1 | 5/2005 |
| CA | 2626505 A1 | 4/2007 |
| CA | 2626106 A1 | 5/2007 |
| CA | 2625082 A1 | 7/2008 |
| CA | 2740831 A1 | 4/2010 |
| CA | 2464048 A1 | 6/2010 |
| CA | 2464900 A1 | 4/2011 |
| CA | 2554022 A1 | 11/2012 |
| CN | 1019461 B | 12/1992 |
| CN | 1422139 A | 6/2003 |
| CN | 1596087 A | 3/2005 |
| CN | 1596088 A | 3/2005 |
| CN | 1856280 A | 11/2006 |
| CN | 1870949 A | 11/2006 |
| CN | 1997318 A | 7/2007 |
| CN | 101267788 A | 9/2008 |
| CN | 101330882 A | 12/2008 |
| CN | 101352375 A | 1/2009 |
| CN | 101360466 A | 2/2009 |
| CN | 101460104 A | 6/2009 |
| CN | 101466316 A | 6/2009 |
| CN | 100525719 C | 8/2009 |
| CN | 101330882 B | 4/2011 |
| CN | 101466316 B | 6/2012 |
| DE | 3333427 C2 | 5/1991 |
| DE | 69228184 T2 | 9/1999 |
| DE | 10034105 C1 | 4/2002 |
| DE | 10297483 T5 | 12/2004 |
| EP | 0321912 A1 | 6/1989 |
| EP | 0663184 A1 | 7/1995 |
| EP | 0835642 B1 | 2/2002 |
| EP | 1369098 A1 | 12/2003 |
| EP | 1440673 A1 | 7/2004 |
| EP | 1448117 A1 | 8/2004 |
| EP | 1675528 A2 | 7/2006 |
| EP | 1725172 A2 | 11/2006 |
| EP | 1734872 A1 | 12/2006 |
| EP | 1948080 A2 | 7/2008 |
| EP | 2349086 A1 | 8/2011 |
| FR | 2299548 A1 | 8/1976 |
| FR | 2865926 A1 | 8/2005 |
| GB | 2396824 A | 7/2004 |
| GB | 2417208 A | 2/2006 |
| HK | 1073240 A1 | 8/2009 |
| JP | 2001509398 A | 7/2001 |
| JP | 2001522292 A | 11/2001 |
| JP | 2001526574 A | 12/2001 |
| JP | 2002526193 A | 8/2002 |
| JP | 2005046648 A | 2/2005 |
| JP | 2005510293 A | 4/2005 |
| JP | 2005510303 A | 4/2005 |
| JP | 2007508894 A | 4/2007 |
| JP | 2007535339 A | 12/2007 |
| JP | 2009512497 A | 3/2009 |
| JP | 2009512498 A | 3/2009 |
| JP | 2009512499 A | 3/2009 |
| JP | 2009078172 A | 4/2009 |
| JP | 2009106768 A | 5/2009 |
| JP | 2009106775 A | 5/2009 |
| JP | 2009112827 A | 5/2009 |
| JP | 2009519046 A | 5/2009 |
| JP | 4405262 B2 | 1/2010 |
| JP | 10506026 A | 2/2010 |
| JP | 2010051786 A | 3/2010 |
| JP | 4465359 B2 | 5/2010 |
| JP | 2011062570 A | 3/2011 |
| JP | 4699445 B2 | 6/2011 |
| WO | WO-9300868 A1 | 1/1993 |
| WO | WO-9521592 A1 | 8/1995 |
| WO | WO-9603925 A1 | 2/1996 |
| WO | WO-9703616 A1 | 2/1997 |
| WO | WO-9712562 A1 | 4/1997 |
| WO | WO-9717039 A1 | 5/1997 |
| WO | WO-9717913 A1 | 5/1997 |
| WO | WO-9811814 A2 | 3/1998 |
| WO | WO-9853761 A1 | 12/1998 |
| WO | WO-9933402 A1 | 7/1999 |
| WO | WO-9933402 A9 | 9/1999 |
| WO | WO-9953845 A1 | 10/1999 |
| WO | WO-0064357 A1 | 1/2000 |
| WO | WO-00/16701 A1 | 3/2000 |
| WO | WO-0035350 A1 | 6/2000 |
| WO | WO-0160432 A1 | 8/2001 |
| WO | WO-03032870 A1 | 4/2003 |
| WO | WO-03/045467 A2 | 6/2003 |
| WO | WO-03/045467 A3 | 6/2003 |
| WO | WO-03045283 A1 | 6/2003 |
| WO | WO-03079935 A1 | 10/2003 |
| WO | WO-2004008975 A1 | 1/2004 |
| WO | WO-2004021872 A2 | 3/2004 |
| WO | WO-2005032333 A2 | 4/2005 |
| WO | WO-2005037076 A2 | 4/2005 |
| WO | WO-2005044073 A2 | 5/2005 |
| WO | WO-2005044147 A1 | 5/2005 |
| WO | WO-2005044148 A1 | 5/2005 |
| WO | WO-2005067660 A2 | 7/2005 |
| WO | WO-2005081936 A2 | 9/2005 |
| WO | WO-2005/102181 A1 | 11/2005 |
| WO | WO-2005032333 A3 | 4/2006 |
| WO | WO-2005067660 A3 | 4/2007 |
| WO | WO-2007046953 A2 | 4/2007 |
| WO | WO-2007046954 A2 | 4/2007 |
| WO | WO-2007046955 A2 | 4/2007 |
| WO | WO-2007047023 A2 | 4/2007 |
| WO | WO-2007053233 A2 | 5/2007 |
| WO | WO-2007046953 A3 | 6/2007 |
| WO | WO-2007046955 A3 | 10/2007 |
| WO | WO-2007047023 A3 | 10/2007 |
| WO | WO-2005081936 A3 | 11/2007 |
| WO | WO-2007053233 A3 | 1/2008 |
| WO | WO-2007046954 A3 | 11/2008 |
| WO | WO-2005044073 A3 | 3/2009 |
| WO | WO-2010004856 A1 | 1/2010 |
| WO | WO-2010044851 A1 | 4/2010 |
| WO | WO-2010044854 A1 | 4/2010 |
| WO | WO-2010044855 A1 | 4/2010 |
| WO | WO-2010044856 A1 | 4/2010 |

(56) References Cited

FOREIGN PATENT DOCUMENTS

OTHER PUBLICATIONS

Final Office Action mailed on Dec. 9, 2010, for U.S. Appl. No. 11/365,056, filed Mar. 1, 2006, 10 pages.
International Search Report mailed on Aug. 30, 2005, for PCT Patent Application No. PCT/US2005/005453, filed on Feb. 22, 2005, published on Nov. 3, 2005, as WO 2005/102181, one page.
Written Opinion mailed on Aug. 30, 2005, for PCT Patent Application No. PCT/US2005/005453, filed on Feb. 22, 2005, published on Nov. 3, 2005, as WO 2005/102181, 3 pages.
International Preliminary Examination Report mailed on Mar. 13, 2006, for PCT Patent Application No. PCT/US2005/005453, filed on Feb. 22, 2005, published on Nov. 3, 2005, as WO 2005/102181, 3 pages.
"5mm Origin Tracker It Runs in Circles Around Staples", Guidant Origin Advertising Literature, (1995), 2 pgs.
"U.S. Appl. No. 10/271,334, Examiner Interview Summary mailed Feb. 11, 2005", 2 pgs.
"U.S. Appl. No. 10/271,334, Non Final Office Action mailed May 18, 2004", 9 pgs.
"U.S. Appl. No. 10/271,334, Notice of Allowance mailed Feb. 11, 2005", 6 pgs.
"U.S. Appl. No. 10/271,334, Notice of Allowance mailed Mar. 17, 2005", 3 pgs.
"U.S. Appl. No. 10/271,334, Notice of Allowance mailed Aug. 26, 2005", 3 pgs.
"U.S. Appl. No. 10/271,334, Response filed Mar. 15, 2004 to Restriction Requirement mailed Sep. 23, 2003", 1 pg.
"U.S. Appl. No. 10/271,334, Response filed Nov. 22, 2004 to Non Final Office Action mailed May 18, 2004", 6 pgs.
"U.S. Appl. No. 10/271,334, Restriction Requirement mailed Sep. 23, 2003", 4 pgs.
"U.S. Appl. No. 10/271,334, Supplemental Response filed Jan. 28, 2005 to Non Final Office Action mailed May 18, 2004", 6 pgs.
"U.S. Appl. No. 10/307,226, 312 Amendment filed Oct. 24, 2011", 3 pgs.
"U.S. Appl. No. 10/307,226, Appeal Brief filed Oct. 14, 2010", 15 pgs.
"U.S. Appl. No. 10/307,226, Final Office Action mailed Jun. 27, 2008", 6 pgs.
"U.S. Appl. No. 10/307,226, Final Office Action mailed Dec. 12, 2006", 5 pgs.
"U.S. Appl. No. 10/307,226, Non Final Office Action mailed Mar. 13, 2006", 6 pgs.
"U.S. Appl. No. 10/307,226, Non Final Office Action mailed Jun. 12, 2007", 5 pgs.
"U.S. Appl. No. 10/307,226, Non Final Office Action mailed Sep. 9, 2009", 16 pgs.
"U.S. Appl. No. 10/307,226, Notice of Allowance mailed Jul. 22, 2011", 8 pgs.
"U.S. Appl. No. 10/307,226, Preliminary Amendment filed Jul. 22, 2005", 3 pgs.
"U.S. Appl. No. 10/307,226, PTO Response to 312 Amendment mailed Nov. 10, 2011", 3 pgs.
"U.S. Appl. No. 10/307,226, Response filed Apr. 9, 2007 to Final Office Action mailed Dec. 12, 2006", 7 pgs.
"U.S. Appl. No. 10/307,226, Response filed Jun. 23, 2009 to Final Office Action mailed Jun. 27, 2008", 10 pgs.
"U.S. Appl. No. 10/307,226, Response filed Sep. 15, 2006 to Non Final Office Action mailed Mar. 13, 2006", 6 pgs.
"U.S. Appl. No. 10/307,226, Response filed Dec. 14, 2007 to Non Final Office Action mailed Jun. 12, 2007", 7 pgs.
"U.S. Appl. No. 10/669,881, Final Office Action mailed Jan. 25, 2008", 7 pgs.
"U.S. Appl. No. 10/669,881, Non Final Office Action mailed Jan. 27, 2006", 5 pgs.
"U.S. Appl. No. 10/669,881, Notice of Allowance mailed Oct. 8, 2008", 16 pgs.
"U.S. Appl. No. 10/669,881, Preliminary Amendment May 6, 2005", 3 pgs.
"U.S. Appl. No. 10/669,881, Response filed Mar. 11, 2008 to Final Office Action mailed Jan. 25, 2008", 8 pgs.
"U.S. Appl. No. 10/669,881, Response filed May 15, 2006 to Non Final Office Action mailed Jan. 27, 2006", 9 pgs.
"U.S. Appl. No. 10/669,881, Response filed Sep. 7, 2007 to Restriction Requirement mailed Jun. 19, 2007", 4 pgs.
"U.S. Appl. No. 10/669,881, Response filed Oct. 2, 2006 to Restriction Requirement mailed Jul. 27, 2006", 6 pgs.
"U.S. Appl. No. 10/669,881, Restriction Requirement Jul. 27, 2006", 5 pgs.
"U.S. Appl. No. 10/669,881, Restriction Requirement mailed Jun. 19, 2007", 5 pgs.
"U.S. Appl. No. 10/692,282, Non Final Office Action mailed Aug. 30, 2005", 6 pgs.
"U.S. Appl. No. 10/692,282, Notice of Allowance mailed Jun. 13, 2006", 6 pgs.
"U.S. Appl. No. 10/692,282, Response filed Feb. 22, 2005 to Restriction Requirement mailed Aug. 17, 2004", 4 pgs.
"U.S. Appl. No. 10/692,282, Response filed Feb. 28, 2006 to Non Final Office Action mailed Aug. 30, 2005", 5 pgs.
"U.S. Appl. No. 10/692,282, Restriction Requirement mailed Aug. 17, 2004", 6 pgs.
"U.S. Appl. No. 10/693,255, Examiner Interview Summary mailed Feb. 17, 2005", 3 pgs.
"U.S. Appl. No. 10/693,255, Non Final Office Action mailed Dec. 9, 2004", 6 pgs.
"U.S. Appl. No. 10/693,255, Notice of Allowance mailed Mar. 9, 2005", 9 pgs.
"U.S. Appl. No. 10/752,435, Final Office Action mailed May 14, 2010", 8 pgs.
"U.S. Appl. No. 10/752,435, Final Office Action mailed Jul. 12, 2007", 8 pgs.
"U.S. Appl. No. 10/752,435, Final Office Action mailed Dec. 8, 2008", 8 pgs.
"U.S. Appl. No. 10/752,435, Non Final Office Action mailed Mar. 18, 2008", 7 pgs.
"U.S. Appl. No. 10/752,435, Non Final Office Action mailed Jul. 21, 2009", 7 pgs.
"U.S. Appl. No. 10/752,435, Non Final Office Action mailed Oct. 19, 2006", 17 pgs.
"U.S. Appl. No. 10/786,465, Applicant's Summary of Examiner Interview filed Jun. 6, 2012", 2 pgs.
"U.S. Appl. No. 10/786,465, Corrected Notice of Allowability mailed Jul. 2, 2012", 4 pgs.
"U.S. Appl. No. 10/786,465, Examiner Interview Summary mailed Mar. 3, 2008", 2 pgs.
"U.S. Appl. No. 10/786,465, Examiner Interview Summary mailed Apr. 26, 2011", 3 pgs.
"U.S. Appl. No. 10/786,465, Final Office Action mailed Jan. 21, 2009", 8 pgs.
"U.S. Appl. No. 10/786,465, Non Final Office Action mailed Mar. 26, 2010", 8 pgs.
"U.S. Appl. No. 10/786,465, Non Final Office Action mailed Jul. 23, 2007", 7 pgs.
"U.S. Appl. No. 10/786,465, Notice of Allowance mailed Mar. 14, 2012", 11 pgs.
"U.S. Appl. No. 10/786,465, Preliminary Amendment filed Mar. 16, 2005", 3 pgs.
"U.S. Appl. No. 10/786,465, Response filed Jan. 25, 2008 to Non Final Office Action mailed Jul. 23, 2007", 8 pgs.
"U.S. Appl. No. 10/786,465, Response filed Apr. 9, 2007 to Restriction Requirement mailed Dec. 8, 2006", 4 pgs.
"U.S. Appl. No. 10/786,465, Response filed Apr. 26, 2011 to Non Final Office Action mailed Mar. 26, 2010", 14 pgs.
"U.S. Appl. No. 10/786,465, Response filed Jul. 22, 2009 to Final Office Action mailed Jan. 21, 2009", 5 pgs.
"U.S. Appl. No. 10/786,465, Response filed Sep. 19, 2008 to Restriction Requirement mailed Jul. 24, 2008", 4 pgs.
"U.S. Appl. No. 10/786,465, Restriction Requirement mailed Jul. 24, 2008", 5 pgs.

(56) References Cited

OTHER PUBLICATIONS

"U.S. Appl. No. 10/786,465, Restriction Requirement mailed Dec. 8, 2006", 6 pgs.

"U.S. Appl. No. 10/786,465, Supplemental Amendment filed Mar. 18, 2008", 8 pgs.

"U.S. Appl. No. 10/786,465, Supplemental Notice of Allowability mailed May 8, 2012", 6 pgs.

"U.S. Appl. No. 10/808,216, Preliminary Amendment filed Jun. 15, 2005", 3 pgs.

"U.S. Appl. No. 11/166,411, 312 Amendment filed Nov. 23, 2011", 3 pgs.

"U.S. Appl. No. 11/166,411, Final Office Action mailed Dec. 3, 2009", 5 pgs.

"U.S. Appl. No. 11/166,411, Non Final Office Action mailed May 5, 2009", 8 pgs.

"U.S. Appl. No. 11/166,411, Notice of Allowance mailed Jan. 6, 2011", 4 pgs.

"U.S. Appl. No. 11/166,411, Notice of Allowance mailed Aug. 23, 2011", 5 pgs.

"U.S. Appl. No. 11/166,411, Preliminary Amendment filed Oct. 2, 2006", 5 pgs.

"U.S. Appl. No. 11/166,411, PTO Response to 312 Communication mailed Dec. 13, 2011", 2 pgs.

"U.S. Appl. No. 11/166,411, Response filed Jan. 12, 2009 to Restriction Requirement mailed Jul. 15, 2008", 5 pgs.

"U.S. Appl. No. 11/166,411, Response filed Jun. 7, 2010 to Final Office Action mailed Dec. 3, 2009", 5 pgs.

"U.S. Appl. No. 11/166,411, Response filed Nov. 9, 2009 to Non Final Office Action mailed May 5, 2009", 8 pgs.

"U.S. Appl. No. 11/166,411, Restriction Requirement mailed Jul. 15, 2008", 5 pgs.

"U.S. Appl. No. 11/166,411, Supplemental Preliminary Amendment filed Oct. 30, 2007", 7 pgs.

"U.S. Appl. No. 11/166,428, Final Office Action mailed Jan. 12, 2009", 10 pgs.

"U.S. Appl. No. 11/166,428, Final Office Action mailed Mar. 16, 2010", 8 pgs.

"U.S. Appl. No. 11/166,428, Non Final Office Action mailed May 14, 2008", 6 pgs.

"U.S. Appl. No. 11/166,428, Non Final Office Action mailed Jun. 16, 2009", 10 pgs.

"U.S. Appl. No. 11/254,444, Notice of Allowance mailed Mar. 9, 2010", 7 pgs.

"U.S. Appl. No. 11/254,444, Notice of Allowance mailed Apr. 5, 2010", 4 pgs.

"U.S. Appl. No. 11/254,444, Notice of Allowance mailed Jun. 29, 2010", 6 pgs.

"U.S. Appl. No. 11/254,444, Preliminary Amendment filed Oct. 20, 2005".

"U.S. Appl. No. 11/254,444, Preliminary Amendment filed Nov. 15, 2005", 8 pgs.

"U.S. Appl. No. 11/254,444, Response filed Dec. 18, 2009 to Restriction Requirement mailed Jun. 19, 2009", 2 pgs.

"U.S. Appl. No. 11/254,444, Restriction Requirement mailed Jun. 19, 2009", 6 pgs.

"U.S. Appl. No. 11/254,619, Final Office Action mailed Jun. 30, 2010", 11 pgs.

"U.S. Appl. No. 11/254,619, Final Office Action mailed Oct. 20, 2011", 12 pgs.

"U.S. Appl. No. 11/254,619, Non Final Office Action mailed Feb. 3, 2011", 9 pgs.

"U.S. Appl. No. 11/254,619, Non Final Office Action mailed Oct. 1, 2009", 6 pgs.

"U.S. Appl. No. 11/254,619, Response filed Apr. 1, 2010 to Non Final Office Action mailed Oct. 1, 2009", 5 pgs.

"U.S. Appl. No. 11/254,619, Response filed Apr. 20, 2012 to Final Office Action mailed Oct. 20, 2011", 11 pgs.

"U.S. Appl. No. 11/254,619, Response filed Aug. 3, 2011 to Non Final Office Action mailed Feb. 3, 2011", 13 pgs.

"U.S. Appl. No. 11/254,619, Response filed Dec. 29, 2010 to Final Office Action mailed Jun. 30, 2010", 12 pgs.

"U.S. Appl. No. 11/254,950, Non Final Office Action mailed Mar. 30, 2009", 6 pgs.

"U.S. Appl. No. 11/254,950, Notice of Allowance mailed Feb. 26, 2010", 4 pgs.

"U.S. Appl. No. 11/254,950, Notice of Allowance mailed Jun. 22, 2010", 4 pgs.

"U.S. Appl. No. 11/254,950, Preliminary Amendment filed Nov. 18, 2005", 4 pgs.

"U.S. Appl. No. 11/254,950, Response filed Jan. 5, 2009 to Restriction Requirement mailed Jul. 9, 2008", 7 pgs.

"U.S. Appl. No. 11/254,950, Response filed Oct. 5, 2009 to Non Final Office Action mailed Mar. 30, 2009", 5 pgs.

"U.S. Appl. No. 11/254,950, Restriction Requirement mailed Jul. 9, 2008", 9 pgs.

"U.S. Appl. No. 11/255,116, Non Final Office Action mailed May 14, 2008", 15 pgs.

"U.S. Appl. No. 11/255,116, Notice of Allowance mailed Aug. 10, 2009", 4 pgs.

"U.S. Appl. No. 11/255,116, Preliminary Amendment filed Nov. 18, 2005", 4 pgs.

"U.S. Appl. No. 11/255,116, Response filed May 20, 2009 to Restriction Requirement mailed Mar. 18, 2009", 4 pgs.

"U.S. Appl. No. 11/255,116, Response filed Nov. 17, 2008 to Non Final Office Action mailed May 24, 2008", 7 pgs.

"U.S. Appl. No. 11/255,116, Restriction Requirement mailed Mar. 18, 2009", 7 pgs.

"U.S. Appl. No. 11/365,056, Response filed Sep. 28, 2010 to Non Final Office Action mailed Mar. 23, 2010", 5 pgs.

"U.S. Appl. No. 11/365,056, Response filed Dec. 10, 2009 to Restriction Requirement mailed Jun. 10, 2009", 44 pgs.

"U.S. Appl. No. 11/365,056, Restriction Requirement mailed Jun. 10, 2009", 5 pgs.

"U.S. Appl. No. 11/488,305, Advisory Action mailed Jun. 7, 2013", 3 pgs.

"U.S. Appl. No. 11/488,305, Final Office Action mailed Mar. 6, 2013", 9 pgs.

"U.S. Appl. No. 11/488,305, Final Office Action mailed Apr. 13, 2011", 9 pgs.

"U.S. Appl. No. 11/488,305, Non Final Office Action mailed Sep. 1, 2010", 8 pgs.

"U.S. Appl. No. 11/488,305, Non Final Office Action mailed Sep. 14, 2012", 9 pgs.

"U.S. Appl. No. 11/488,305, Non Final Office Action mailed Oct. 31, 2011", 6 pgs.

"U.S. Appl. No. 11/488,305, Response filed Feb. 1, 2011 to Non Final Office Action mailed Sep. 1, 2010", 12 pgs.

"U.S. Appl. No. 11/488,305, Response filed Feb. 13, 2013 to Non Final Office Action mailed Sep. 14, 2012", 10 pgs.

"U.S. Appl. No. 11/488,305, Response filed Apr. 26, 2012 to Non Final Office Action mailed Oct. 31, 2011", 12 pgs.

"U.S. Appl. No. 11/488,305, Response filed May 3, 2013 to Final Office Action mailed Mar. 6, 2013", 11 pgs.

"U.S. Appl. No. 11/488,305, Response filed Jul. 2, 2010 to Restriction Requirement mailed Jan. 5, 2010", 8 pgs.

"U.S. Appl. No. 11/488,305, Response filed Oct. 13, 2011 to Final Office Action mailed Apr. 13, 2011", 11 pgs.

"U.S. Appl. No. 11/488,305, Restriction Requirement mailed Jan. 5, 2010", 6 pgs.

"U.S. Appl. No. 11/540,427, Appeal Brief filed Aug. 26, 2010", 26 pgs.

"U.S. Appl. No. 11/540,427, Final Office Action mailed Jul. 21, 2009", 9 pgs.

"U.S. Appl. No. 11/540,427, Non Final Office Action mailed Oct. 6, 2008", 10 pgs.

"U.S. Appl. No. 11/540,427, Notice of Allowance mailed Apr. 11, 2011", 8 pgs.

"U.S. Appl. No. 11/540,427, Notice of Allowance mailed Apr. 29, 2011", 8 pgs.

"U.S. Appl. No. 11/540,427, Preliminary Amendment filed Oct. 3, 2007", 5 pgs.

(56) References Cited

OTHER PUBLICATIONS

"U.S. Appl. No. 11/540,427, Response filed Apr. 10, 2009 to Non Final Office Action mailed Oct. 6, 2008", 6 pgs.
"U.S. Appl. No. 11/540,428, Final Office Action mailed Aug. 4, 2011", 9 pgs.
"U.S. Appl. No. 11/540,428, Non Final Office Action mailed Nov. 12, 2010", 8 pgs.
"U.S. Appl. No. 11/540,428, Response filed May 12, 2011 to Non Final Office Action mailed Nov. 12, 2010", 12 pgs.
"U.S. Appl. No. 11/540,428, Response filed Oct. 1, 2010 to Restriction Requirement mailed Mar. 29, 2010", 6 pgs.
"U.S. Appl. No. 11/540,428, Restriction Requirement mailed Mar. 29, 2010", 9 pgs.
"U.S. Appl. No. 11/580,584, Appeal Brief filed Nov. 15, 2010", 11 pgs.
"U.S. Appl. No. 11/580,584, Final Office Action mailed Jan. 22, 2009", 9 pgs.
"U.S. Appl. No. 11/580,584, Final Office Action mailed Oct. 16, 2009", 8 pgs.
"U.S. Appl. No. 11/580,584, Non Final Office Action mailed Apr. 18, 2008", 6 pgs.
"U.S. Appl. No. 11/580,584, Notice of Allowance mailed Feb. 4, 2011", 7 pgs.
"U.S. Appl. No. 11/580,584, Response filed Jul. 22, 2009 to Final Office Action mailed Jan. 22, 2009", 6 pgs.
"U.S. Appl. No. 11/580,584, Response filed Oct. 20, 2008 to Non Final Office Action mailed Apr. 18, 2008", 5 pgs.
"U.S. Appl. No. 11/978,752, Final Office Action mailed Dec. 22, 2010", 6 pgs.
"U.S. Appl. No. 11/978,752, Non Final Office Action mailed May 20, 2010", 6 pgs.
"U.S. Appl. No. 11/978,752, Notice of Allowance mailed Aug. 31, 2011", 5 pgs.
"U.S. Appl. No. 11/978,752, Response filed May 10, 2010 to Restriction Requirement mailed Nov. 6, 2009", 4 pgs.
"U.S. Appl. No. 11/978,752, Response filed Jun. 22, 2011 to Final Office Action mailed Dec. 22, 2010", 6 pgs.
"U.S. Appl. No. 11/978,752, Response filed Nov. 5, 2010 to Non Final Office Action mailed May 20, 2010", 4 pgs.
"U.S. Appl. No. 11/978,752, Restriction Requirement mailed Nov. 6, 2009", 7 pgs.
"U.S. Appl. No. 11/978,753, Final Office Action mailed May 2, 2011", 8 pgs.
"U.S. Appl. No. 11/978,753, Non Final Office Action mailed Sep. 3, 2010", 8 pgs.
"U.S. Appl. No. 11/978,753, Response filed Mar. 3, 2011 to Non Final Office Action mailed Sep. 3, 2010", 9 pgs.
"U.S. Appl. No. 11/981,112, Final Office Action mailed Apr. 29, 2010", 9 pgs.
"U.S. Appl. No. 11/981,112, Non Final Office Action mailed Jul. 8, 2009", 11 pgs.
"U.S. Appl. No. 12/288,031, Advisory Action mailed Apr. 12, 2013", 3 pgs.
"U.S. Appl. No. 12/288,031, Final Office Action mailed Jan. 3, 2012", 9 pgs.
"U.S. Appl. No. 12/288,031, Non Final Office Action mailed May 10, 2012", 8 pgs.
"U.S. Appl. No. 12/288,031, Non Final Office Action mailed Jul. 15, 2013", 9 pgs.
"U.S. Appl. No. 12/288,031, Response filed Mar. 25, 2013 to Final Office Action mailed Jan. 3, 2013", 11 pgs.
"U.S. Appl. No. 12/288,031, Response filed Apr. 4, 2012 to Restriction Requirement mailed Nov. 4, 2011", 3 pgs.
"U.S. Appl. No. 12/288,031, Response filed Oct. 10, 2012 to Non Final Office Action mailed May 10, 2012", 11 pgs.
"U.S. Appl. No. 12/288,031, Restriction Requirement mailed Nov. 4, 2011", 9 pgs.
"U.S. Appl. No. 12/288,032, Restriction Requirement mailed Nov. 4, 2011", 9 pgs.
"U.S. Appl. No. 12/288,034, Non Final Office Action mailed Jun. 22, 2012", 7 pgs.
"U.S. Appl. No. 12/288,034, Response filed May 1, 2012 to Restriction Requirement mailed Nov. 3, 2011", 4 pgs.
"U.S. Appl. No. 12/288,034, Response filed Dec. 21, 2012 to Non Final Office Action mailed Jun. 22, 2012", 12 pgs.
"U.S. Appl. No. 12/288,034, Restriction Requirement mailed Nov. 3, 2011", 9 pgs.
"U.S. Appl. No. 12/288,045, Restriction Requirement mailed Nov. 16, 2011", 9 pgs.
"U.S. Appl. No. 12/315,015, Advisory Action mailed Sep. 12, 2012", 3 pgs.
"U.S. Appl. No. 12/315,015, Final Office Action mailed Apr. 26, 2012", 7 pgs.
"U.S. Appl. No. 12/315,015, Non Final Office Action mailed Oct. 6, 2011", 11 pgs.
"U.S. Appl. No. 12/315,015, Preliminary Amendment filed Mar. 10, 2009", 3 pgs.
"U.S. Appl. No. 12/315,015, Response filed Apr. 6, 2012 to Non Final Office Action mailed Oct. 6, 2011", 12 pgs.
"U.S. Appl. No. 12/315,015, Response filed Aug. 27, 2012 to Final Office Action mailed Apr. 26, 2012", 6 pgs.
"U.S. Appl. No. 12/653,219, Non Final Office Action mailed May 30, 2012", 16 pgs.
"U.S. Appl. No. 12/917,842, Non Final Office Action mailed Nov. 13, 2012", 6 pgs.
"U.S. Appl. No. 12/917,842, Notice of Allowance mailed May 20, 2013", 8 pgs.
"U.S. Appl. No. 12/917,842, Notice of Allowance mailed Aug. 27, 2013", 6 pgs.
"U.S. Appl. No. 12/917,842, Response filed Apr. 15, 2013 to Non Final Office Action mailed Nov. 13, 2012", 9 pgs.
"U.S. Appl. No. 12/917,842, Response filed Oct. 15, 2012 to Restriction Requirement mailed Sep. 14, 2012", 2 pgs.
"U.S. Appl. No. 12/917,842, Restriction Requirement mailed Sep. 14, 2012", 5 pgs.
"U.S. Appl. No. 13/162,384, Final Office Action mailed Aug. 27, 2013", 14 pgs.
"U.S. Appl. No. 13/162,384, Non Final Office Action mailed Mar. 28, 2013", 8 pgs.
"U.S. Appl. No. 13/162,384, Preliminary Amendment filed Jun. 16, 2011", 7 pgs.
"U.S. Appl. No. 13/162,384, Response filed Jun. 27, 2013", 9 pgs.
"U.S. Appl. No. 13/495,836, Non Final Office Action mailed Aug. 5, 2013", 7 pgs.
"U.S. Appl. No. 13/495,836, Non Final Office Action mailed Dec. 26, 2012", 9 pgs.
"U.S. Appl. No. 13/495,836, Preliminary Amendment filed Jun. 13, 2012", 8 pgs.
"U.S. Appl. No. 13/495,836, Response filed Mar. 25, 2013 to Non Final Office Action mailed Dec. 26, 2012", 9 pgs.
"Australian Application Serial No. 2002351188, Office Action mailed Mar. 30, 2007", 1 pg.
"Australian Application Serial No. 2002351188, Office Action mailed Dec. 8, 2008", 3 pgs.
"Australian Application Serial No. 2002353807, First Examiner Report mailed Nov. 16, 2006", 2 pgs.
"Australian Application Serial No. 2004277897, First Examiner Report mailed Oct. 14, 2009", 2 pgs.
"Australian Application Serial No. 2004277897, Response filed Jul. 14, 2011 to First Examiner Report mailed Oct. 14, 2009", 9 pgs.
"Australian Application Serial No. 2004287354, Office Action mailed Oct. 13, 2009", 2 pgs.
"Australian Application Serial No. 2005235108, Office Action mailed Feb. 26, 2010", 3 pgs.
"Australian Application Serial No. 2006302908, Office Action mailed Mar. 4, 2011", 8 pgs.
"Australian Application Serial No. 2006305688, First Examiner Report mailed Mar. 10, 2011", 3 pgs.
"Australian Application Serial No. 2006305688, Response filed Oct. 22, 2012 to First Examiner Report mailed Mar. 10, 2011", 16 pgs.
"Australian Application Serial No. 2006305689, Office Action mailed Sep. 5, 2011", 3 pgs.

(56) References Cited

OTHER PUBLICATIONS

"Australian Application Serial No. 2006309241, Office Action mailed Mar. 4, 2011", 6 pgs.
"Australian Application Serial No. 2008243229, First Examiner Report mailed Apr. 13, 2010", 2 pgs.
"Australian Application Serial No. 2008243229, Response filed May 13, 2011 to Office Action mailed Apr. 13, 2010", 15 pgs.
"Australian Application Serial No. 2011224089, First Examiners Report mailed Mar. 27, 2013", 3 pgs.
"Australian Application Serial No. 2011253682, Office Action mailed Sep. 27, 2012", 4 pgs.
"Australian Application Serial No. 2011253682, Response filed Jul. 17, 2013 to Office Action mailed Sep. 27, 2012", 19 pgs.
"Canadian Application Serial No. 2,464,900, Office Action mailed Sep. 29, 2009", 3 pgs.
"Canadian Application Serial No. 2,539,585, Office Action mailed Aug. 31, 2010", 2 pgs.
"Canadian Application Serial No. 2,539,585, Office Action mailed Sep. 19, 2012", 2 pgs.
"Canadian Application Serial No. 2,546,681, Office Action mailed Feb. 25, 2011", 3 pgs.
"Canadian Application Serial No. 2,554,022, Office Action mailed Jun. 22, 2011", 3 pgs.
"Canadian Application Serial No. 2,554,022, Office Action mailed Aug. 31, 2010", 2 pgs.
"Canadian Application Serial No. 2,558,317, Office Action mailed Aug. 31, 2010", 2 pgs.
"Canadian Application Serial No. 2,558,317, Office Action mailed Sep. 28, 2011", 3 pgs.
"Canadian Application Serial No. 2,626,403, Office Action mailed Apr. 2, 2013", 3 pgs.
"Chinese Application Serial No. 02823581.9, Office Action mailed Mar. 1, 2006", 7 pgs.
"Chinese Application Serial No. 02823581.9, Office Action mailed Apr. 18, 2008", 6 pgs.
"Chinese Application Serial No. 02823581.9, Office Action mailed Aug. 8, 2007", 4 pgs.
"Chinese Application Serial No. 02823581.9, Office Action mailed Nov. 17, 2006", 7 pgs.
"Chinese Application Serial No. 02823581.9, Response filed Jan. 31, 2007 to Office Action mailed Nov. 17, 2006", 8 pgs.
"Chinese Application Serial No. 02823581.9, Response filed Apr. 7, 2006 to Office Action mailed Mar. 1, 2006", 4 pgs.
"Chinese Application Serial No. 02823581.9, Response filed May 19, 2008 to Office Action mailed Apr. 18, 2008", 38 pgs.
"Chinese Application Serial No. 02823581.9, Response filed Dec. 3, 2007 to Office Action mailed Aug. 8, 2007", 6 pgs.
"Chinese Application Serial No. 200480027649.7, Office Action mailed Jun. 23, 2008", w/English translation, 5 pgs.
"Chinese Application Serial No. 200480027649.7, Office Action mailed Sep. 4, 2009", w/English translation, 18 pgs.
"Chinese Application Serial No. 200480027649.7, Office Action mailed Dec. 24, 2010", w/English translation, 6 pgs.
"Chinese Application Serial No. 200480027649.7, Response filed Jan. 19, 2010 to Office Action mailed Sep. 4, 2009", 5 pgs.
"Chinese Application Serial No. 200480027649.7, Response filed Mar. 8, 2011 to Office Action mailed Dec. 24, 2010", w/English translation, 7 pgs.
"Chinese Application Serial No. 200480031226.2, Office Action mailed Jan. 23, 2009", 9 pgs.
"Chinese Application Serial No. 200480031226.2, Office Action mailed Apr. 27, 2010", 7 pgs.
"Chinese Application Serial No. 200480031226.2, Office Action mailed Dec. 21, 2010", 10 pgs.
"Chinese Application Serial No. 200480031226.2, Response filed Feb. 25, 2011 to Office Action mailed Dec. 21, 2010", 18 pgs.
"Chinese Application Serial No. 200480031226.2, Response filed May 22, 2009 to Office Action mailed Jan. 23, 2009", 5 pgs.
"Chinese Application Serial No. 200480031226.2, Response filed Jul. 12, 2010 to Office Action mailed Apr. 27, 2010", Chinese only, 5 pgs.
"Chinese Application Serial No. 200580006169.7, Office Action mailed Mar. 1, 2010", w/English translation, 12 pgs.
"Chinese Application Serial No. 200580006169.7, Response filed Jul. 14, 2010 to Office Action mailed Mar. 1, 2010", w/English translation, 32 pgs.
"Chinese Application Serial No. 200580009570.6, Office Action mailed May 9, 2008".
"Chinese Application Serial No. 200580009570.6, Response filed Nov. 21, 2008 to Office Action mailed May 9, 2008", 7 pgs.
"Chinese Application Serial No. 200680034052.4, Office Action mailed May 11, 2010", w/English translation, 7 pgs.
"Chinese Application Serial No. 200680034052.4, Office Action mailed Aug. 14, 2009", w/English translation, 13 pgs.
"Chinese Application Serial No. 200680034052.4, Response filed Mar. 1, 2010 to Office Action mailed Aug. 14, 2009", 4 pgs.
"Chinese Application Serial No. 200680034052.4, Response filed Sep. 26, 2010 to Office Action mailed May 11, 2010", 5 pgs.
"Chinese Application Serial No. 200680038882.4, Office Action mailed May 11, 2010", 18 pgs.
"Chinese Application Serial No. 200680046854.7, Office Action mailed Apr. 14, 2010", 18 pgs.
"Chinese Application Serial No. 200680046854.7, Response filed Sep. 26, 2010 to Office Action mailed Apr. 14, 2010", 10 pgs.
"Chinese Application Serial No. 200680047552.1, Office Action mailed Jun. 4, 2010", 7 pgs.
"Chinese Application Serial No. 200680047552.1, Response filed Dec. 20, 2010 to Office Action mailed Jun. 4, 2010", 10 pgs.
"Chinese Application Serial No. 200810210922.X, Office Action mailed Jan. 19, 2012", 6 pgs.
"Chinese Application Serial No. 200810210922.X, Office Action mailed Apr. 2, 2010", 4 pgs.
"Chinese Application Serial No. 200810210922.X, Office Action mailed Aug. 23, 2011", 6 pgs.
"Chinese Application Serial No. 200810210922.X, Response filed Jun. 1, 2012 to Office Action mailed Jan. 19, 2012", 5 pgs.
"Chinese Application Serial No. 200810210922.X, Response filed Aug. 12, 2010 to Office Action mailed Apr. 2, 2010", 10 pgs.
"Chinese Application Serial No. 200910139527.1, Office Action mailed Jul. 12, 2010", w/English translation, 9 pgs.
"Chinese Application Serial No. 200910139527.1, Response filed Nov. 28, 2011 to Office Action mailed Jul. 12, 2010", 9 pgs.
"European Application Serial No. 02789196.9, European Search Report mailed Aug. 14, 2009", 5 pgs.
"European Application Serial No. 02789196.9, Office Action mailed Feb. 6, 2012", 4 pgs.
"European Application Serial No. 02789196.9, Office Action mailed Mar. 7, 2012", 3 pgs.
"European Application Serial No. 02789196.9, Office Action mailed Apr. 19, 2010", 4 pgs.
"European Application Serial No. 02789196.9, Office Action mailed Jul. 14, 2011", 3 pgs.
"European Application Serial No. 02789196.9, Response filed Jan. 18, 2012 to Office Action mailed Jul. 14, 2011", 19 pgs.
"European Application Serial No. 02789196.9, Response filed Feb. 16, 2012 to Office Action mailed Feb. 6, 2012", 9 pgs.
"European Application Serial No. 02789196.9, Response filed Apr. 5, 2012 to Office Action mailed Mar. 7, 2012", 5 pgs.
"European Application Serial No. 02789196.9, Response filed Oct. 25, 2010 to Office Action mailed Apr. 19, 2010", 16 pgs.
"European Application Serial No. 04788653.6, Office Action mailed May 19, 2006", 2 pgs.
"European Application Serial No. 05713941.2, Office Action mailed Dec. 13, 2007", 2 pgs.
"European Application Serial No. 06802573.3, Extended European Search Report mailed Feb. 15, 2012", 6 pgs.
"European Application Serial No. 06802573.3, Office Action mailed Mar. 5, 2012", 1 pg.
"European Application Serial No. 06802573.3, Office Action mailed May 28, 2008", 2 pgs.

(56) References Cited

OTHER PUBLICATIONS

"European Application Serial No. 06802573.3, Response filed Sep. 3, 2012 to Office Action mailed Mar. 5, 2012", 15 pgs.
"European Application Serial No. 06802578.2, European Search Report mailed Mar. 7, 2013", 10 pgs.
"European Application Serial No. 06802580.8, Office Action mailed Feb. 25, 2013", 3 pgs.
"European Application Serial No. 09820886.1, Office Action mailed Jun. 7, 2011", 2 pgs.
"European Application Serial No. 09820886.1, Response filed Dec. 8, 2011 to Office Action mailed Jun. 7, 2011", 3 pgs.
"German Application Serial No. 10297483.7, Office Action mailed Jan. 9, 2006", 4 pgs.
"German Application Serial No. 10297483.7, Office Action mailed Jul. 8, 2006", 2 pgs.
"German Application Serial No. 10297483.7, Office Action mailed and Response filed Oct. 30, 2006", 8 pgs.
"German Application Serial No. 10297483.7, Response filed Jul. 7, 2006 to Office Action mailed Jan. 9, 2006", 14 pgs.
"German Application Serial No. 10297483.7, Response filed Oct. 26, 2006 to Office Action mailed Jul. 8, 2006", 3 pgs.
"Great Britain Application Serial No. 0411107.6, Office Action mailed Feb. 28, 2005", 3 pgs.
"Great Britain Application Serial No. 0411107.6, Office Action mailed Sep. 29, 2005", 1 pg.
"Great Britain Application Serial No. 0411107.6, Response filed Aug. 23, 2005 to Office Action mailed Feb. 28, 2005", 3 pgs.
"Great Britain Application Serial No. 0411107.6, Response filed Oct. 31, 2005 to Office Action mailed Sep. 29, 2005", 4 pgs.
"Great Britain Application Serial No. 0522152.8, Office Action mailed Dec. 5, 2005", 5 pgs.
"Great Britain Application Serial No. 0522152.8, Response filed Apr. 26, 2006 to Office Action mailed Dec. 5, 2005", 48 pgs.
"International Application Serial No. PCT/US2002/032753, International Preliminary Examination Report mailed Aug. 16, 2004", 3 pgs.
"International Application Serial No. PCT/US2002/032753, International Search Report mailed Mar. 6, 2003", 1 pg.
"International Application Serial No. PCT/US2002/032753, Written Opinion mailed Aug. 26, 2003", 4 pgs.
"International Application Serial No. PCT/US2002/038365, International Preliminary Report on Patentability mailed Feb. 6, 2004", 3 pgs.
"International Application Serial No. PCT/US2002/038365, International Search Report mailed May 8, 2003", 3 pgs.
"International Application Serial No. PCT/US2002/038365, Written Opinion mailed Oct. 27, 2003", 4 pgs.
"International Application Serial No. PCT/US2004/027589, International Preliminary Report on Patentability mailed Apr. 6, 2005", 4 pgs.
"International Application Serial No. PCT/US2004/027589, International Search Report mailed Apr. 6, 2005", 1 pg.
"International Application Serial No. PCT/US2004/027589, Written Opinion mailed Apr. 6, 2005", 3 pgs.
"International Application Serial No. PCT/US2004/027590, International Preliminary Examination Report mailed Feb. 16, 2006", 3 pgs.
"International Application Serial No. PCT/US2004/027590, International Search Report mailed Jan. 12, 2005", 1 pg.
"International Application Serial No. PCT/US2004/027590, Written Opinion mailed Jan. 12, 2005", 3 pgs.
"International Application Serial No. PCT/US2004/029402, International Preliminary Report on Patentability mailed Jul. 10, 2006", 3 pgs.
"International Application Serial No. PCT/US2004/029402, International Search Report mailed Feb. 24, 2006", 1 pg.
"International Application Serial No. PCT/US2004/029402, Written Opinion mailed Feb. 24, 2006", 3 pgs.
"International Application Serial No. PCT/US2005/00059, International Preliminary Report on Patentability mailed May 18, 2007", 8 pgs.
"International Application Serial No. PCT/US2005/00059, International Search Report mailed Jan. 5, 2007", 3 pgs.
"International Application Serial No. PCT/US2005/00059, Written Opinion mailed Jan. 5, 2007", 8 pgs.
"International Application Serial No. PCT/US2005/005453, International Preliminary Report on Patentability mailed Feb. 16, 2006", 3 pgs.
"International Application Serial No. PCT/US2005/005453, International Search Report mailed Aug. 30, 2005", 1 pg.
"International Application Serial No. PCT/US2005/005453, International Written Opinion mailed Aug. 30, 2005", 3 pgs.
"International Application Serial No. PCT/US2005/005627, International Preliminary Examination Report mailed Apr. 7, 2009", 3 pgs.
"International Application Serial No. PCT/US2005/005627, International Search Report mailed Sep. 25, 2007", 1 pg.
"International Application Serial No. PCT/US2005/005627, Written Opinion mailed Sep. 25, 2007", 3 pgs.
"International Application Serial No. PCT/US2006/033741, International Preliminary Report on Patentability mailed Jul. 28, 2007", 5 pgs.
"International Application Serial No. PCT/US2006/033741, International Search Report mailed Mar. 30, 2007", 1 pg.
"International Application Serial No. PCT/US2006/033741, Written Opinion mailed Mar. 30, 2007", 4 pgs.
"International Application Serial No. PCT/US2006/033747, International Preliminary Report on Patentability mailed Mar. 1, 2011", 4 pgs.
"International Application Serial No. PCT/US2006/033747, International Search Report mailed Jul. 8, 2008", 1 pg.
"International Application Serial No. PCT/US2006/033747, Written Opinion mailed Jul. 8, 2008", 3 pgs.
"International Application Serial No. PCT/US2006/033748, International Preliminary Report on Patentability mailed Jun. 18, 2008", 7 pgs.
"International Application Serial No. PCT/US2006/033748, International Search Report mailed Aug. 15, 2007", 1 pg.
"International Application Serial No. PCT/US2006/033748, Written Opinion mailed Aug. 15, 2007", 5 pgs.
"International Application Serial No. PCT/US2006/033749, International Preliminary Report on Patentability mailed Jun. 18, 2008", 6 pgs.
"International Application Serial No. PCT/US2006/033749, International Search Report mailed Aug. 15, 2007", 1 pg.
"International Application Serial No. PCT/US2006/033749, Written Opinion mailed Aug. 15, 2007", 5 pgs.
"International Application Serial No. PCT/US2006/037085, International Preliminary Report on Patentability mailed Jul. 24, 2008", 9 pgs.
"International Application Serial No. PCT/US2006/037085, International Search Report mailed Aug. 30, 2007", 1 pg.
"International Application Serial No. PCT/US2006/037085, Written Opinion mailed Aug. 30, 2007", 7 pgs.
"International Application Serial No. PCT/US2009/005604, International Preliminary Report on Patentability mailed Jan. 13, 2011", 10 pgs.
"International Application Serial No. PCT/US2009/005604, International Search Report mailed Dec. 11, 2009", 2 pgs.
"International Application Serial No. PCT/US2009/005604, Written Opinion mailed Dec. 11, 2009", 7 pgs.
"International Application Serial No. PCT/US2009/005607, International Preliminary Report on Patentability mailed Jan. 9, 2011", 9 pgs.
"International Application Serial No. PCT/US2009/005607, International Search Report mailed Dec. 11, 2009", 2 pgs.
"International Application Serial No. PCT/US2009/005607, Written Opinion mailed Dec. 11, 2009", 6 pgs.
"International Application Serial No. PCT/US2009/005608, International Preliminary Report on Patentability mailed Jan. 14, 2011", 7 pgs.
"International Application Serial No. PCT/US2009/005608, International Search Report mailed Dec. 10, 2009", 2 pgs.
"International Application Serial No. PCT/US2009/005608, Written Opinion mailed Dec. 10, 2009", 4 pgs.

(56) References Cited

OTHER PUBLICATIONS

"International Application Serial No. PCT/US2009/005609, International Preliminary Report on Patentability mailed Jan. 9, 2011", 9 pgs.
"International Application Serial No. PCT/US2009/005609, International Search Report mailed Dec. 18, 2009", 2 pgs.
"International Application Serial No. PCT/US2009/005609, Written Opinion mailed Dec. 18, 2009", 6 pgs.
"Japanese Application Serial No. 2003-546789, Office Action mailed Feb. 26, 2009", w/English translation, 7 pgs.
"Japanese Application Serial No. 2003-546789, Office Action mailed Jun. 17, 2008", w/English translation, 6 pgs.
"Japanese Application Serial No. 2003-546789, Office Action mailed Oct. 7, 2009", 3 pgs.
"Japanese Application Serial No. 2003-546789, Response filed May 21, 2009 to Office Action mailed Feb. 26, 2009", 6 pgs.
"Japanese Application Serial No. 2003-546789, Response filed Dec. 11, 2008 to Office Action mailed Jun. 17, 2008", w/English translation, 9 pgs.
"Japanese Application Serial No. 2006-528036, Office Action mailed Jan. 19, 2010", 3 pgs.
"Japanese Application Serial No. 2006-528036, Office Action mailed Feb. 26, 2009", w/English translation, 5 pgs.
"Japanese Application Serial No. 2006-528036, Office Action mailed Jun. 23, 2008", w/English translation, 5 pgs.
"Japanese Application Serial No. 2006-528036, Response filed Dec. 25, 2008 to Office Action mailed Jun. 23, 2008", w/English translation, 9 pgs.
"Japanese Application Serial No. 2006-536616, Office Action mailed Jun. 23, 2008", 8 pgs.
"Japanese Application Serial No. 2006-536616, Response filed Dec. 19, 2008 to Office Action mailed Jun. 23, 2008", 9 pgs.
"Japanese Application Serial No. 2007500928, Office Action mailed Jul. 1, 2010", w/English translation, 10 pgs.
"Japanese Application Serial No. 2007504965, Office Action mailed Mar. 7, 2012", w/English translation, 4 pgs.
"Japanese Application Serial No. 2007504965, Office Action mailed Jun. 14, 2011", w/English translation, 4 pgs.
"Japanese Application Serial No. 2007504965, Office Action mailed Sep. 14, 2010", English translation, 1 pg.
"Japanese Application Serial No. 2007504965, Response filed Mar. 11, 2011 to Office Action mailed Sep. 14, 2010", 8 pgs.
"Japanese Application Serial No. 2008-316282, Office Action mailed May 16, 2011", 2 pgs.
"Japanese Application Serial No. 2008-316296, Office Action mailed Feb. 28, 2011", 2 pgs.
"Japanese Application Serial No. 2008-316296, Office Action mailed Jun. 22, 2010", 2 pgs.
"Japanese Application Serial No. 2008-323279, Office Action mailed Sep. 30, 2010", 1 pg.
"Japanese Application Serial No. 2008-323290, Office Action mailed Jun. 6, 2012", 8 pgs.
"Japanese Application Serial No. 2008-323290, Office Action mailed Jun. 8, 2011", 8 pgs.
"Japanese Application Serial No. 2008-323290, Response filed Dec. 7, 2011 to Office Action mailed Jun. 8, 2011", 16 pgs.
"Japanese Application Serial No. 2008-536574, Office Action mailed Mar. 11, 2010", English only, 4 pgs.
"Japanese Application Serial No. 2008-536574, Office Action mailed Oct. 3, 2011", 7 pgs.
"Japanese Application Serial No. 2008-536575, Office Action mailed Jul. 7, 2011", 5 pgs.
"Japanese Application Serial No. 2008-536576, Office Action mailed Jul. 19, 2011", 4 pgs.
"Japanese Application Serial No. 2008-536577, Notice of Allowance mailed May 30, 2012", 3 pgs.
"Japanese Application Serial No. 2008-536577, Office Action mailed Jul. 8, 2011", w/English translation, 4 pgs.
"Japanese Application Serial No. 2008-536577, Response filed Jan. 6, 2012 to Office Action mailed Jul. 8, 2011", 3 pgs.

"Laparoscopic Surgery", Medical Data International, Inc. MedPro, (1995), 190.
Bolduc, Lee, "Devices, Systems, and Methods for Prosthesis Delivery and Implantation, Including the Use of a Fastener Tool", U.S. Appl. No. 12/917,842, filed Nov. 2, 2010, 120 pgs.
Gadacz, T., et al., "The Spiral Tracker: A New Technique for Stabilizing Prosthetic Mesh in Laparoscopic Hernia Repair", Surgical Rounds, (Nov. 1995), 461-467.
Hatchett, R. L., et al., "Extraperitoneal Endoscopic Burch Repair Using a Tacker Mesh Technique", (1995), 1-4.
Newman, L., et al., "Tacker-Assisted TAPP Procedure", (1995), 2 pgs.
"U.S. Appl. No. 11/254,619, Non Final Office Action mailed Jan. 6, 2014", 19 pgs.
"U.S. Appl. No. 12/288,031, Response filed Nov. 15, 2013 to Non Final Office Action mailed Jul. 15, 2013", 11 pgs.
"U.S. Appl. No. 12/288,034, Final Office Action mailed Nov. 4, 2013", 8 pgs.
"U.S. Appl. No. 12/315,015, Non Final Office Action mailed Sep. 27, 2013", 7 pgs.
"U.S. Appl. No. 12/315,015, Response filed Dec. 27, 2013 to Non Final Office Action mailed Sep. 27, 2013", 7 pgs.
"U.S. Appl. No. 12/917,842, Notice of Allowance mailed Dec. 2, 2013", 7 pgs.
"U.S. Appl. No. 12/942,232, Non Final Office Action mailed Oct. 9, 2013", 13 pgs.
"U.S. Appl. No. 12/942,232, Response filed Jan. 9, 2014 to Non Final Office Action mailed Oct. 9, 2013", 11 pgs.
"U.S. Appl. No. 13/162,384, Advisory Action mailed Nov. 15, 2013", 3 pgs.
"U.S. Appl. No. 13/162,384, Response filed Oct. 18, 2013 to Final Office Action mailed Aug. 27, 2013", 5 pgs.
"U.S. Appl. No. 13/495,836, Notice of Allowance mailed Dec. 4, 2013", 9 pgs.
"U.S. Appl. No. 13/495,836, Response filed Nov. 5, 2013 to Non Final Office Action mailed Aug. 5, 2013", 8 pgs.
"European Application Serial No. 06802580.8, Extended European Search Report mailed Sep. 24, 2013", 8 pgs.
"U.S. Appl. No. 11/488,305, Non Final Office Action mailed Jan. 29, 2014", 10 pgs.
"U.S. Appl. No. 12/288,031, Final Office Action mailed Mar. 12, 2014", 14 pgs.
"U.S. Appl. No. 12/288,034, Advisory Action mailed Feb. 25, 2014", 3 pgs.
"U.S. Appl. No. 12/288,034, Response filed Feb. 4, 2014 to Final Office Action mailed Nov. 4, 2013", 12 pgs.
"U.S. Appl. No. 12/315,015, Advisory Action mailed Apr. 7, 2014", 3 pgs.
"U.S. Appl. No. 12/315,015, Final Office Action mailed Jan. 28, 2014", 8 pgs.
"U.S. Appl. No. 12/315,015, Response filed Mar. 28, 2014 to Final Office Action mailed Jan. 24, 2014", 5 pgs.
"Canadian Application Serial No. 2,626,403, Response filed Feb. 12, 2014 to Office Action mailed Apr. 2, 2013", 20 pgs.
"U.S. Appl. No. 11/254,619, Final Office Action mailed Jun. 19, 2014", 17 pgs.
"U.S. Appl. No. 11/254,619, Response filed May 6, 2014 to Non Final Office Action mailed Jan. 6, 2014", 10 pgs.
"U.S. Appl. No. 11/488,305, Response filed Apr. 29, 2014 to Non Final Office Action mailed Jan. 29, 2014", 9 pgs.
"U.S. Appl. No. 12/288,031, Advisory Action mailed Jul. 7, 2014", 4 pgs.
"U.S. Appl. No. 12/288,031, Non Final Office Action mailed May 10, 2012", 7 pgs.
"U.S. Appl. No. 12/288,031, Response filed Jun. 5, 2014 to Final Office Action mailed Mar. 12, 2014", 15 pgs.
"U.S. Appl. No. 12/288,034, Non Final Office Action mailed May 8, 2014", 8 pgs.
"U.S. Appl. No. 12/288,034, Response filed Aug. 1, 2014 to Non Final Office Action mailed May 8, 2014", 11 pgs.
"U.S. Appl. No. 12/315,015, Non Final Office Action mailed Aug. 4, 2014", 7 pgs.

(56) References Cited

OTHER PUBLICATIONS

"U.S. Appl. No. 12/315,015, Response filed Jun. 17, 2014 to Final Office Action mailed Jan. 28, 2014", 7 pgs.
"U.S. Appl. No. 12/942,232, Advisory Action mailed Aug. 7, 2014", 3 pgs.
"U.S. Appl. No. 12/942,232, Final Office Action mailed May 22, 2014", 17 pgs.
"U.S. Appl. No. 12/942,232, Response filed Jul. 21, 2014 to Final Office Action mailed May 22, 2014", 11 pgs.
"U.S. Appl. No. 13/162,384, Non Final Office Action mailed Jul. 21, 2014", 15 pgs.
"U.S. Appl. No. 14/210,683, Preliminary Amendment mailed Mar. 24, 2014", 7 pgs.
"Australian Application Serial No. 2011224089, Response filed Mar. 21, 2014 to First Examiners Report mailed Mar. 27, 2013", 74 pgs.
"European Application Serial No. 05713941.2, European Search Report mailed Apr. 10, 2014", 6 pgs.
"European Application Serial No. 05713941.2, Examination Notification Art. 94(3) mailed Jun. 5, 2014", 7 pgs.
"U.S. Appl. No. 11/254,619, Advisory Action mailed Sep. 24, 2014", 3 pgs.
"U.S. Appl. No. 11/254,619, Examiner Interview Summary mailed Sep. 18, 2014", 3 pgs.
"U.S. Appl. No. 11/254,619, Final Office Action mailed Jun. 30, 2010", 10 pgs.
"U.S. Appl. No. 11/254,619, Final Office Action mailed Oct. 20, 2011", 11 pgs.
"U.S. Appl. No. 11/254,619, Non Final Office Action mailed Feb. 3, 2011", 8 pgs.
"U.S. Appl. No. 11/254,619, Non Final Office Action mailed Oct. 1, 2009", 5 pgs.
"U.S. Appl. No. 11/254,619, Response filed Sep. 15, 2014 to Final Office Action mailed Jun. 19, 2014", 12 pgs.
"U.S. Appl. No. 11/488,305, Final Office Action mailed Aug. 14, 2014", 11 pgs.
"U.S. Appl. No. 12/288,031, Response filed Sep. 10, 2014 to Advisory Action mailed Jul. 7, 2014", 16 pgs.
"European Application Serial No. 05723408.0, Examination Notification Art. 94(3) mailed Jul. 10, 2014", 6 pgs.

* cited by examiner

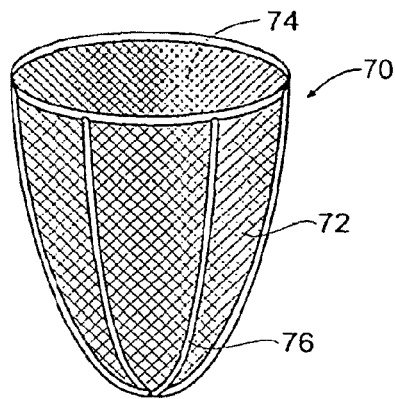
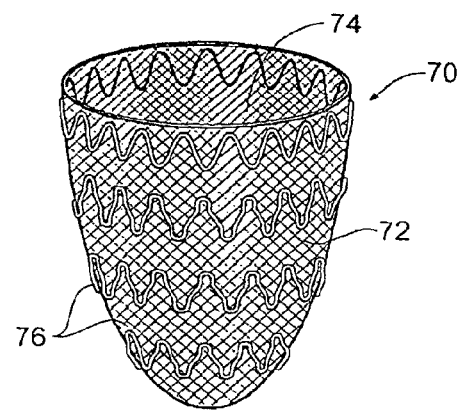
Fig. 19A    Fig. 19B
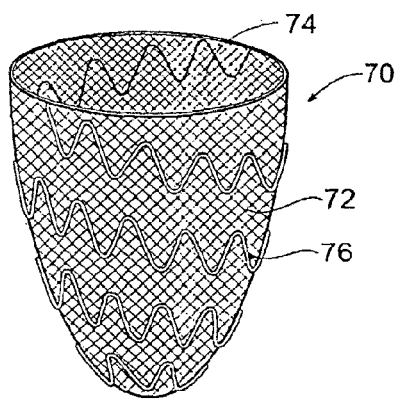
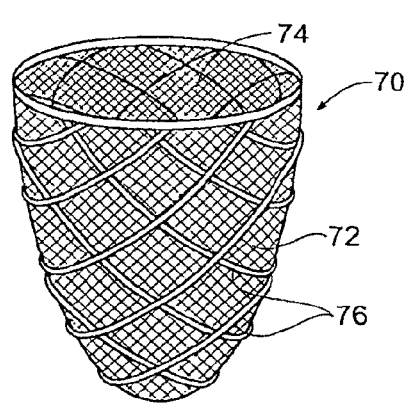
Fig. 19C    Fig. 19D
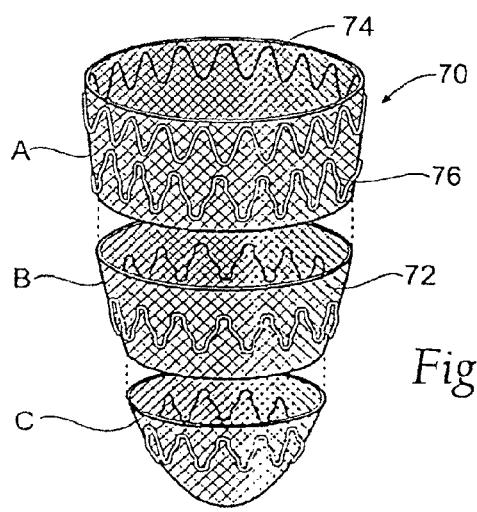
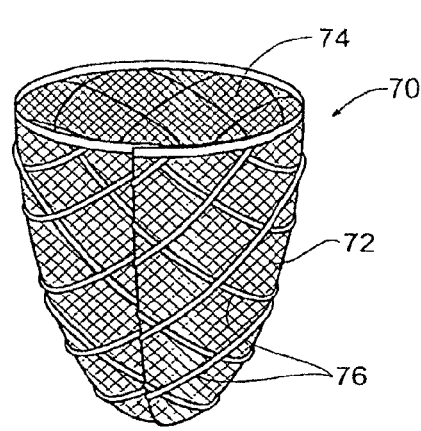
Fig. 19E    Fig. 19F

DEVICES, SYSTEMS, AND METHODS FOR SUPPORTING TISSUE AND/OR STRUCTURES WITHIN A HOLLOW BODY ORGAN

RELATED APPLICATIONS

This application is a continuation of U.S. application Ser. No. 11/365,056, filed on Mar. 1, 2006 now abandoned, which is a continuation of U.S. application Ser. No. 10/808,216, filed Mar. 24, 2004 now abandoned, which is a continuation-in-part of U.S. application Ser. No. 10/307,226 (now U.S. Pat. No. 8,075,570), filed on Nov. 29, 2002. U.S. application Ser. No. 10/808,216 is also a continuation-in-part of U.S. application Ser. No. 10/271,334 (now U.S. Pat. No. 6,960,217), filed on Oct. 15, 2002, which claims benefit of U.S. Provisional Application No. 60/333,937, filed Nov. 28, 2001. The contents of all these disclosures are incorporated herein in their entirety.

FIELD OF THE INVENTION

The features of the invention are generally applicable to devices, systems, and methods that support tissue and/or structures within a hollow body organ. In a more particular sense, the features of the invention are applicable to improving heart function by supporting tissue and related structures in the heart, e.g., for the treatment of conditions such as congestive heart failure and/or atrial fibrillation and/or septal defects.

BACKGROUND OF THE INVENTION

Hollow body organs are shaped in particular native ways to perform specific native functions. When a body organ looses its native shape due to disease, injury, or simply the natural aging process, the native functions can be adversely affected. The heart serves as a good example of this marriage between native shape and native function, as well as the dysfunctions that can occur should the native shape change.

I. The Anatomy of a Healthy Heart

The heart (see FIG. 1) is slightly larger than a clenched fist. It is a double (left and right side), self-adjusting muscular pump, the parts of which work in unison to propel blood to all parts of the body. The right side of the heart receives poorly oxygenated ("venous") blood from the body from the superior vena cava and inferior vena cava and pumps it through the pulmonary artery to the lungs for oxygenation. The left side receives well-oxygenation ("arterial") blood from the lungs through the pulmonary veins and pumps it into the aorta for distribution to the body.

The heart has four chambers, two on each side—the right and left atria, and the right and left ventricles. The atria are the blood-receiving chambers, which pump blood into the ventricles. A wall composed of membranous and muscular parts, called the interatrial septum, separates the right and left atria. The ventricles are the blood-discharging chambers. A wall composed of membranous and muscular parts, called the interventricular septum, separates the right and left ventricles.

The synchronous pumping actions of the left and right sides of the heart constitute the cardiac cycle. The cycle begins with a period of ventricular relaxation, called ventricular diastole. The cycle ends with a period of ventricular contraction, called ventricular systole.

The heart has four valves (see FIGS. 2 and 3) that ensure that blood does not flow in the wrong direction during the cardiac cycle; that is, to ensure that the blood does not back flow from the ventricles into the corresponding atria, or back flow from the arteries into the corresponding ventricles. The valve between the left atrium and the left ventricle is the mitral valve. The valve between the right atrium and the right ventricle is the tricuspid valve. The pulmonary valve is at the opening of the pulmonary artery. The aortic valve is at the opening of the aorta.

At the beginning of ventricular diastole (i.e., ventricular filling) (see FIG. 2), the aortic and pulmonary valves are closed to prevent back flow from the arteries into the ventricles. Shortly thereafter, the tricuspid and mitral valves open (as FIG. 2 shows), to allow flow from the atria into the corresponding ventricles. Shortly after ventricular systole (i.e., ventricular emptying) begins, the tricuspid and mitral valves close (see FIG. 3)—to prevent back flow from the ventricles into the corresponding atria—and the aortic and pulmonary valves open—to permit discharge of blood into the arteries from the corresponding ventricles.

The heart valves are defined by fibrous rings of collagen, each called an annulus, which forms a part of the fibrous skeleton of the heart. The annulus provides attachments for the cusps or leaflets of the valves. In a healthy heart, muscles and their tendinous chords (chordae tendineae) support the valves, allowing the leaflets of the valves to open and close in accordance with their intended functions.

II. Heart Dysfunctions

Infection, myocardial infarction, atrial fibrillation, other diseases, or anatomic defects can adversely affect the normal synchronous pumping actions of the left and right sides of the heart and/or the operation of heart valves during the cardiac cycle.

For example, due to one or more of these causes, a heart chamber may become stretched and enlarged. This condition can lead to adverse consequences. For example, (1) due to its enlarged condition the heart must pump harder to move the blood, and/or too little blood may move from the heart to the rest of the body. Over time, other chambers of the heart may also become weaker. The stretching and enlargement of a heart chamber, e.g., in the left ventricle, can lead to a condition called congestive heart failure. If not treated, congestive heart failure can lead to pulmonary embolisms, circulatory shutdown, and death.

The enlargement of a heart chamber can also lead to the enlargement or stretching a heart valve annulus. Also, the stretching or tearing of the chords surrounding a heart valve, or other forms of muscle failure in this region, can also change the shape of a heart valve annulus, even when enlargement of a heart chamber is absent. When the heart valve annulus changes its shape, the valve leaflets can fail to coapt. An undesired back flow of blood can occur between an atrium and a ventricle (called regurgitation), or back flow between an artery and a ventricle can occur. Such dysfunctions can eventually also weaken the heart and can result in heart failure.

Anatomic defects, e.g., in the septum, can also lead to heart dysfunction. These defects can be congenital, or they can result from disease or injury.

III. Prior Treatment Modalities

Medications can be successful in treating heart dysfunctions. For chronic or acute dysfunction, however, surgery is often necessary. For congestive heart failure, a heart transplant may be required. Like invasive, open heart surgical approaches have been used to repair or replace a dysfunctional heart valves or to correct septal defects.

The need remains for simple, cost-effective, and less invasive devices, systems, and methods for treating heart conditions such as congestive heart failure and/or heart valve dysfunction and/or septal defects. A parallel need also remains for similarly treating other dysfunctions that arise from unintended shape changes in other body organs.

SUMMARY OF THE INVENTION

The invention provides devices, systems and methods that support tissue in a hollow body organ for the purpose of restoring or maintaining native function of the organ. The devices, systems, and methods do not require invasive, open surgical approaches to be implemented, but, instead, lend themselves to catheter-based, intra-vascular and/or percutaneous techniques.

One aspect of the invention provides systems and methods for supporting tissue within a hollow body organ. The systems and methods employ first and second implants that are coupled together. The first implant is sized and configured to penetrate a first region of tissue in the hollow body organ. The second implant is sized and configured to penetrate a second region of tissue in the hollow body organ spatially distinct from the first region. At least one tension element couples the first and second implants together, to apply tension to the first and second implants, and thereby draw tissue inward, supporting it. The supporting effect serves, e.g., to draw tissue surfaces together to reduce tissue volume within the hollow body organ, as well as resist subsequent enlargement of tissue volume. Desirably, the supporting effect does not interfere with contraction of the hollow body organ to a lesser tissue volume. However, if desired, this form of bracing can be achieved.

Another aspect of the invention provides systems and methods for forming a tissue fold within a hollow body organ. The systems and methods employ first and second implants. The implants are sized and configured to penetrate spatially distinct regions of tissue in the hollow body organ. At least one tension element couples the first and second implants together to apply tension on the first and second implants. The tension creates a tissue fold between the first and second implants. The tissue fold serves, e.g., to reduce internal tissue volume within the hollow body organ, as well as resist subsequent enlargement of tissue volume. Desirably, the tensioning does not interfere with contraction of the hollow body organ to a lesser tissue volume. However, if desired, this form of bracing can be achieved with tissue folding.

In one embodiment, the first and second implants are part of an array of implants that penetrates spatially distinct regions of tissue in the hollow body organ. In this embodiment, at least one tension element extends among the array of implants to apply tension between adjacent implants and thereby create a pattern of multiple tissue folds. The multiple tissue folds serve, e.g., to draw a circumferential region of tissue together, forming a closure or seal.

Another aspect of the invention provides systems and methods for supporting tissue in a hollow body organ. The systems and methods employ a prosthesis sized and configured for placement either within an interior of the hollow body organ or about an exterior of the hollow body organ to regulate a maximum size and/or shape of the hollow body organ. The systems and methods also employ at least one fastener to secure the prosthesis to tissue in the hollow body organ. In one embodiment, the fastener comprises a helical fastener.

Another aspect of the invention provides systems and methods for supporting tissue within a hollow body organ making use of an elongated implant. The elongated implant is sized and configured to penetrate tissue and extend along a curvilinear path within or partially within a tissue wall. The elongated implant regulates a maximum size and/or shape of the hollow body organ. In one embodiment, the elongated implant comprises a helical shape.

The systems and methods that embody all or some of the various aspects of the invention, as described, are well suited for use in, e.g., a heart. The systems and methods can be used to support tissue within a heart chamber, e.g., of congestive heart failure or other conditions in which the volume of the heart becomes enlarged. The systems and methods can be used to seal or close perforations, holes, or defects in tissue. The systems and methods can be used to close or seal atrial appendages or septal defects.

Other features and advantages of the invention shall be apparent based upon the accompanying description, drawings, and claims.

DESCRIPTION OF THE DRAWINGS

FIGS. 19A to 19F show various embodiments of a prothesis that can be installed in a hollow body organ to shape the organ and prevent its enlargement.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

The technology disclosed in this specification is divided for clarity of presentation into sections, as follows:

I. Implants for Externally Supporting Tissue in a Hollow Body Organ
  A. Overview
  B. Systems and Methods for Supporting Tissue in a Heart Chamber
  C. Systems and Methods to Support Tissue In or Near a Heart Valve Annulus
II. Implants for Creating Tissue Folds
  A. Overview
  B. Systems and Methods Defining Discrete Tissue Folds
    1. Tissue Folding with Overlaying Patch Component
  C. Systems and Methods Defining Patterns of Tissue Folds
    1. Overview
    2. Appendage Isolation and Sealing
    3. Closing Perforations, Holes, or Defects
III. Prostheses for Externally Supporting Tissue in a Hollow Body Organ
  A. Overview
  B. Systems and Methods for Supporting Tissue in a Heart Chamber
  C. Systems and Methods for Supporting Tissue In or Near a Heart Valve Annulus
IV. Implants for Internally Supporting Tissue in a Hollow Body Organ It should be appreciated that the technology described in a given section can be combined with technology described in another section, and that there are features that are common to all technology described herein.

I. Implants for Externally Supporting Tissue in a Hollow Body Organ

A. Overview

Figure 1:
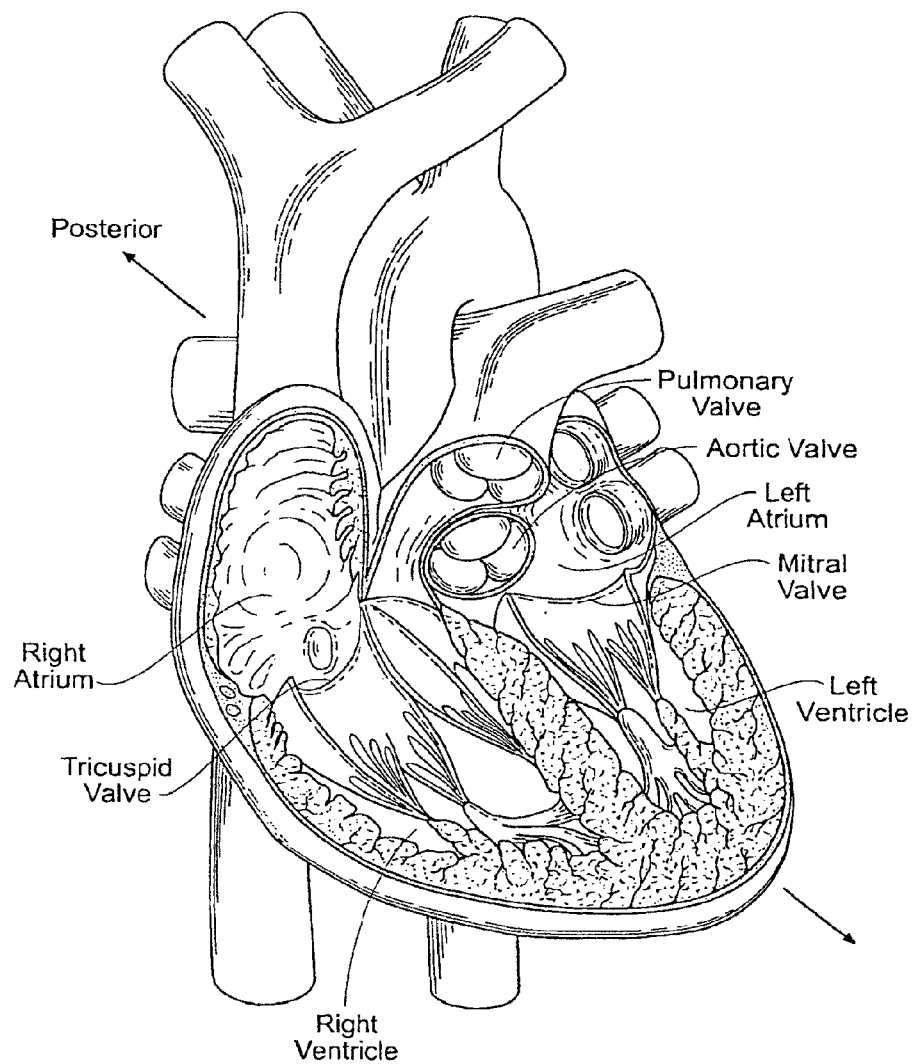
FIG. 1 is a perspective, anterior anatomic view of the interior of a healthy heart.
Figure 2:
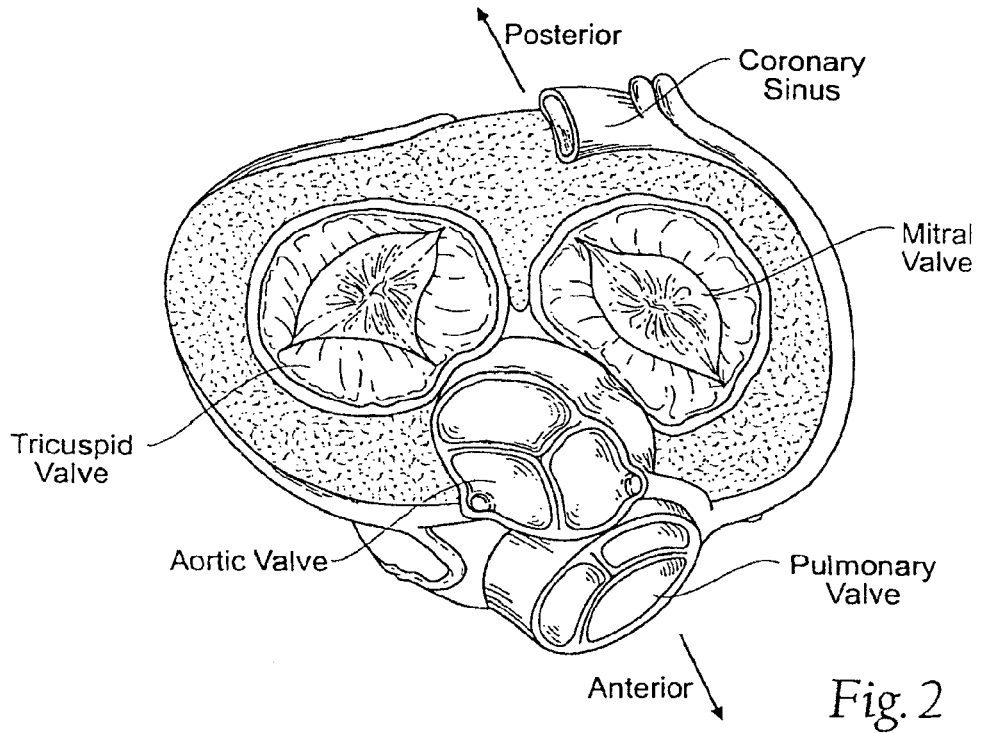
FIG. 2 is a superior anatomic view of the interior of a healthy heart, with the atria removed, showing the condition of the heart valves during ventricular diastole.
Figure 3:
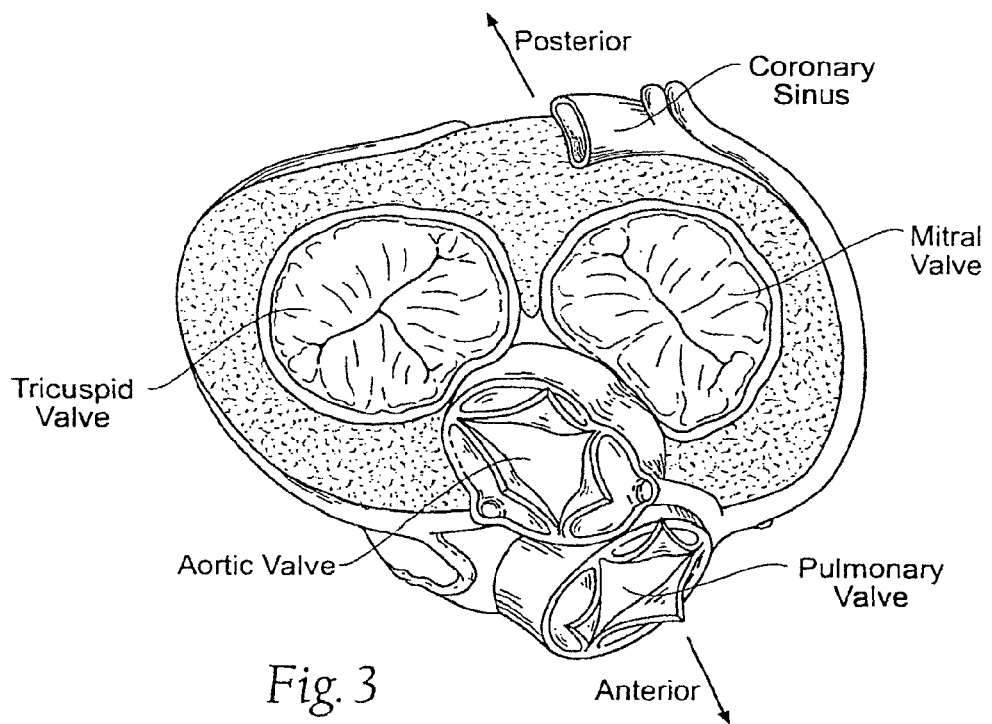
FIG. 3 is a superior anatomic view of the interior of a healthy heart, with the atria removed, showing the condition of the heart valves during ventricular systole.
Figures 4A, 4B:
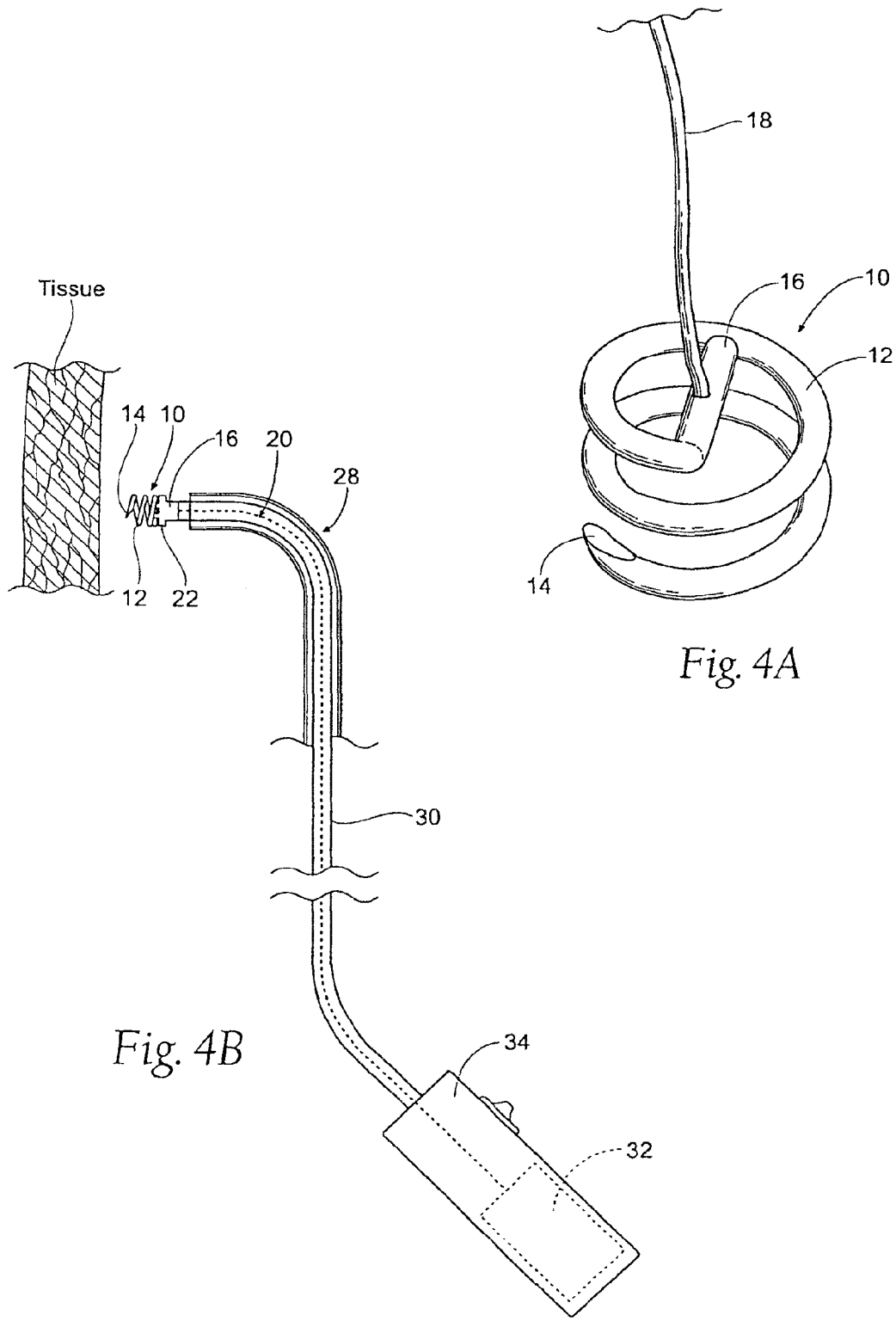
FIG. 4A is a perspective view of an implant for supporting tissue within a hollow body organ.
FIG. 4B is a side view of an applier instrument for implanting the implant shown in FIG. 4A in tissue.

FIG. 4A shows an implant 10 sized and configured for placement in a hollow body organ. The implant includes a body 12 that can be made from a formed plastic or metal or ceramic material suited for implantation in the body.

Figure 4C:
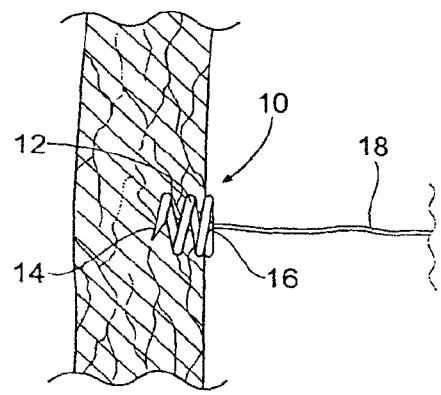
FIG. 4C is a side view of the implant shown in FIG. 4A after implantation in tissue.

The body 12 includes a distal region 14. The distal region 14 is sized and configured to penetrate tissue. The body 12 and its distal region 14 are sized and configured to take purchase in tissue (see FIG. 4C) sufficient to significantly resist release and/or migration of the body 12 from tissue, once implanted.

The body 12 also includes a proximal region 16. The proximal region 16 is sized and configured to engage an instrument or tool 20 (see FIG. 4B) that applies a force to cause the implant 10 to penetrate tissue.

As shown in FIG. 4A, the body 12 also includes a tether element 18. In the illustrated embodiment, the tether element 18 is carried on or near the proximal region 16 of the body 12. By virtue of this, when the body 12 is implanted in a tissue wall in a vessel or hollow body organ (see FIG. 4C), the tether element 16 extends outside the tissue wall.

The tether element 18 comprises a thread, braid, wire, or tube structure with a metallic or polymer material (e.g., polyester suture) having a break strength that is desirably at least equal to the resistance the distal region 14 of the body 12 has to release or migration from tissue. The tether element 18 is desirably flexible, to enable its deployment through an intravascular path. The tether element 18 is desirably not significantly elastic, but it can be, depending upon the tissue conditions encountered.

The tether element 18 is securely fastened to the proximal region 16, e.g., by soldering, gluing, riveting, or like attachment techniques. The junction between the tether element 18 and the body 12 desirably has a material strength that is greater than the material strength of the tether element 18 itself.

The body 12 of the implant 10 can take various forms. In the illustrated embodiment (as FIG. 4A shows), the body 12 comprises an open helical coil. In the arrangement, the distal region 14 comprises a sharpened leading tip. This type of body 12 and distal region 14 can be deployed into tissue by rotational movement, which the applier instrument 20 imparts to the implant 10.

Also, in the illustrated embodiment (as FIG. 4A shows), the proximal region 16 comprises an L-shaped leg. The L-shape leg desirably bisects the entire interior diameter of the coil body 12; that is, the L-shaped leg 16 extends completely across the interior diameter of the coil body 12. The L-shaped leg 16 serves as a stop to prevent the coil body 12, when rotated, from penetrating too far into tissue. Furthermore, as FIG. 4B generally shows, a rotatable implant drive mechanism 22 on the applier instrument 20 is sized and configured to engage the L-shaped leg 16 and impart rotation to the coil body 12 to achieve implantation in tissue.

Figure 5A:
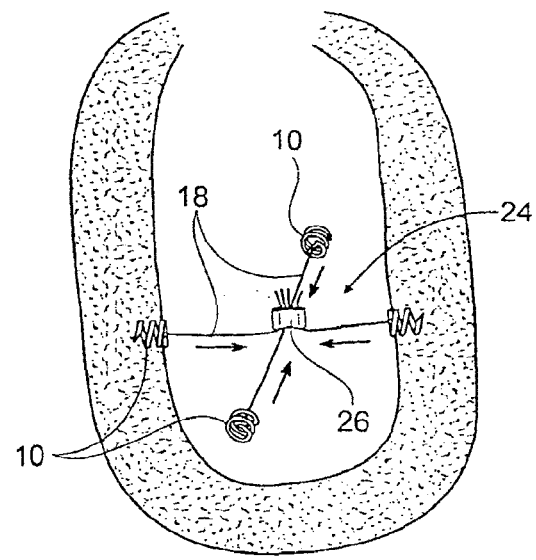
FIGS. 5A and 5B are tissue support systems established within a hollow body organ that comprises two or more of the implants as shown in FIG. 4A placed and maintained in tension by a clip element.
Figure 5B:
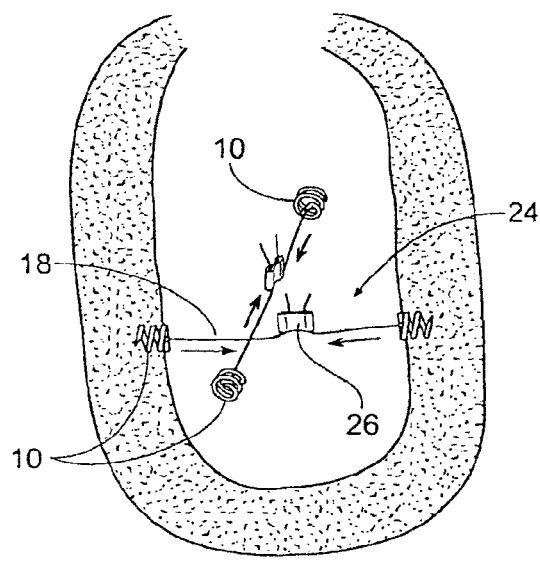

FIGS. 5A and 5B show a tissue shaping system 24 comprising at least two implants 10 shown in FIG. 4A. The implants 10 are implanted in a tissue wall within a hollow body organ or vessel (shown generically in FIGS. 5A and 5B) in a spaced-apart relationship or pattern. The number of tethered implants 10 deployed can vary according to the size and geometry of the targeted tissue volume, as well as the tissue support objectives.

The system 24 includes at least one clip element 26 joined to the tether elements 18 of the implants 10. FIG. 5A shows a single clip element 26. FIG. 5B shows multiple clip elements 26. The clip element or elements 26 mutually couple the tether elements 18 together, and allow tension to be applied and maintained external to the tissue, as the arrows in FIGS. 5A and 5B show. The tension individually applied and maintained by each tether element 18 on its respective implant 10, in combination, draws the surrounding tissue wall en masse inward toward the clip element 26, to shape the hollow body organ or vessel. Conversely, the tension applied and maintained by the tether elements 18 on each implant 10, in combination, resists movement of the tissue wall en masse outward away from the clip element 26. The tension prevents distension of tissue wall beyond the volume created by the tissue support system 24. The tissue support system 24, however, desirably does not interfere with contraction of the tissue wall toward a lesser volume.

The length of each individual tether element 18 and the magnitude of the tension it applies to its respective implant 10 collectively dictate a maximum shape for the body organ. In this way, the system 24 supports and shapes tissue in a body organ.

The system 24 as just described can be established in various parts of the body and for various therapeutic purposes. Two embodiments will be described for the purpose of illustration. The first embodiment is directed to the treatment and/or repair of congestive heart failure. The second embodiment is directed to heart valve remodeling.

B. Systems and Methods for Supporting Tissue in a Heart Chamber

Figure 6A:
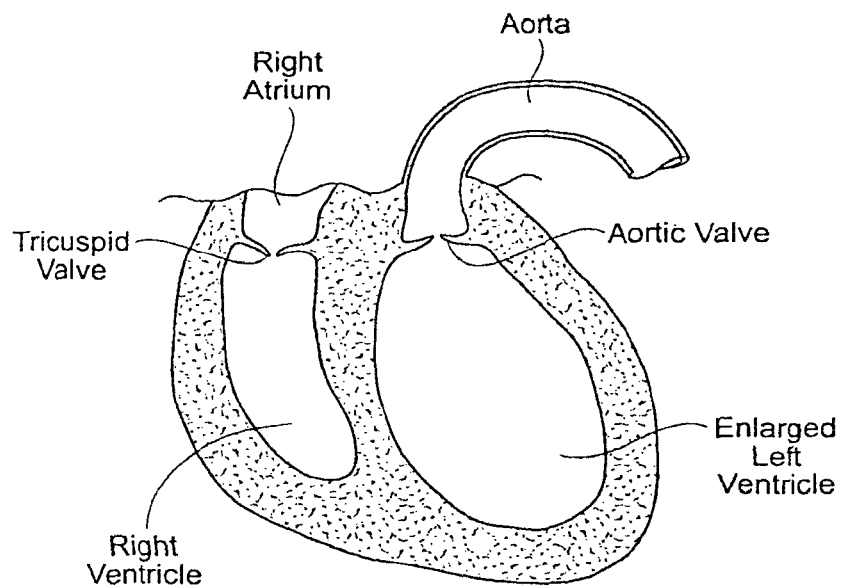
FIGS. 6A and 6B show the tissue supporting system shown in FIG. 5 established in a left ventricle of a heart, FIG. 6A showing the enlarged volume of the ventricle prior to establishment of the system, and FIG. 6B showing the system reducing the volume of ventricle.
Figure 6B:
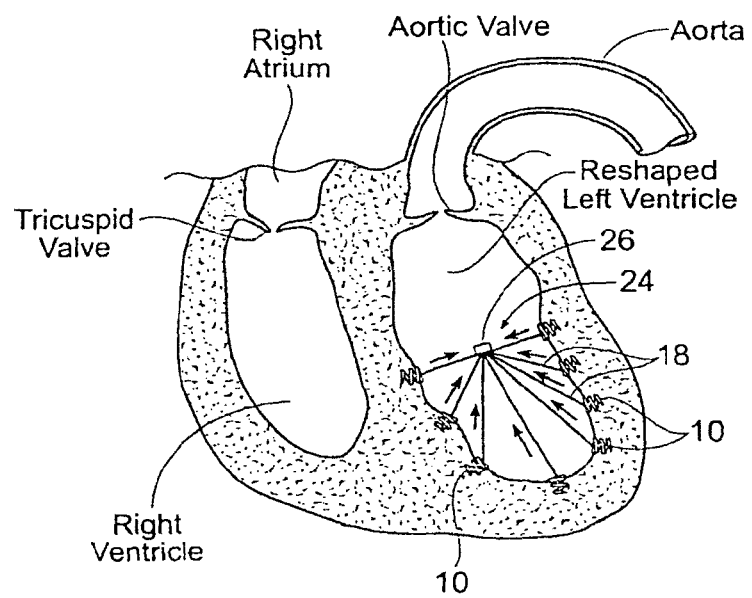

FIG. 6A shows a heart afflicted with congestive heart failure. The condition shown in FIG. 6A is characterized by an enlarged internal volume of the left ventricle. FIG. 6B shows the treatment and/or repair of the condition by the implantation of a system 24 of tethered implants 10 within the left ventricle. The tethers 18 of the implants 10 are placed and held in tension (shown by arrows in FIG. 6B) by a clip 26. Multiple clips 26 could be used, if desired. The tension applied by the system 24 shapes the left ventricle, pulling the chamber walls laterally closer together and thereby reducing the overall maximum internal volume. The tension prevents or restricts expansion of the left ventricle beyond the shape during ventricular diastole, which is better suited to efficient ventricular pumping. The support system 24, however, does not interfere with normal contraction of the left ventricle during ventricular systole.

FIGS. 7A to 7D show the intra-vascular deployment of the system 24 shown in FIG. 6B. Alternatively, the system can be established using conventional open heart surgical techniques or by thoracoscopic surgery techniques.

In the intra-vascular approach shown in FIGS. 7A to 7D, a guide component 28 is delivered over a guide wire (not shown) through the aortic valve into the left ventricle. The guide component 28 can be delivered through the vasculature under fluoroscopic guidance, e.g., through either a retrograde arterial route (via, e.g., the femoral artery or subclavian artery) (as shown) or an antegrade venous then trans-septal route.

Figure 7A:
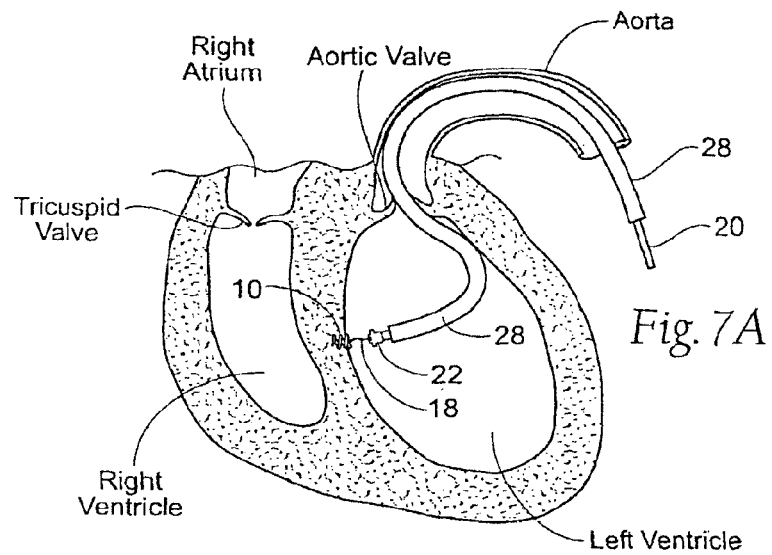
FIGS. 7A to 7D show the steps in establishing the system shown in FIG. 6B by use of intra-vascular tools and techniques.

The guide component 28 can comprise, e.g., a guide sheath that desirably has a steerable or deflectable distal tip. The guide wire can be withdrawn after the guide component 28 is deployed and positioned, so that the applier instrument 20 can be introduced through the guide component 28, as FIG. 7A shows. FIG. 4B also shows the deployment of the applier instrument 20 through the guide component 28.

In this arrangement (see FIG. 4B), the applier instrument 20 comprises a catheter 30 that carries an implant drive mechanism 22 on its distal tip. The drive mechanism 22 carries at least one tethered implant 10. An motor 32 in a handle 34, operated by the physician, drives the mechanism 22 to rotate the implant 10. As a result, the implant 10 is caused to penetrate the myocardium (as FIG. 7A shows).

The implantation force of the drive mechanism 22 is desirably resolved in some manner to provide positional stability and resist unintended movement of the drive mechanism 22 relative to the implantation site. A resolution force is desirably applied to counteract and/or oppose the implantation force of the drive mechanism 22. It is desirable to resolve some or all or a substantial portion of the implantation force within the vessel lumen (or other hollow body organ) itself, and preferably as close to the implantation site as possible.

The tubular body of the guide component 28 and/or the shaft of the applier instrument 20 can be sized and configured to possess sufficient column strength to resolve some or all or at least a portion of the implantation force within the vessel lumen or hollow body organ. FIG. 7A shows the guide component 28 braced against a wall of the ventricle to apply counterbalancing resolution force. In addition, or alternatively, the guide component 28 and/or the aopplier instrument 20 can include some form of stabilization means for applying a counteracting force at or near the drive mechanism 22. Various types of stabilization means are disclosed in co-pending U.S. patent application Ser. No. 10/669,881, filed Sep. 24, 2003, and entitled "Catheter-Based Fastener Implantation Apparatus and Methods with Implantation Force Resolution."

The guide component 28 is reposition in succession to other intended myocardial delivery sites. At each site, the applier instrument 20 is actuated to place an implant 10. In this way (see FIG. 7B), a desired spacing of implants 10 (such as a radial or spiral-like pattern) is distributed within the left ventricle.

Figure 7B:
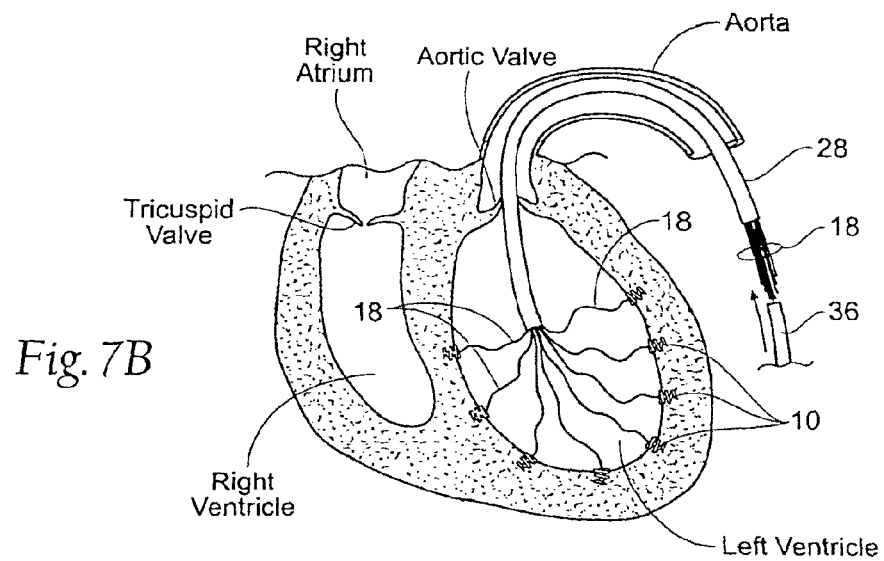

Once the desired number of implants 10 are deployed inside the left ventricle, the applier instrument 20 is withdrawn from the guide component 28. The tether elements 18 of the implants 10 are left gathered and channeled through the guide component 28, as FIG. 7B shows.

Figure 7C:
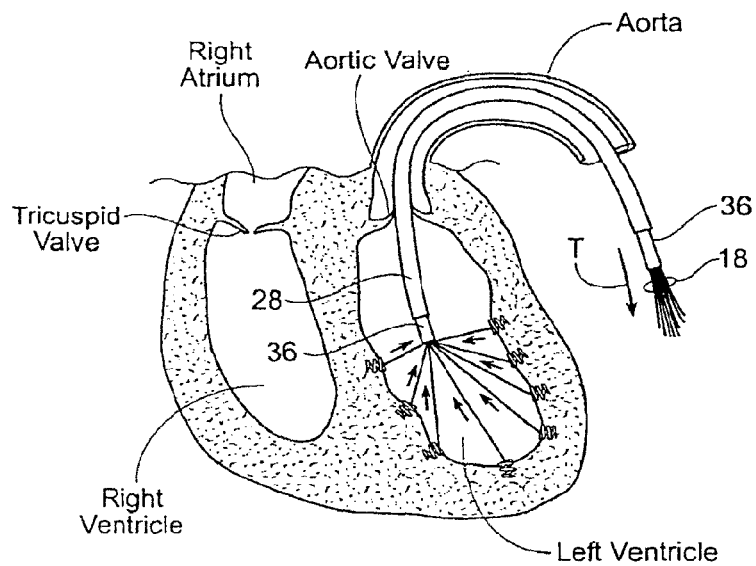

As FIG. 7C shows, a clip-applier instrument 36 is tracked through the guide component 28 and over the bundle of tether elements 18 into the left ventricle. The tether elements 18 act as a composite guide wire to guide the clip-applier instrument 36 into the left ventricle.

Figure 7D:
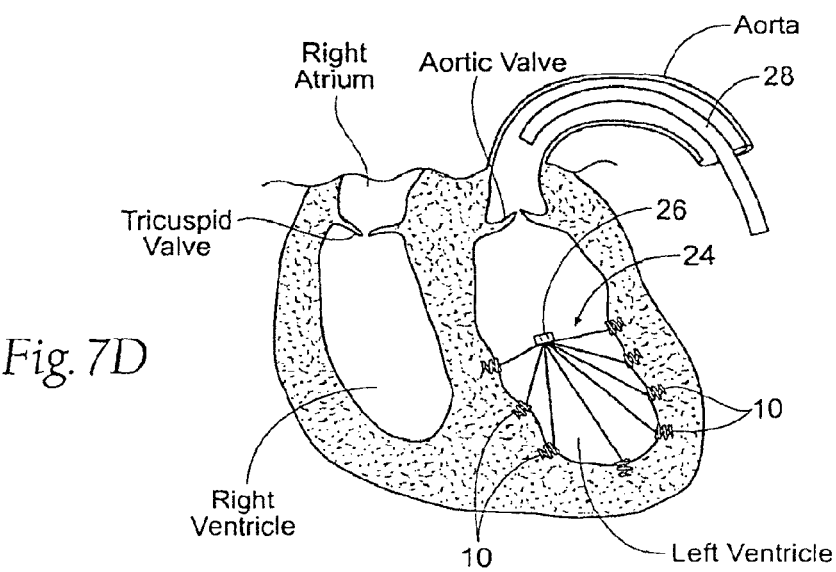

Once in the left ventricle, the clip-applier instrument 36 is held stationary, while the tether elements are pulled taut through the clip-applier instrument 36 (shown by arrow T is FIG. 7C). As the individual tether elements 18 grow taut, they apply tension on the individual implants 10, as FIG. 7C shows. This, in turn, pulls the walls of the left ventricle inward towards the clip-applier instrument 26 (as a comparison of the left ventricle shown in FIG. 7B to the left ventricle shown in FIG. 7C demonstrates). Once a desired ventricular volume is achieved (as determined, e.g., through fluoroscopy), the clip-applier instrument 36 applies a clip 26 to the tether elements, attaching the tether elements 18 together in tension (see FIG. 7D). The clip-applier 36 cuts the bundle of tether elements 18 proximal to the site where the clip 26 was applied. The clip-applier instrument 36 and loose tethers 18 are then withdrawn from the left ventricle through the guide component 28, and the guide component is withdrawn, as FIG. 7D shows.

The system 24 has been established to support the left ventricle to treat, in this instance, congestive heart failure.

It should be appreciated that one or more implants 10 of the system 24 can be electrically coupled to a device that can be operated to control muscular and/or electrical activity in heart tissue. Absent this intended effect, however, it is desired that the implants 10 are not inherently electrically conductive, so as not to interfere with electrical conduction within the heart.

C. Systems and Methods to Support Tissue at or Near a Heart Valve Annulus

Figure 8A:
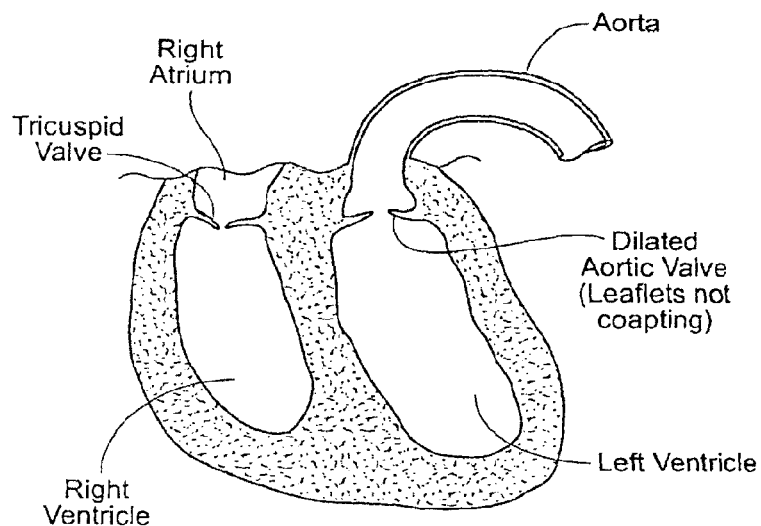
FIGS. 8A and 8B show a tissue supporting system like that shown in FIG. 5, established in a left ventricle of a heart in or near the annulus of the aortic valve, FIG. 8A showing the dilated condition of the aortic valve annulus prior to establishment of the system, and FIG. 8B showing the system reshaping the annulus to restore leaflet coaption.

FIG. 8A shows a heart afflicted with congestive heart failure. As shown in FIG. 8A this condition has resulted in an enlarged internal volume of the left ventricle, leading to a dilation or stretching the aortic heart valve annulus. As a result, the aortic valve leaflets do not properly coapt during ventricular systole. An undesired retrograde flow of blood from the left ventricle into the aorta can occur during ventricular systole.

Figure 8B:
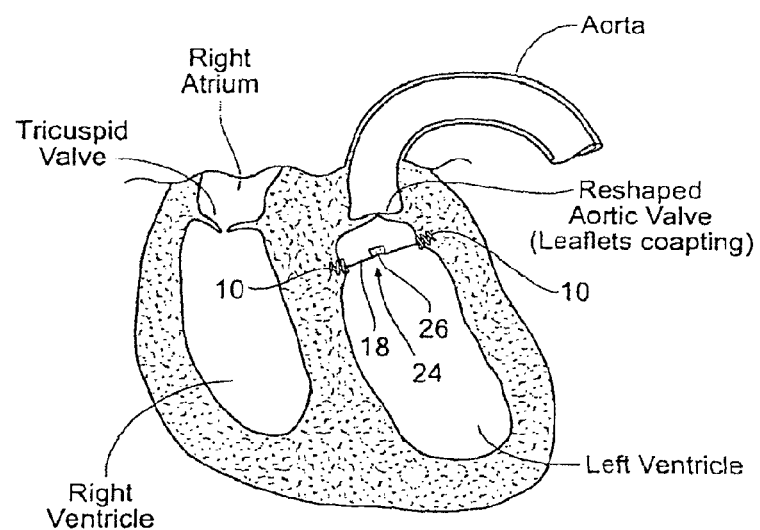

FIG. 8B shows the treatment and/or repair of this condition by the implantation of a system 24 of tethered implants 10 in the left ventricle near the aortic valve annulus. The tethers 18 of the fasteners are placed and held in tension (shown by arrows in FIG. 8B) by a clip 26. Multiple clips 26 can be used, if desired. The tension applied by the system 24 reshapes the aortic valve annulus, pulling the leaflets closer together, so that coaptation during ventricular systole occurs, and retrograde flow is prevented or reduced.

FIGS. 9A to 9D show the intra-vascular deployment of the system 24 shown in FIG. 8B. Alternatively, the system 24 can be established using conventional open heart surgical techniques or by thoracoscopic surgery techniques.

Figure 9A:
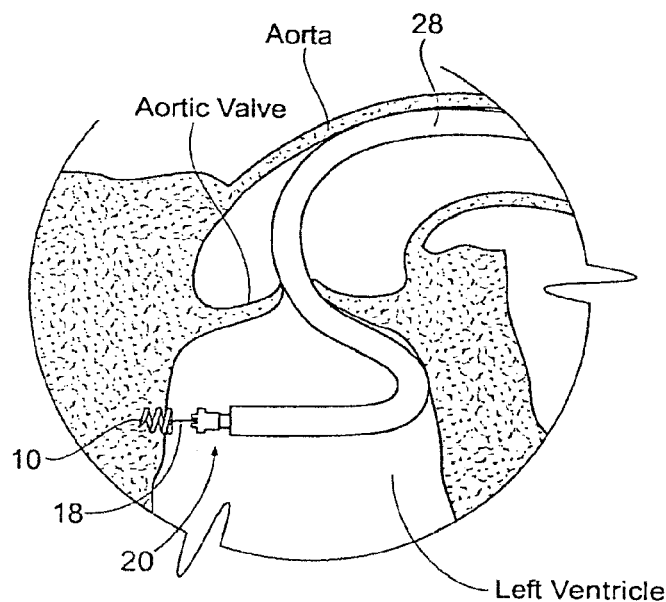
FIGS. 9A to 9D show the steps in establishing the system shown in FIG. 8B by use of intra-vascular tools and techniques.
Figure 9B:
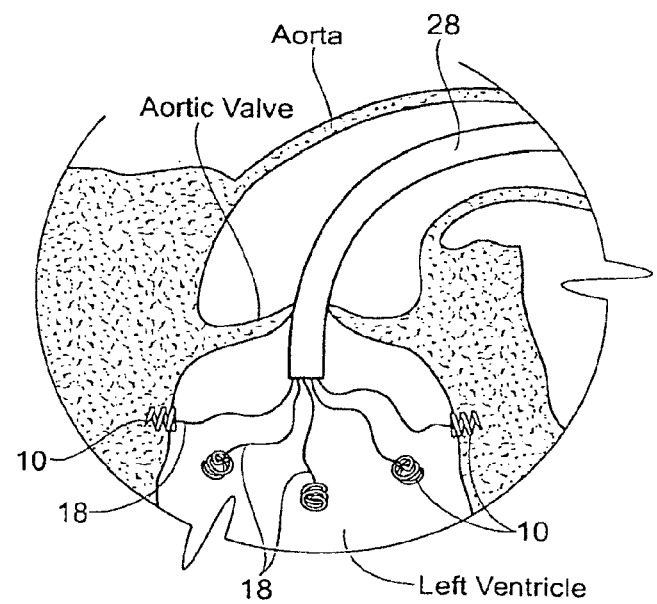

The intra-vascular approach shown in FIGS. 9A to 9D is the essentially the same as that shown in FIGS. 7A to 7D, previously described. Under fluoroscopic guidance, the guide component 28 is delivered over a guide wire through either the aortic valve (via, e.g., the femoral artery or subclavian artery) into the left ventricle at or near the inferior region of the aortic valve annulus or an antegrade venous then trans-septal route. The guide wire is withdrawn, and the applier instrument 20 is introduced through the guide component 28, as FIG. 9A shows.

The guide component 28 is positioned in succession at intended implant delivery sites at or near the inferior region of the aortic valve annulus. At each site, the applier instrument 20 is actuated to place an implant 10. FIG. 9A shows the guide component 28 braced against a wall of the ventricle to apply a counterbalancing resolution force to the implantation force. In this way (see FIG. 9B), a desired pattern of implants 10 is distributed at or near the inferior region of the aortic valve annulus. The tether elements of the implants 10 are gathered and channeled through the guide component 28 to outside the body.

Figure 9C:
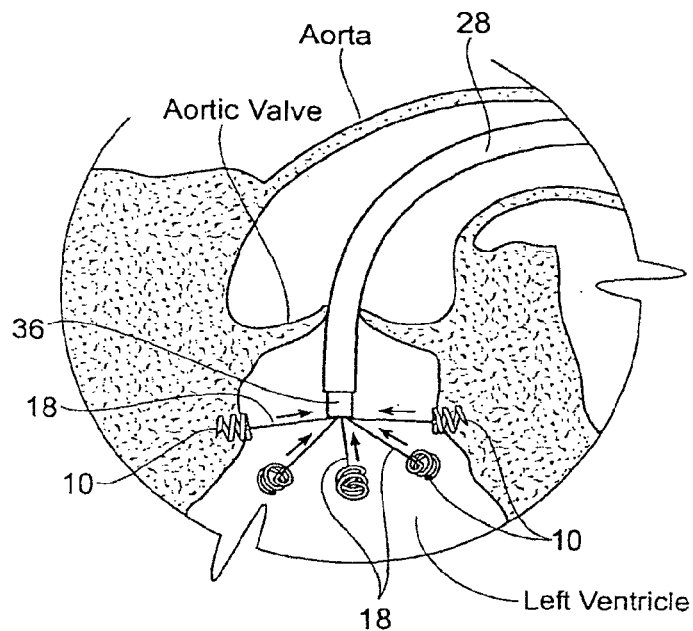

Once the desired number of implants 10 are deployed at or near the aortic valve annulus, the applier instrument 20 is withdrawn, and the clip-applier instrument 36 is tracked through the guide component 28 and over the bundle of tether elements 18 into the left ventricle (see FIG. 9C). The tether elements 18 act as guide wires to guide the clip-applier instrument 36 into the left ventricle.

Figure 9D:
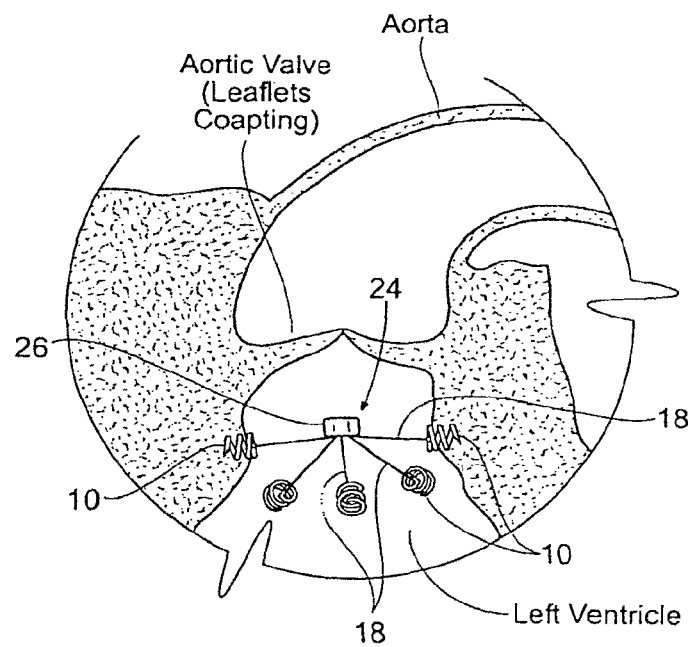

Once the clip-applier instrument 36 is in place, the tether elements 18 are pulled taut. Growing taut, the tether elements 18 apply tension on the individual implants 10, as the arrows in FIG. 9C show. This, in turn, pulls the walls of the left ventricle in the region of the aortic valve annulus inward towards the clip-applier instrument 36. The aortic valve leaflets are drawn closer together, into a geometry better suited for coaptation. The clip-applier instrument 36 applies a clip to the tether elements 18, attaching the tether elements together in tension (see FIG. 9D). The clip-applier 36 cuts the bundle of tether elements 18 proximal to the site where the clip 26 was applied, and the clip-applier instrument 36 and loose tethers 18 are withdrawn. The guide component is then withdrawn, as FIG. 9D shows.

The system 24 has been established to reshape the aortic valve annulus to treat, in this instance, congestive heart failure and/or retrograde flow through the aortic valve. The system 24 can also be used to treat retrograde flow through any other heart valve, e.g., the mitral valve.

It should be appreciated that one or more implants 10 of the system 24 can be electrically coupled to a device that can be operated to control muscular and/or electrical activity in heart tissue. Absent this intended effect, however, it is desired that the implants 10 are not inherently electrically conductive, so as not to interfere with electrical conduction within the heart.

II. Implants for Creating Tissue Folds

A. Overview

Figure 10A:
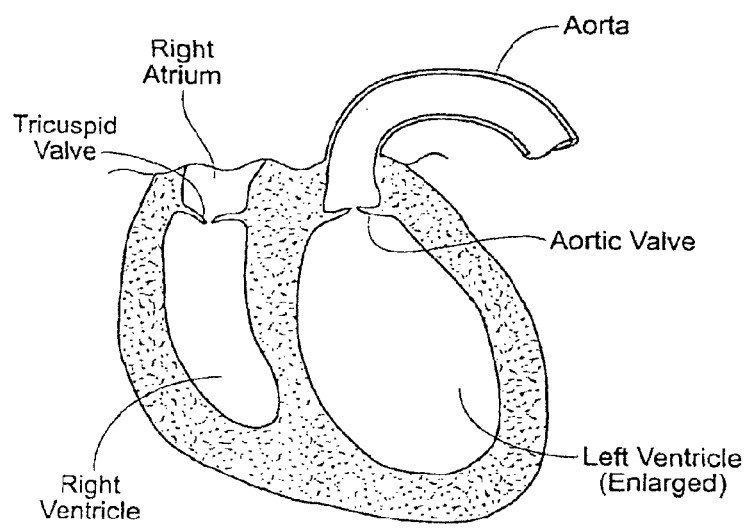
FIGS. 10A and 10B show a tissue folding system established in a left ventricle of a heart, FIG. 10A showing the enlarged volume of the ventricle prior to establishment of the system, and FIG. 10B showing the system reducing the volume of ventricle.
Figure 10B:
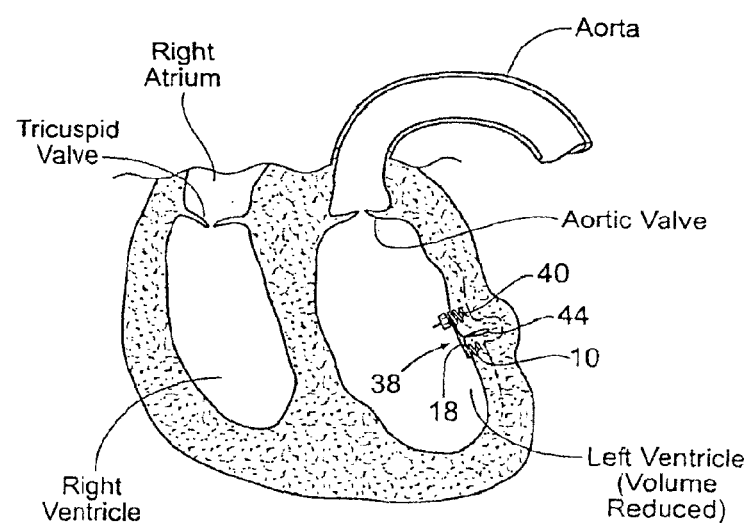

FIG. 10B shows a tissue folding system 38 comprising at least one tethered implant 10 shown in FIG. 4A. The implant 10 is used in combination with another implant 40, which can take the form of the implant shown in FIG. 4B, but need not include a tether element 18. The implants 10 and 40 are implanted in a tissue wall within a hollow body organ or vessel (shown to be within a left ventricle in FIG. 10B) in a spaced-apart relationship. The tether element 18 of the implant 10 is cinched through the implant 40 and held in tension by a clip element 42, to form a fold or tuck 44 in the tissue region between the implants 10 and 40. The presence of the fold 44 reduces the overall interior volume of the hollow body organ or vessel, as a comparison of the left ventricle shown in FIG. 10A—before establishment of the tissue folding system 38—and the left ventricle shown in FIG. 10B—after establishment of the tissue folding system 38—demonstrates. The number of implants 10 and 40 and resulting folds 44 formed can vary according to the size and geometry of the targeted tissue volume, as well as the volume reduction objectives.

The tissue folding system 38 as just described can be established in various parts of the body and for various therapeutic purposes.

B. Systems and Methods Defining Discrete Tissue Folds

The embodiment shown in FIG. 10B contemplates the establishment of one or more discrete folds 44, e.g., for the treatment and/or repair of congestive heart failure. The tissue folding system 38 can be implemented in various ways.

FIGS. 11A to 11D contemplate the intra-vascular deployment of the system 38 in a left ventricle, as generally shown in FIG. 10B. Alternatively, the system 28 can be established using conventional open heart surgical techniques or by thoracoscopic surgery techniques. The system 38 can be deployed in other hollow body organs or vessels within the body, either by open surgical techniques or intra-vascular access.

Figure 11A:
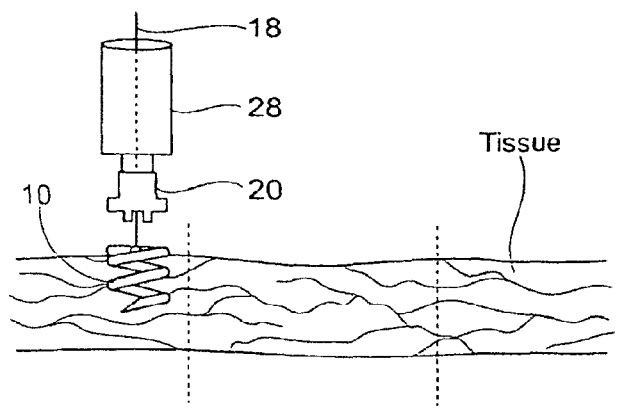
FIGS. 11A to 11D show the steps in establishing the system shown in FIG. 10B by use of intra-vascular tools and techniques.
Figure 11B:
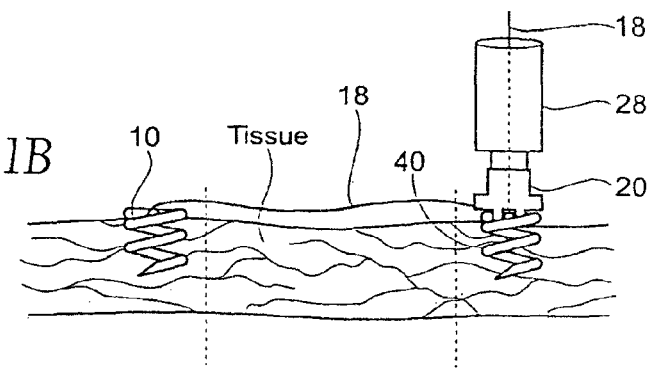

In the intra-vascular approach into the left ventricle, as shown in FIGS. 11A to 11D, an applier instrument 20 can be introduced through a guide component 28 through either the aorta in the manner shown in FIG. 7A (via, e.g., the femoral artery or subclavian artery) or an antegrade venous then trans-septal route. The applier instrument 20 deploys at least one tethered implant 10 (as FIG. 11A shows). The applier instrument 20 is withdrawn to receive the implant 40, and then redeployed to an adjacent tissue region, using the tether element 18 of the first implant 10 as a guide wire as FIG. 11B shows. The tether element 18 of the implant 10 is slidably trapped or otherwise threaded through the implant 40 as the implant 40 is deployed, as FIG. 11B also shows. The applier instrument 20 is withdrawn from the guide component 28, with the tether element 18 of the implant 10 channeled through the guide component 28.

Figure 11C:
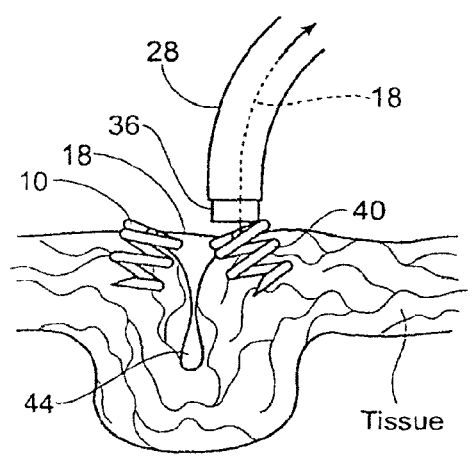
Figure 11D:
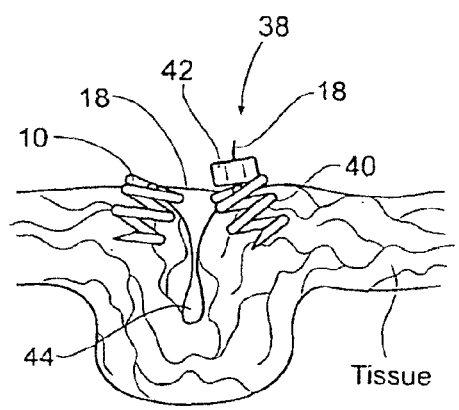

As FIG. 11C shows, a clip-applier instrument 36 is tracked through the guide component 28 and over the tether element 18 to the tissue site. The clip-applier instrument 36 is held stationary, while the tether element 18 is pulled taut through the clip-applier instrument 36 (see FIG. 11C). The tether element 18 applies tension between the implants 10 and 40, drawing the implants 10 and 40 together to cinch the intermediate tissue. The intermediate tissue folds it upon itself, and the fold 44 is created, as FIG. 11C shows. The clip-applier instrument 36 applies a clip element 42, to maintain tension and the resulting fold 44 (see FIG. 11D). The clip applier 36 cuts the tether element 18 proximal to the site where the clip 42 was applied. The clip-applier instrument 36 is then withdrawn through the guide component 28, and the guide component is withdrawn, as FIG. 11D shows.

Figure 12:
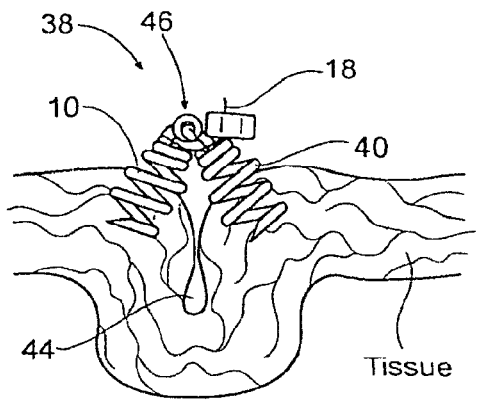
FIG. 12 shows another embodiment of a tissue folding system possessing the features of the system shown in FIG. 10B.

Alternatively, or in combination with the clip element 42, the implants 10 and 40 can include interlocking structural components 46 (see FIG. 12) that are brought into engagement by pulling the tether element 18 taut. In an alternative embodiment (not shown), a separate bridging element can be applied to interlock elements 10 and 40 after they are brought into close proximity by pulling the tether element taut. The engagement between the components 46 that holds the relative positions of the implants 10 and 40, to maintain the tissue tension and the resulting fold 44. In this arrangement, the implant 40 can be partially installed and tension applied to the tether element 18 to draw the implants 10 and 40 toward one another, to create the desired fold 44. Then installation of the implant 40 can be completed to bring the components 46 into interlocking engagement.

Figure 13A:
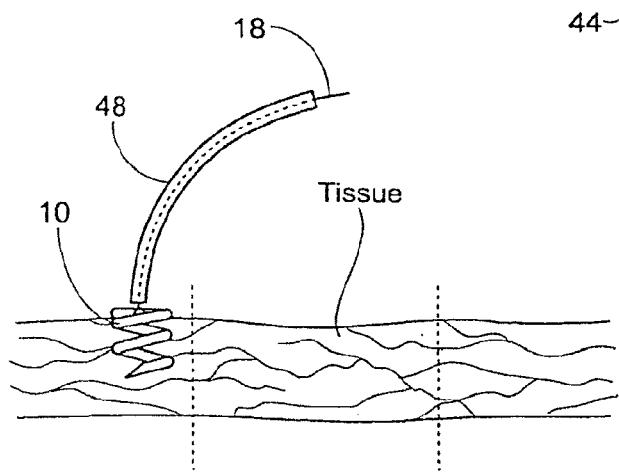
FIGS. 13A to 13C show the steps in establishing, by use of intra-vascular tools and techniques, another embodiment of a tissue folding system possessing the features of the system shown in FIG. 10B.
Figure 13B:
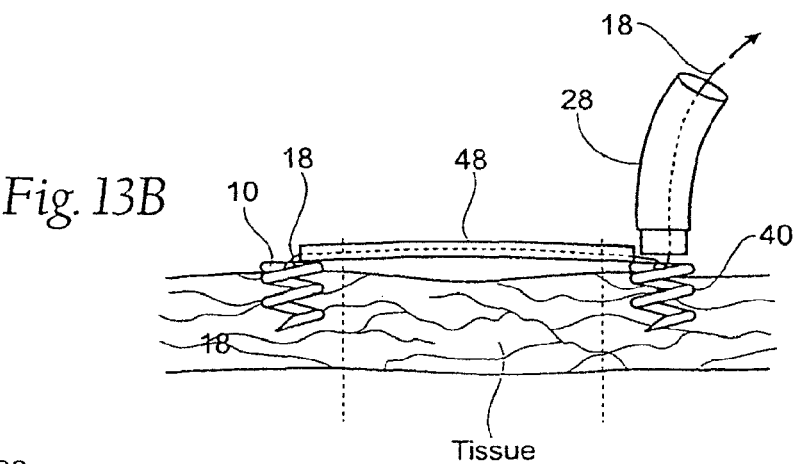
Figure 13C:
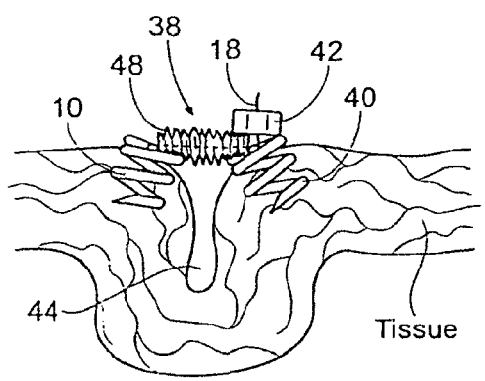

As shown in FIGS. 13A to 13C, the spacing between the implants 10 and 40, after tension is applied to the tether element 18, can be controlled by use of flexible, collapsible tube 48 between the implants 10 and 40. In this arrangement, the length of the tube 48, when collapsed, is predetermined to reflect the desired spacing between the implants 10 and 40 when in tension. As FIG. 13A shows, the tube 48 is guided in an uncollapsed condition over the tether element 18 after deployment of the implant 10. The implant 40 is deployed by the applier instrument 20 in the manner previously described, placing the tube 48 (uncollapsed) between the implants 10 and 40, as FIG. 13B shows. Subsequent use of the clip-applier instrument; as previously described, to draw the tether element 18 taut, collapses the tube 48 to until its predetermined length is assumed—resisting any further cinching—at which point the clip element 42 is applied, resulting in the system 38 shown in FIG. 13C. Alternatively, a non-collapsible tube could be used as a spacer between the two implants 10 and 40.

Figure 14A:
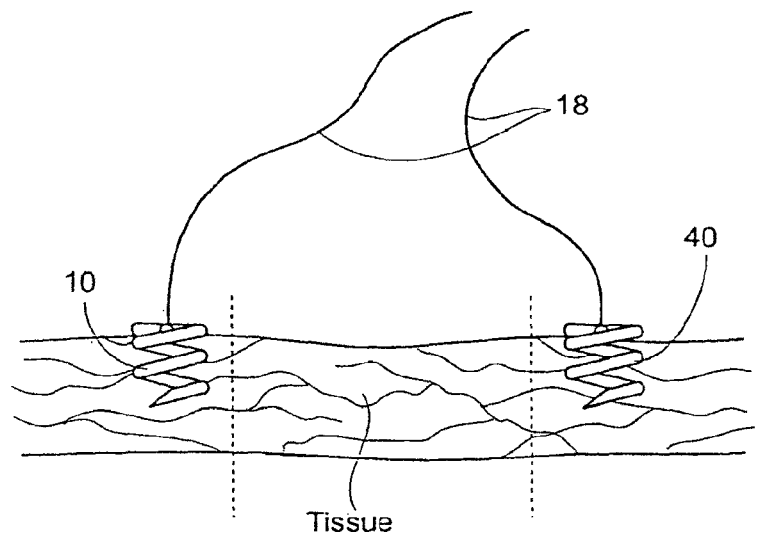
FIGS. 14A and 14B show the steps in establishing, by use of intra-vascular tools and techniques, another embodiment of a tissue folding system possessing the features of the system shown in FIG. 10B.
Figure 14B:
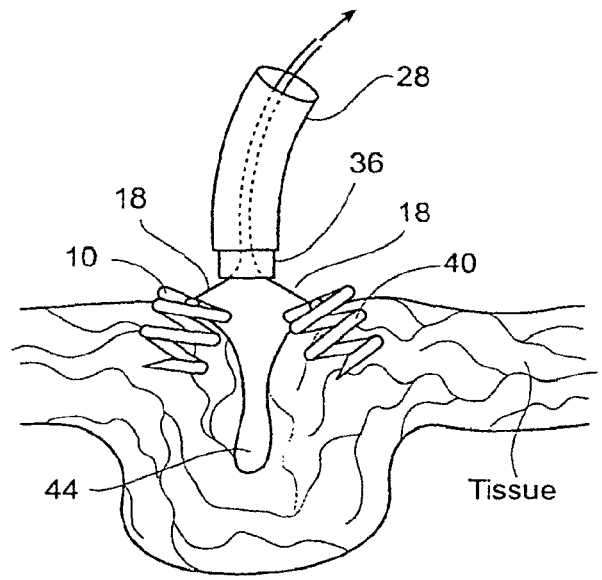

In the foregoing embodiments, a single tether element 18 has been used to apply tension between the implant 10 that carries the tether element 18 and another implant 40 that does not. Alternatively, as shown in FIGS. 14A and 14B, two implants 10, each with its own tether element 18 can be deployed. In this embodiment, the clip-applier instrument 36 is guided over both tether elements 18, so that tension can be applied individually to each tether element 18. The clip-applier instrument 36 draws the tether elements 18 taut (as FIG. 14B shows), creating the fold 44. The clip-applier instrument 36 then applies the clip element 42, to hold the two individual tether elements 18 in tension, forming the system 38.

In any of the foregoing manners, the system 38 can be established to reduce the interior volume of a heart chamber to treat, in this instance, a left ventricle affected by congestive heart failure.

The tether element(s) 18 may be elastic and/or possess a spring constant and/or be shaped and/or be otherwise compliant in the region between the implants 10 and 40. This material characteristic can help minimize or dampen peak load conditions upon the system 38, particularly when the tissue region is dynamic, as is the case with cardiac tissue.

1. Tissue Folding with Overlaying Patch Component

Figure 15A:
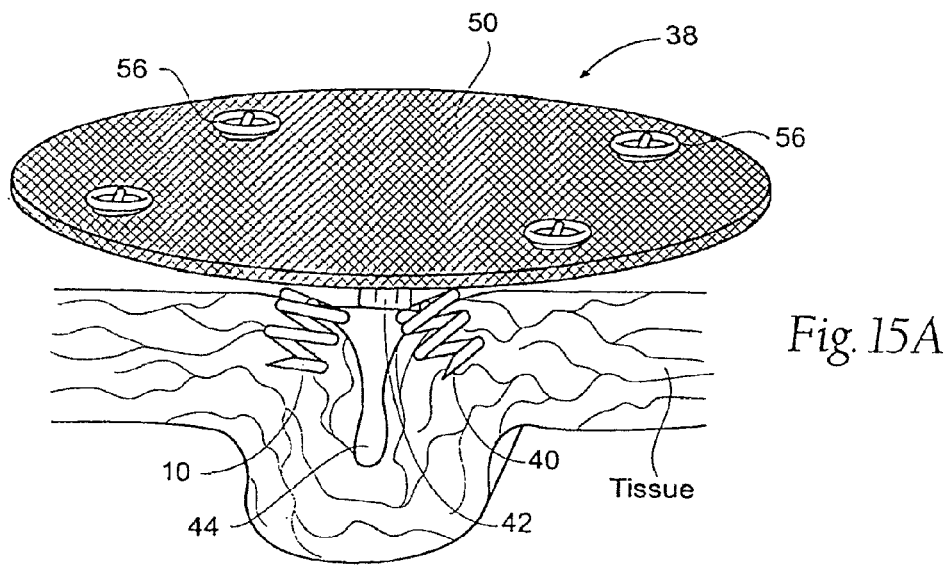
FIG. 15A is a tissue folding system as shown in FIG. 10B, with the including of an overlaying patch component that is secured by fasteners over the tissue fold established by the tissue folding system.

As shown in FIG. 15A, the tissue folding system 38 can include a patch component 50 secured by implants 56 to span the tissue fold 44. The patch component 50 distributes forces within the system 28 to maintain the fold 44.

The patch component 50, when installed, comprises a relatively planar frame, or a sheet of prosthetic material, or combinations thereof. The patch material is selected on the basis of its biocompatibility, durability, and flexible mechanical properties. The patch material can comprise a polymeric or metallic material, e.g., polyester, or ePTFE, or a malleable plastic or metal material, or a self-expanding plastic or metal material like Nitinol® wire. The patch material desirably possesses some elasticity, e.g., by using stretchable materials and/or weaves/knits, like Spandex™ material or elastic waist bands. The patch material also desirably possesses a resistance to expansion. The material may be drug coated or embedded with drugs, such as with heparin.

The patch component 50 is desirable sized and configured to permit non-invasive deployment of the prosthesis by an intra-vascular catheter. In this respect, the patch component 50 is desirably sized and configured to assume a compressed or collapsed, low profile condition, to permit its intra-vascular introduction into the hollow body organ by a catheter. The patch component 50 is likewise desirably sized and configured for expansion in situ from a collapsed condition into an expanded condition for contact with tissue overlaying the fold 44.

The patch component 50 carry radiopaque markers to help fluoroscopically position it. The markers can take the form, e.g. of marker bands, tight wound coils, or wire made from radiopaque materials such as platinum, platinum/iridium, or gold.

Figure 15B:
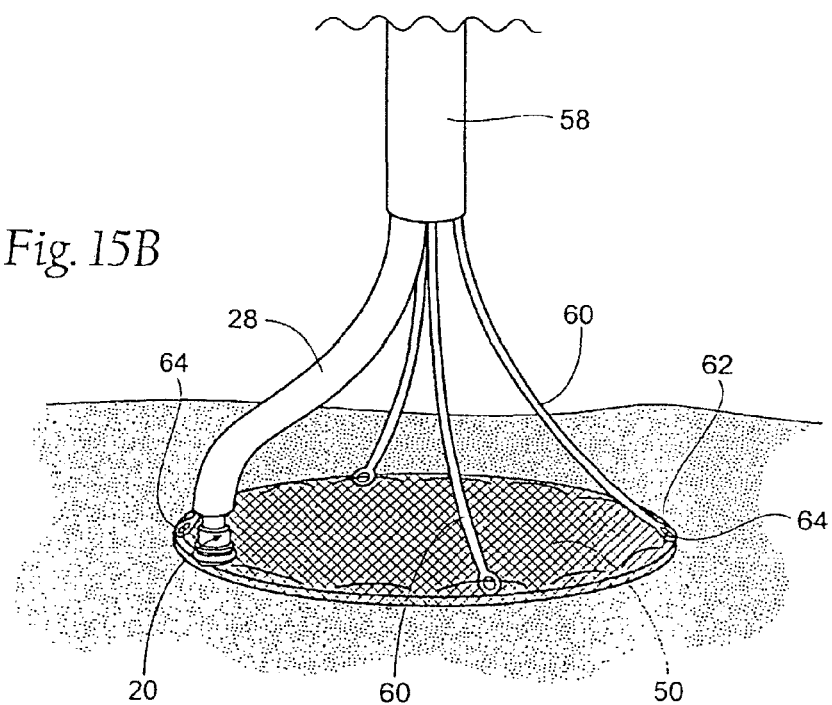
FIG. 15B is a catheter that deploys the patch component shown in FIG. 15A by intra-vascular access.

FIG. 15B shows a representative embodiment for delivering the patch component 50 by a catheter 58 deployed through intra-vascular access. The catheter 58 carries the patch component 50 in a collapsed condition. Once positioned over the site of the fold 44, the patch component 50 is released from the end of catheter 58 on outwardly tapered guide elements 60.

The guide elements 60 comprise wires with eyes 62. In the illustrated embodiment, the eyes 62 are secured to the patch component 50 by releasable suture 64. The suture 64 can, e.g., comprise a loop that is threaded through each eye 62 and the patch component 50. The ends of the suture loop extend out the proximal end of the catheter 58. Pulling on one end of the suture loop will withdraw the suture 64 from the eyes 62, thereby releasing the patch component 50.

The guide elements 60 (and/or the patch component 50 itself) are desirably biased to hold the patch component 50, once released, in an open and taut fashion, as FIG. 15B shows. The patch component 50 placed over the fold 44. The periphery of the patch component 50 is attached to tissue using the fasteners 56. As FIG. 15B shows, the applier instrument 20, previously described, may be deployed over the guide elements 60 to apply the fasteners 56 to the patch component 50. Alternatively, the applier instrument 29 may be deployed independent of the guide elements 60.

It should be appreciated that one or more implants 10 and/or 40 of the system 38, or the implants 56 associated with the patch component 50, can be electrically coupled to a device that can be operated to control muscular and/or electrical activity in heart tissue. Absent this intended effect, however, it is desired that the implants 10 and/or 40, or the patch component 50 are not inherently electrically conductive, so as not to interfere with electrical conduction within the heart.

C. Systems and Methods Defining Patterns of Tissue Folds

1. Overview

Figure 16A:
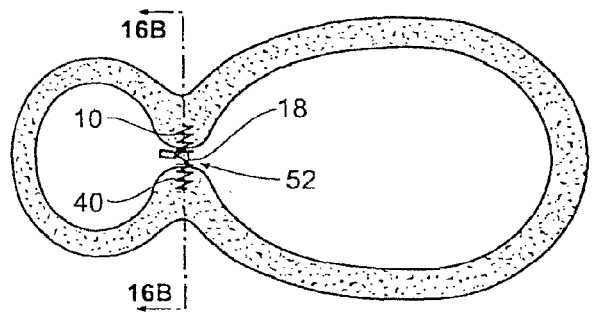
FIG. 16A shows the establishment of a system that creates a pattern of folds in a hollow body organ to isolate or seal one region of the hollow body organ from another region of the hollow body organ.
Figure 16B:
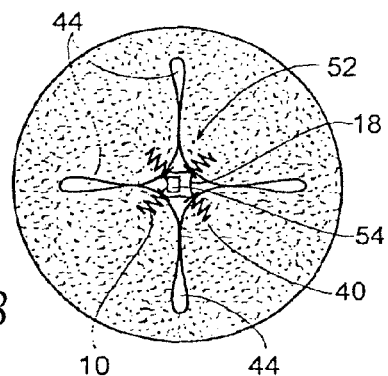
FIG. 16B is a plane view of the pattern of folds created by the system shown in FIG. 16A, taken generally along line 16B-16B in FIG. 16A.

As FIGS. 16A and 16B show, a tissue folding system 52 can comprise a plurality of folds 44 arranged in a pre-established pattern or array within a hollow body organ. The folds 44 are arranged in an annular pattern about the circumference of a tissue region. The folds 44 are formed by placement of at least one tethered implant 10 (as shown in FIG. 4A) in association with a plurality of other implants 40 (which need not be tethered). The tether element 18 cinches tissue between adjacent implants, and a clip element 54 holds tension in the tether element 18. As FIG. 16A shows, the resulting pattern of adjacent folds 44 creates a tissue region that is circumferentially drawn in, in purse string fashion. As FIG. 16B shows, the system 52 can be used to establish within a given hollow body organ a restriction that essentially isolates or seals one region of a hollow body from another region.

The system 52 as just described can be established in various parts of the body and for various therapeutic purposes. Two embodiments will be described for the purpose of illustration. The first embodiment is directed to isolation or sealing of an atrial appendage in the treatment of, e.g., atrial fibrillation. The second embodiment is directed to the repair of perforations, holes, or defects in tissue, e.g., atrial or ventricular septal defects.

2. Appendage Isolation/Sealing

Figure 17A:
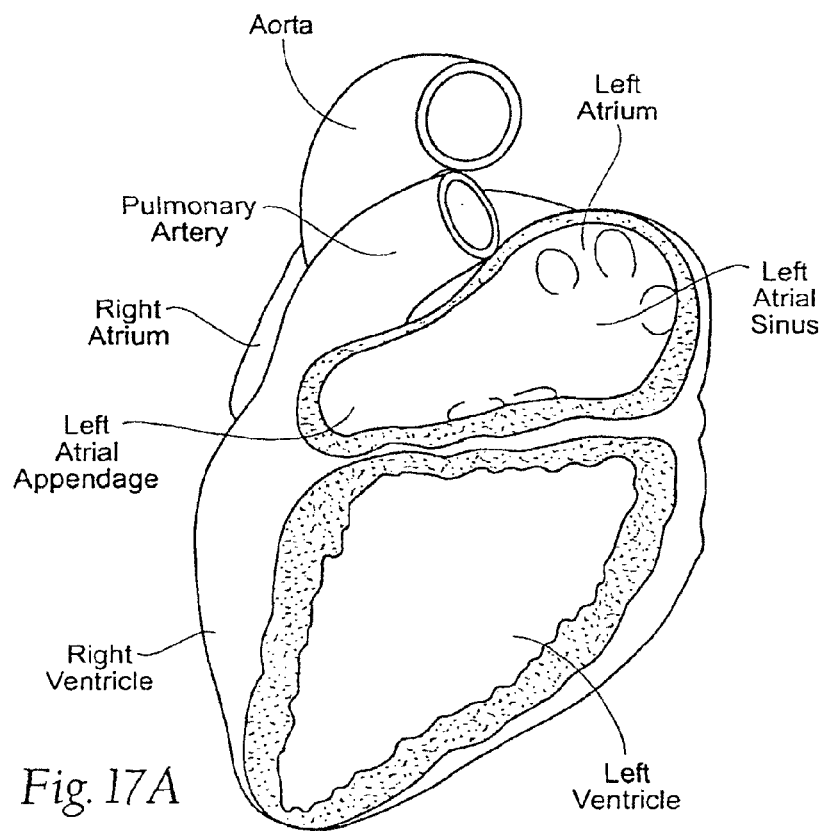
FIGS. 17A and 17B show the establishment of a pattern of multiple folds in the region between an atrial appendage and an atrial septum using the system shown in FIGS. 16A and 16B, FIG. 17A showing the atrium prior to establishment of the system, and FIG. 17B showing the atrium after establishment of the system to isolate and/or seal the atrial appendage from the atrial septum.
Figure 17B:
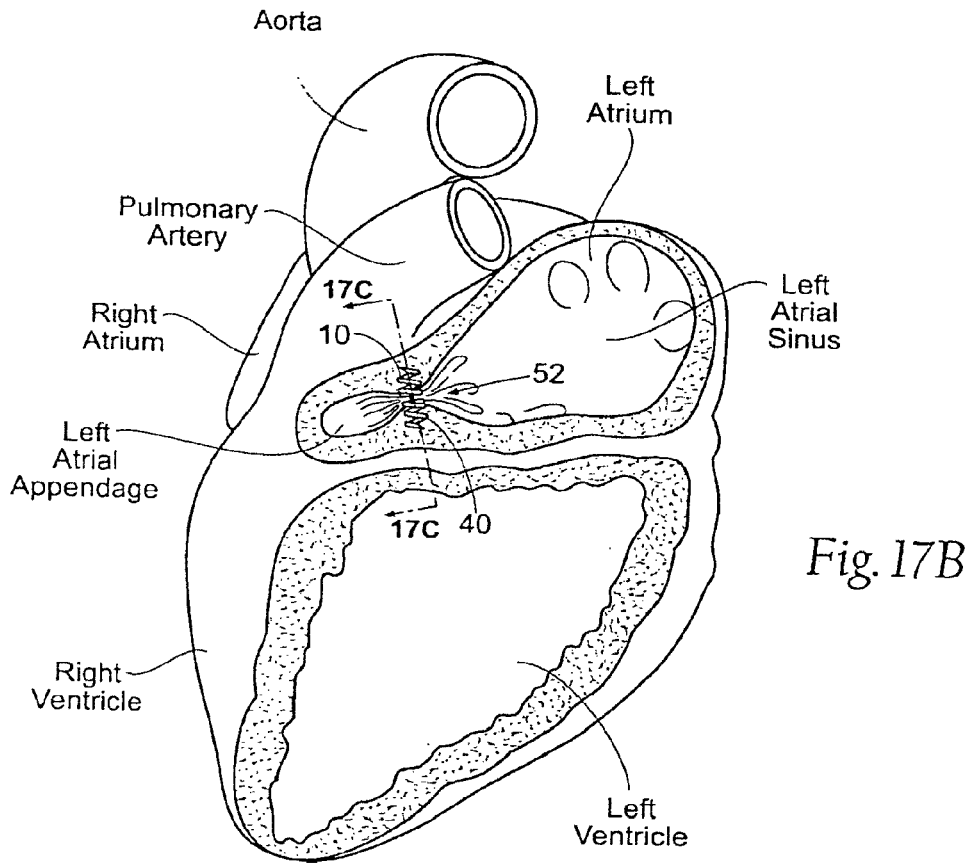

FIG. 17A shows for the purpose of illustration the two native anatomic parts of an atrium (here, the left atrium)—namely, the atrial appendage (also call the appendix auricilae) and the remainder of the atrium (also called the sinus). FIG. 17B shows a tissue folding system 52 that has been established within the atrium. The system 52 comprises a plurality of annular folds 44 (see FIG. 17C), which essentially isolates or seals the left atrial appendage from the atrial septum. In this arrangement, the system 52 can be used, e.g., to prevent the formation of blood stasis regions in an atrial appendage that is subject to dysfunction as a result of decreased contractility of the atrium following, e.g., treatment of atrial fibrillation.

Figure 17C:
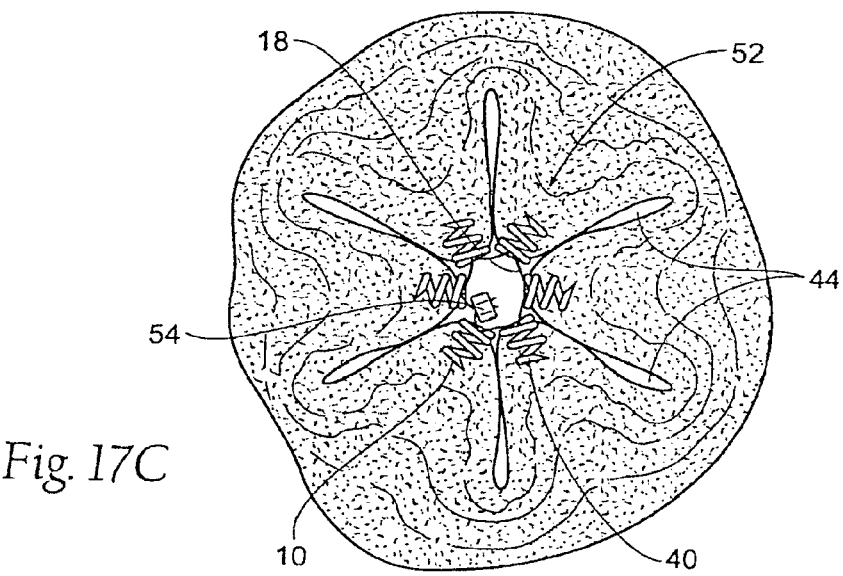
FIG. 17C is a plane view of the pattern of folds created by the system shown in FIG. 17B, taken generally along line 17C-17C in FIG. 17B.

As shown in FIGS. 17B and 17C, the system 52 comprises at least one tethered implant 10 used in association with a plurality of other implants 40 (which need not be tethered). The implants 10 and 40 are implanted at or near the relatively restricted, native junction between the atrial appendage and the atrial sinus. The implants 10 and 40 are implanted in a spaced-apart, annular relationship about the circumference of this junction.

The tether element 18 of the implant 10 is cinched through an adjacent implant 40, which, in turn, is cinched through the next adjacent implant 40, and so on. The cinching between adjacent implants creates a fold 44. The cinching between a sequence of adjacent annular implants creates a pattern of adjacent, folds 44 about the native junction.

The tether element 18—cinched sequentially about the implants 10 and 40—is held in tension by a clip element 54. The system 52 draws the junction together, thereby essentially closing the atrial appendage from blood flow communication with the remainder of the atrium. The number and pattern of implants 10 and 40 in the system 52 can vary according to the size and geometry of the targeted junction sought to be isolated and sealed.

The system 52 can be deployed to seal or otherwise isolate an atrial appendage, either by open surgical techniques or intra-vascular access, using the instruments and methodologies that have been previously described.

It should be appreciated that a patch component 50 like that shown in FIG. 15A could be deployed over a pattern of folds 44 formed by the system 52. It should also be appreciated that one or more implants 10 and/or 40 of the system 52 can be electrically coupled to a device that can be operated to control muscular and/or electrical activity in heart tissue. Absent this intended effect, however, it is desired that the implants 10 and/or 40 are not inherently electrically conductive, so as not to interfere with electrical conduction within the heart.

3. Closing Perforations, Holes, or Defects

Figure 18A:
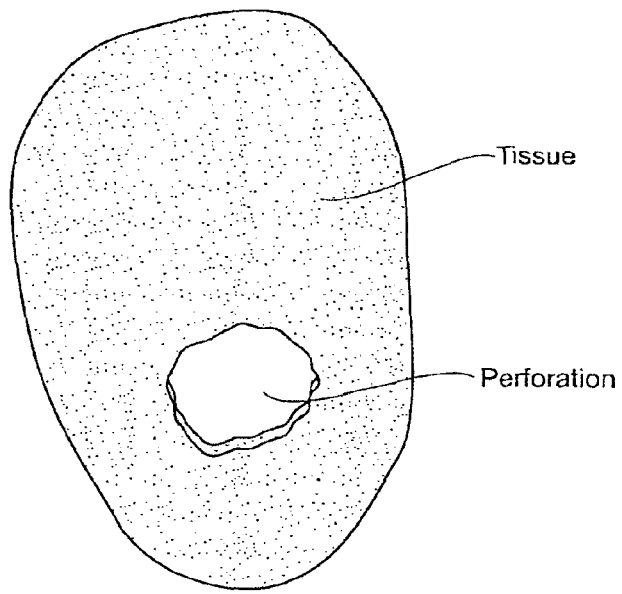
FIGS. 18A and 18B show the establishment of a pattern of multiple folds to seal a perforation in a hollow body organ using the system shown in FIGS. 16A and 16B, FIG. 18A showing the perforation prior to establishment of the system, and FIG. 18B showing the closing of the perforation after establishment of the system.
Figure 18B:
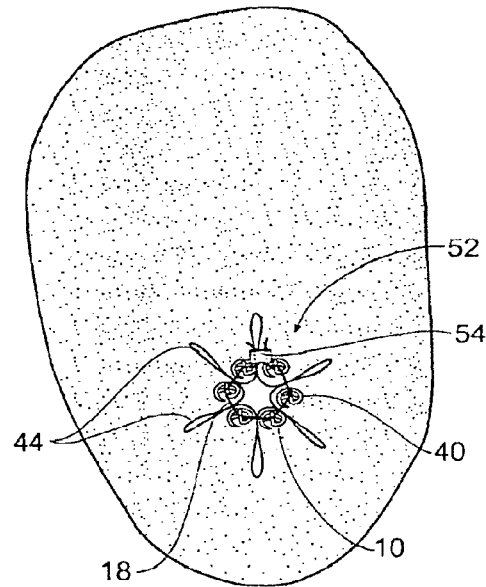

FIG. 18A shows for the purpose of illustration a tissue region that has a perforation caused, e.g., by disease, injury, or genetic defect. FIG. 18B shows a tissue folding system 52 established at or near the perforation in the tissue region. The system 52 comprises a plurality of annular folds 44, which essentially draw tissue together in a purse-string effect to close the perforation. The system 52 can be used, e.g., to seal septal defects in the atrium or ventricle, or in other regions of the body where perforations, holes, or defects occur.

The system 52 shown in FIG. 18B is essentially the same as shown 52 in FIGS. 17B and 17C. The system 52 comprises at least one tethered implant 10 in association with a plurality of other implants 40. The implants 10 and 40 are implanted in a spaced-apart, circumferential relationship about the perforation. The tether element 18 of the implant 10 is cinched through an adjacent implant 40, which, in turn, is cinched through the next adjacent implant 40, and so on, creating a pattern of adjacent, folds 44 about the perforation. The tether element 18—cinched sequentially about the implants 10 and 40—is held in tension by a clip element 54. The system 52 draws tissue surrounding the perforation together, thereby closing it, or at least reducing its native diameter.

The number and pattern of implants 10 and 40 in the system 52 can vary according to the size and geometry of the targeted junction sought to be isolated and sealed. Furthermore, the system 52 can be deployed to seal a perforation, hole of defect in tissue either by open surgical techniques or intra-vascular access, using the instruments and methodologies previously described.

It should be appreciated that, given the dimensions of the perforation, hole, or defect, a discrete system 38 like that shown in FIG. 10B could be used to draw tissue together in the region of the perforation, thereby repairing it. It should also be appreciated that a patch component 50 like that shown in FIG. 15A can be deployed over a tissue site repaired by the system 52 or 58.

In one embodiment (see FIG. 28), the patch component 50 can be sized and configured to cover a discrete perforation, such as a septal defect in the heart, without association with a tissue folding system 52 or 58. In this arrangement (see FIG. 28), the patch component 50 includes, e.g., a body portion 66 and a stem portion 68. The stem portion 68, in use, occupies the perforation, hole, or defect (e.g., as shown in FIGS. 29A and 29B), to plug the site. The body portion 66 extends like "wings" from the stem portion 68 to contact and seat against wall tissue adjacent the site.

Figure 28:
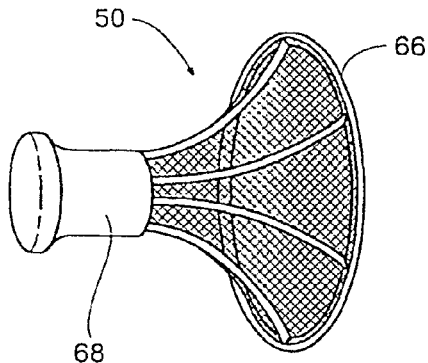
FIG. 28 shows a patch component having the features of the patch component shown in FIG. 15A, being sized and configured for repairing a septal defect in a heart.
Figure 29A:
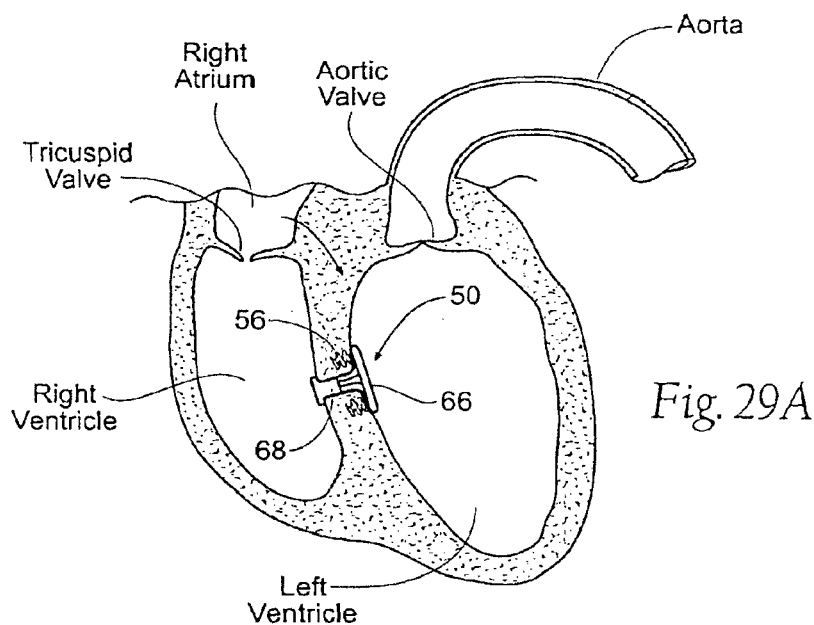
FIGS. 29A and 29B show the patch component shown in FIG. 28 installed in a septal defect between the left and right ventricles of heart.
Figure 29B:
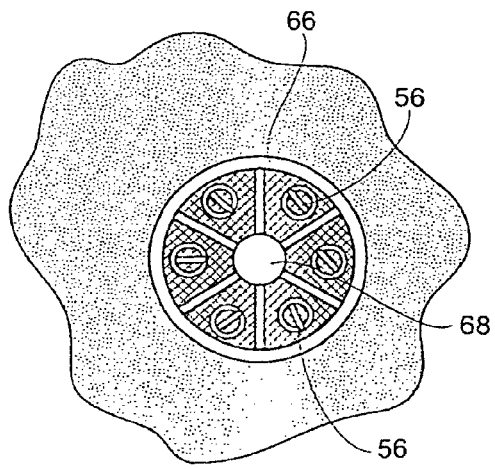

FIGS. 29A and 29B show the patch component 50 shown in FIG. 28 installed to cover a septal defect between the left and right ventricles of a heart. As FIGS. 29A and 29B show, fasteners 56 are desirably applied to anchor the body portion 66 to adjacent wall tissue. The patch component 50 shown in FIGS. 29A and 29B can be deployed to seal a perforation, hole of defect in tissue either by open surgical techniques or intra-vascular access, using the instruments and methodologies previously described.

In the foregoing indications in the heart, it is desired that the implants 10 and/or 40, and the patch component 50 and its associated fasteners 56, are not inherently electrically conductive, so as not to interfere with electrical conduction within the heart.

III. Prostheses for Externally Supporting Tissue in a Hollow Body Organ

A. Overview

Figure 20A:
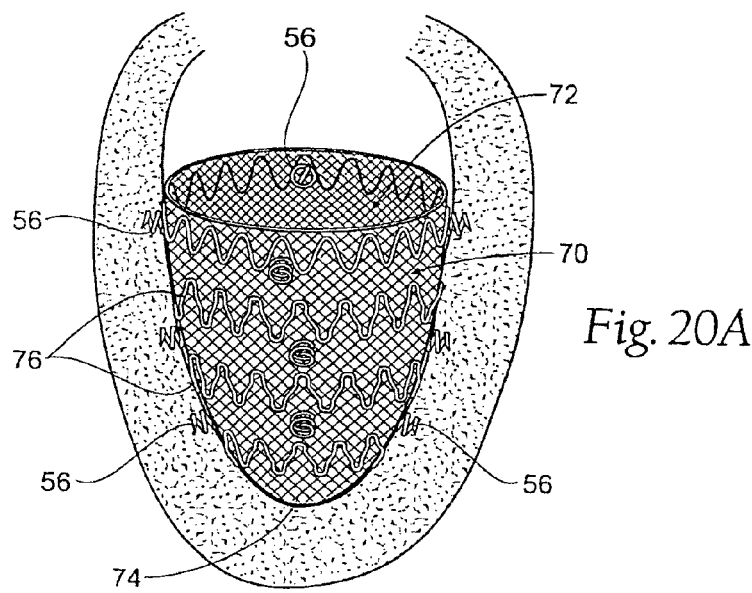
FIG. 20A shows a prosthesis of a type shown in FIGS. 19A to 19F installed in the interior of a hollow body organ.
Figure 20B:
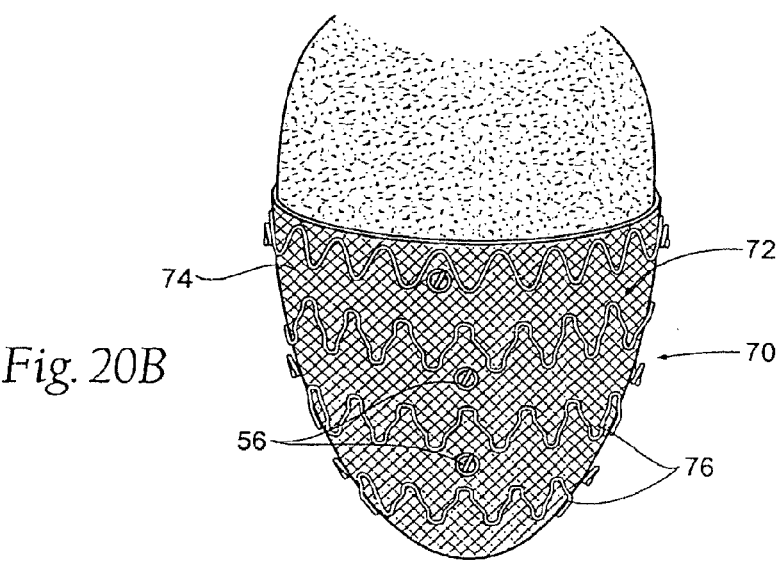
FIG. 20B shows a prosthesis of a type shown in FIGS. 19A to 19F installed about the exterior of a hollow body organ.

FIGS. 19A to 19F show various illustrative embodiments of a prosthesis 70 that is sized and configured for placement within an interior of a hollow body organ or around the exterior of a hollow body organ (see, e.g., FIGS. 20A and 20B, respectively). The prosthesis 70 has a body 72 that is preformed in a desired size and shape based upon the anatomy and morphology of the hollow body organ. When placed in or around a hollow body organ, the size and shape of the prosthesis body 72 constrains tissue, to regulate the maximum size and shape of the hollow body organ in a way that achieves a desired therapeutic result. However, the prosthesis body 72 desirably does not interfere with contraction of the hollow body organ to a lesser size and shape.

The body 72 can comprise a fully formed, three dimensional structure, as FIGS. 19A to 19D show. Alternatively, the body 72 can comprise component parts (A, B, C), as FIG. 19E shows, that are assembled in situ to form a composite body structure. The component parts A, B, and C may be assembled end-to-end in an adjacent relationship, or the component parts A, B, and C can be assembled in an overlapping relationship. In FIG. 19E, the component parts A, B, C comprise hoops, bowls, or truncated cylinders, which are assembled axially. Alternatively, as will be described in greater detail later, the components could comprise patch components (like that shown in FIG. 15A) that are assembled together, either end-to-end or in an overlaying relationship. Still alternatively, the body 72 can comprise a sheet-like structure, as shown in FIG. 19F, that is wrapped in situ to form a composite, three dimensional body structure. The body 72 could also include components that are coupled together with interconnecting hinges or springs. It should be appreciated that a multitude of structural configurations are possible.

In the illustrated embodiments, the body 72 is shown to include a prosthetic material 74. The prosthetic material 14 is selected on the basis of its biocompatibility, durability, and flexible mechanical properties. The material 74 can comprise, e.g., woven polyester or ePTFE. The prosthetic material 74 desirably possesses some elasticity, e.g., by using stretchable materials and/or weaves/knits, like Spandex™ material or elastic waist bands. The prosthetic material 74 also desirably possesses limited expansion or a resistance to expansion that can increase rapidly. The prosthetic material 74 may be drug coated or embedded with drugs on the inside surface, such as with heparin. Alternatively, the prosthetic material 74 may be relatively non-compliant, but can be compressed along with the rest of the prosthesis by crumpling, folding, etc. The prosthetic material 74 could also comprise a polymeric or metallic grid structure.

In the illustrated embodiments, the prosthetic material 74 is shown to be supported by a scaffold-like structure 76. It should be appreciated, however, that the prosthetic material 74 could be free of a scaffold-like structure 76, or, conversely, the scaffold-like structure 76 could be free of a prosthetic material 74.

The prosthetic material 74 and/or scaffold-like structure 76 are desirable sized and configured to permit non-invasive deployment of the prosthesis by an intra-vascular catheter. With this criteria in mind, the prosthetic material 74 and/or scaffold-like structure 76 are sized and configured to assume a compressed or collapsed, low profile condition, to permit their intra-vascular introduction into the hollow body organ by a catheter. Also with this criteria in mind, the prosthetic material 74 and/or scaffold-like structure 76 are sized and configured for expansion in situ from a collapsed condition into an expanded condition in contact with tissue in the targeted region.

In this respect, the scaffold-like structure 76, if present, can comprise, e.g., a malleable plastic or metal material that expands in the presence of an applied force. In this arrangement, the deployment catheter can include, e.g., an expandable body, such as a balloon, to apply the expansion force to the scaffold-like structure 76 in situ. Alternatively, the scaffold-like structure 76, if present, can comprise a self-expanding plastic or metal material (e.g., from Nitinol® wire) that can be compressed in the presence of a force, but self-expands upon removal of the compressive force. In this arrangement, the deployment catheter can include, e.g., a sleeve that can be manipulated to enclosed the scaffold-like structure 76 in a collapsed condition, thereby applying the compressive force, and to release the scaffold-like structure 76 when desired to allow the scaffold-like structure 76 to self-expand in situ.

The scaffold-like structure 76 can take various alternative forms, some of which are shown for the purpose of illustration. The scaffold-like structure 76 can include longitudinally extending spines, which form an umbrella-like structure shown in FIG. 19A. Alternatively, the scaffold-like structure 76 can comprise zigzag type stent rings (FIG. 19B), which can be independent or interconnected one with the other, or combinations thereof; or a helically wound stent support (FIG. 19C); or a woven or crisscrossing pattern. The scaffold-like structure 76 need not be present throughout the body 72; that is, the body 72 may include regions that include a scaffold-like structure 76 and regions that do not. The scaffold-like structure 76 can be, e.g., sewn onto prosthetic material 74. Other attachment means could be utilized to secure the scaffold-like structure 76 to the prosthetic material 74. These means include bonding; capturing the scaffold-like structure 76 between two layers of prosthetic material 74; and incorporating the scaffold-like structure 76 directly into the prosthetic material 74. The scaffold-like structure 76 can be present either inside the prosthesis body 72, or outside the prosthesis body 72, or within the prosthesis body 72, or combinations thereof. Desirably, the surface of the prosthesis 70 that is exposed to flow of blood or body fluids is relatively smooth to minimize turbulence.

The prosthesis body 72 can carry radiopaque markers to help fluoroscopically position the prosthesis. The markers can take the form, e.g. of marker bands, tight wound coils, or wire made from radiopaque materials such as platinum, platinum/iridium, or gold.

FIGS. 20A and 20B show the prosthesis 70 installed within a targeted hollow body organ (FIG. 20A) or about a targeted hollow body organ (FIG. 20B). At least part of the outer surface(s) of prosthesis can be coated with substances, such as glue or drugs, or structures, such as barbs or hooks, to promote adhesion or connection to the hollow body organ.

The structural strength of the prosthesis 70 resists distension of the tissue wall en masse beyond the maximum size and shaped imposed by the prosthesis body 72. In this way, the prosthesis body 72 dictates a maximum size and shape for the body organ. However, the prosthesis body 72 does not interfere with the contraction of the hollow body organ to a lesser size and shape.

Desirably, as FIGS. 20A and 20B show, the prosthesis body 72 accommodates the introduction of one or more fasteners 56 to anchor the prosthesis 70 in place. For this purpose, regions of the prosthesis body 72 can be specially sized and configured for the receipt and retention of fasteners. For example, the size and spacing of the scaffold-like structure 76 can be configured in the regions to specially accommodate the placement of fasteners 56; and/or woven fibers with an "X-pattern" or a "sinusoidal pattern" can be used in the region to specially accommodate placement of fasteners 56; and/or the prosthetic material can be folded-over to form multiple layers, to reinforce the prosthesis in the regions where fasteners 56 are placed; and/or denser weave patterns or stronger fibers can be used, selected from, e.g., Kevlar™ material or Vectran™ material or metallic wire woven alone or interwoven with typical polyester fibers in the regions were fasteners 56 are placed. It may also be desirable to fluoroscopically indicate the regions with auxiliary radiopaque markers on the prosthetic material 14, and/or scaffold-like structure 76 to aid in positioning the fasteners 56.

The fasteners 56 can be variously constructed. They can, e.g., comprise staples or (as shown) helical fasteners, like that shown in FIG. 4A, but without the tether element 18.

The prosthesis 70 as just described can be installed in various parts of the body and for various therapeutic purposes. Two embodiments will be described for the purpose of illustration. The first embodiment is directed to implantation within a heart chamber for treatment and/or repair of congestive heart failure. The second embodiment is directed to implantation in a heart valve annulus for heart valve remodeling.

B. Systems and Methods for Supporting Tissue in a Heart Chamber

Figure 21:
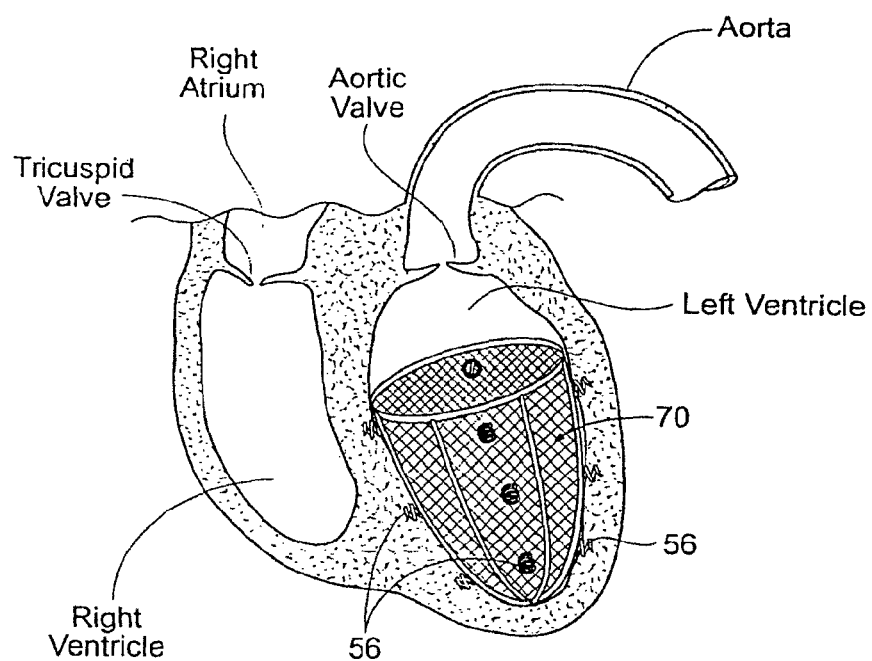
FIG. 21 shows a prosthesis of a type shown in FIGS. 19A to 19F installed in the interior of a heart chamber.

FIG. 21 shows the prosthesis 70 as described installed in a left ventricle of a heart. The left ventricle has been enlarged due to the effects of congestive heart failure. As FIG. 21 shows, the prosthesis is desirably secured to the walls of the ventricle using fasteners 56.

The presence of the prosthesis 70 shapes the left ventricle in a desired fashion, pulling the chamber walls laterally closer together and thereby reducing the overall maximum internal volume. The presence of the prosthesis 70 resists further enlargement of the left ventricle during ventricular diastole and provides a shape is better suited to efficient ventricular pumping. However, the presence of the prosthesis 70 does not interfere with contraction of the left ventricle during ventricular systole.

In this embodiment, it is desired that the prosthesis 70 is not inherently electrically conductive, so as not to interfere with electrical conduction within the heart.

FIGS. 22A to 22D show the intra-vascular deployment of the prosthesis 70 shown in FIG. 21. Alternatively, the prosthesis 70 can be installed using conventional open heart surgical techniques or by thoracoscopic surgery techniques.

Figure 22A:
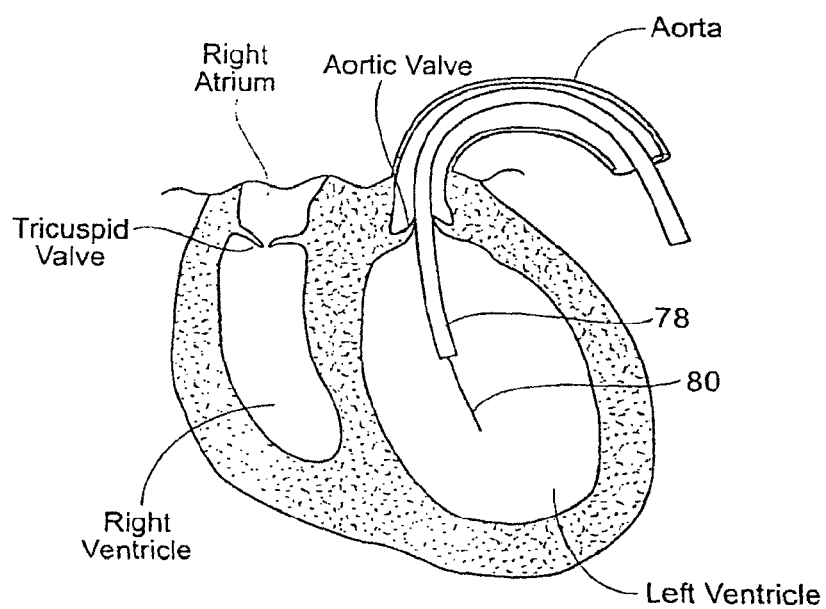
FIGS. 22A to 22D show the steps in establishing, by use of intra-vascular tools and techniques, the prosthesis shown in FIG. 20A.
Figure 22B:
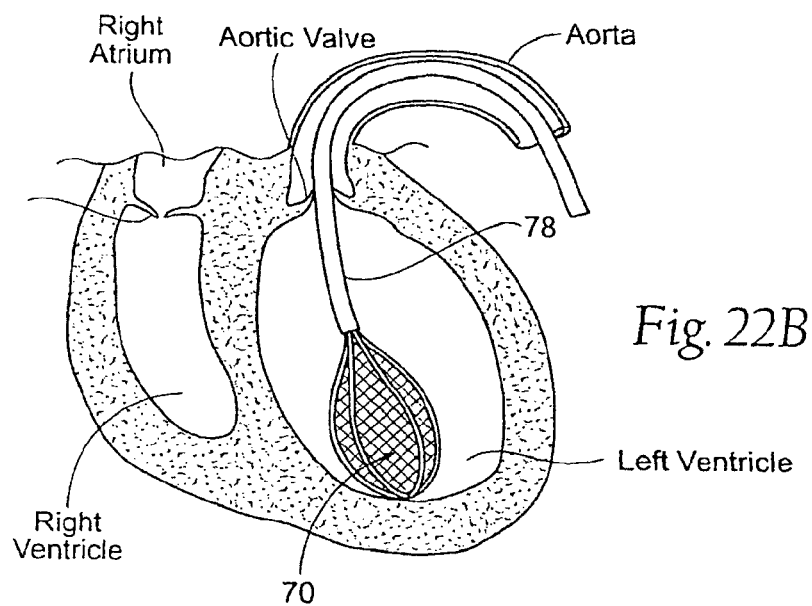

In the intra-vascular approach shown in FIGS. 22A to 22D, a first catheter 78 is navigated over a guide wire 80 through the aortic valve into the left ventricle (see FIG. 22A). The first catheter 78 can be delivered through the vasculature under fluoroscopic guidance, e.g., through either a retrograde arterial route (via, e.g., the femoral artery or subclavian artery) (as shown) or an antegrade venous then trans-septal route.

The first catheter 78 carries the prosthesis 70 in a radially reduced or collapsed configuration. Once inside the left ventricle (see FIG. 22B), the first catheter 70 releases the prosthesis 70, which eventually expands radially into, the configuration shown in FIG. 21. The first catheter 78 is then withdrawn over the guide wire 80.

Figure 22C:
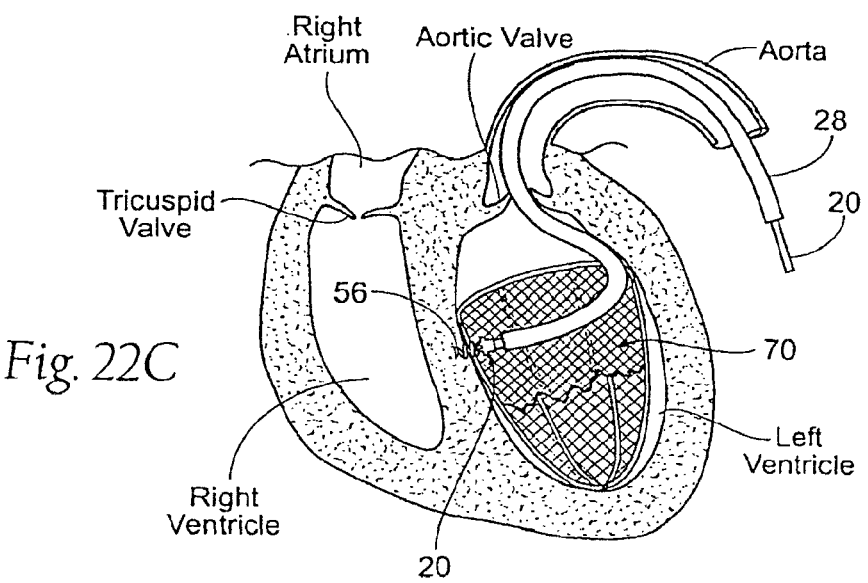

The guide component 28 (previously described) is delivered over the guide wire 80 (which is then withdrawn) (see FIG. 22C) and maneuvered to each region where a fastener 56 is to be applied. The applier instrument 20 (previously described) is introduced through the guide component 28, as FIG. 22C shows and can also been seen in FIG. 4B. In this embodiment, the applier instrument 20 carries a helical fastener 56 generally of the type shown in FIG. 4A, but without a tether element 18. The applier instrument 20 rotates the fastener 56, causing it to penetrate the myocardium.

Figure 22D:
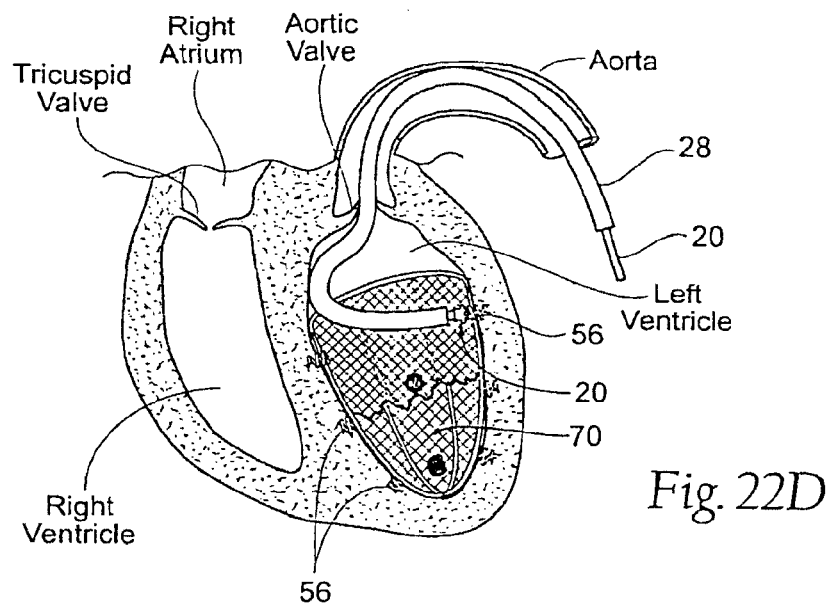

As FIG. 22D depicts, the guide component 28 is repositioned in succession to each intended attachment site for the fastener 56. At each site, the applier instrument 20 is actuated to place a fastener 56. FIGS. 22C and 22D show the guide component 28 braced against a wall of the ventricle to apply a counterbalancing resolution force to the implantation force. In this way, a desired pattern of fasteners 56 is applied, securing the prosthesis 70 to the left ventricle, as FIG. 21 shows. The applier instrument 20 and guide component 28 are then withdrawn.

The prosthesis 70 has been installed to shape the left ventricle to treat, in this instance, congestive heart failure.

In an alternative embodiment, the prosthesis 70 could be sized and configured to contain a fluid, e.g., saline or blood. For example, the prosthesis 70 can carry fluid receiving tubes or pockets. The delivery of fluid causes the tubes or pockets to expand, thereby enlarging the occupying volume of the prosthesis 70. As a result, the usable internal volume of the heart chamber is reduced.

Figure 23:
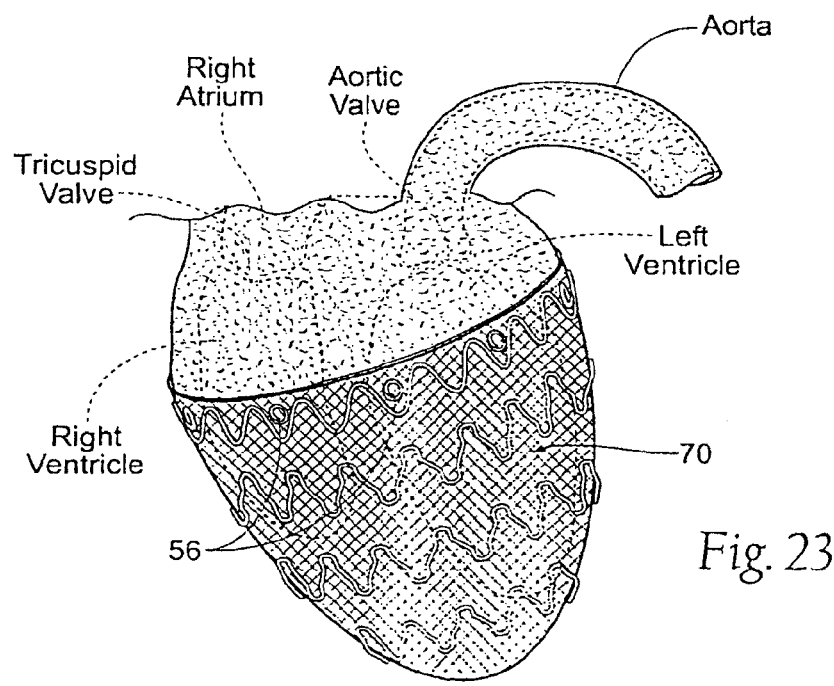
FIG. 23 shows a prosthesis of a type shown in FIGS. 19A to 19F installed about the exterior of a heart.

FIG. 23 shows an alternative embodiment, in which the prosthesis 70 as described is installed around the exterior of the ventricles of a heart afflicted with congestive heart failure. The prosthesis 70 can be installed using conventional open heart surgical techniques or by thoracoscopic surgery techniques.

As shown in FIG. 23, the prosthesis 70 is desirably secured to the exterior walls of the ventricles using fasteners 56. The fasteners 56 are applied from within the heart, using the intra-vascular approach and technique just described. The presence of the prosthesis 70 shapes the ventricles, reducing their overall maximum internal volume. The presence of the prosthesis 70 also resists further enlargement of the ventricles and provides a shape is better suited to efficient ventricular pumping. The presence of the prosthesis 70, however, desirably does not interfere with contraction of the ventricles to a lesser volume.

Figure 24A:
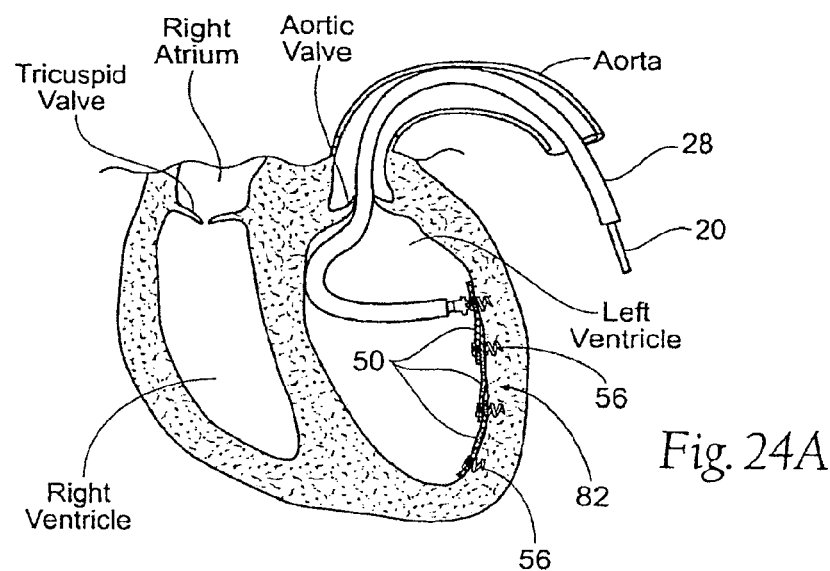
FIGS. 24A and 24B show a composite prosthesis having the features of the prosthesis shown in FIGS. 19A to 19F, being formed by an array of two or more patch components installed in a left ventricle of a heart.
Figure 24B:
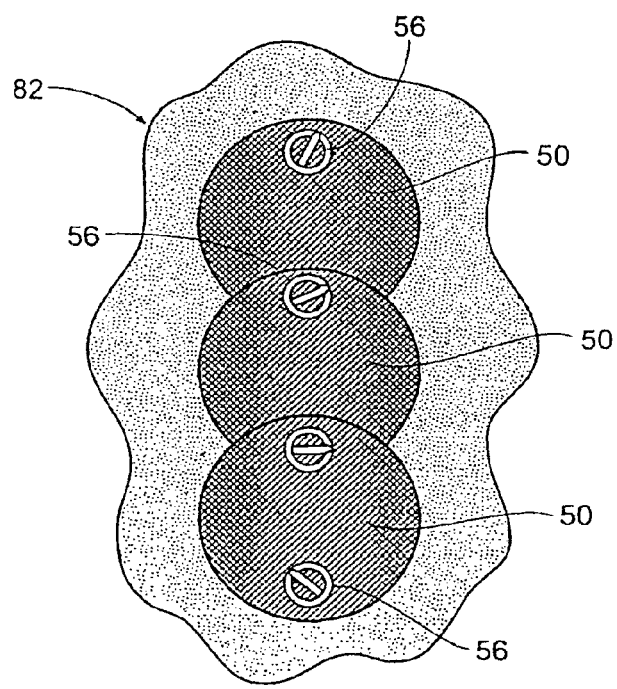

FIGS. 24A and 24B show a prosthesis system 82 comprising an array of two or more patch components 50, as previously described with reference to FIG. 15A. In FIGS. 24A and 24B, the hollow body organ comprises a left ventricle of a heart, but it should be appreciated that the system 82 can be established in other body organs, as well. In this embodiment, each patch component 50 is individually attached by one or more fasteners 56 to a localized tissue region in the hollow body organ. The patch components 50 are shown to be placed in an overlapping array (see FIG. 24B), but the array need not be overlapping. FIG. 24A shows the guide component 28 braced against a wall of the ventricle to apply a counterbalancing resolution force to the implantation force. Using a plurality of patch components 50, the system 82 can form a composite prosthesis within the entire interior of the hollow body organ, or, alternatively, the system 82 can form a prosthesis that occupies only a portion of the entire interior to provide localized tissue shaping. While not shown, it should also be appreciated that the system 82 of patch components 50 can be installed on the exterior of the hollow body organ.

The system 82 comprising an array of discrete patch components 50 can shape all or a portion of the ventricles, resisting further enlargement of the ventricles and provides a shape is better suited to efficient ventricular pumping. The presence of the patch components 50, however, desirably does not interfere with contraction of the ventricles to a lesser volume.

The prostheses 70 and prosthesis system 82 shown and described in foregoing FIGS. 19 to 24 can be used alone or in combination with the tissue folding systems shown and described in FIGS. 10 to 15, as well as in combination with the tissue support systems described and shown in FIGS. 5 to 10. Furthermore, an implant 10 and/or 40, previously described, can be implanted in association with an individual patch component 50, with the patch component 50 in this arrangement serving to protect underlying tissue from abrasion and providing compliance between the implant 10/40 and tissue. Also, fasteners 56 used to secure a given prosthesis to any tissue wall (e.g., as shown in FIG. 21 or 23) can be applied in association with an individual patch component 50, with the patch component 50 in this arrangement serving to protect the prosthesis 70 from abrasion due to the fastener 56, as well as providing compliance between the fastener 56 and the prosthesis 70.

C. Systems and Methods for Support Tissue at or Near a Heart Valve Annulus

Figure 25:
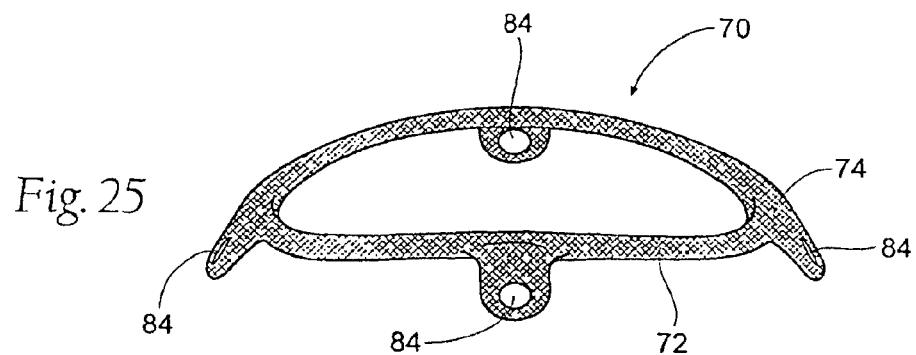
FIG. 25 shows a prosthesis having the features of the prosthesis shown in FIGS. 19A to 19F, being formed in the form of a ring for placement in or near a heart valve annulus.

FIG. 25 shows a prosthesis 70, in which the prosthesis body 72 is sized and configured as a ring, for placement in a heart valve annulus. The prosthesis body can be in the form of a continuous ring or a discontinuous ring. In this way, the prosthesis body 72 is preformed in a desired size and shape to emulate the shape of a healthy, native annulus. The prosthesis body thereby serves to shape an annulus that has experienced dilation, as well as resist future dilation. The prosthesis body 72 desirably shapes the annulus so that so that normal leaflet coaptation will occur, and/or so that retrograde flow through the valve is prevented or reduced.

In this embodiment, the body 72 includes prosthetic material 74 that promotes tissue ingrowth, to aid in fixing the prosthesis 70 to tissue in or near the annulus. In this embodiment, it is desired that the material of the prosthesis body 72 is not inherently electrically conductive, so as not to interfere with electrical conduction within the heart.

As before described, the prosthesis body 72 in this embodiment is also desirable sized and configured to permit its non-invasive deployment by an intra-vascular catheter. Alternatively, however, the prosthesis body 72 can be installed using conventional open heart surgical techniques or by thoracoscopic surgery techniques.

In this arrangement, the prosthesis body 72 desirably includes eyelet regions 84 to receive fasteners 56, so that the prosthesis 70 can be secured to tissue in or near the targeted heart valve annulus.

Figure 26A:
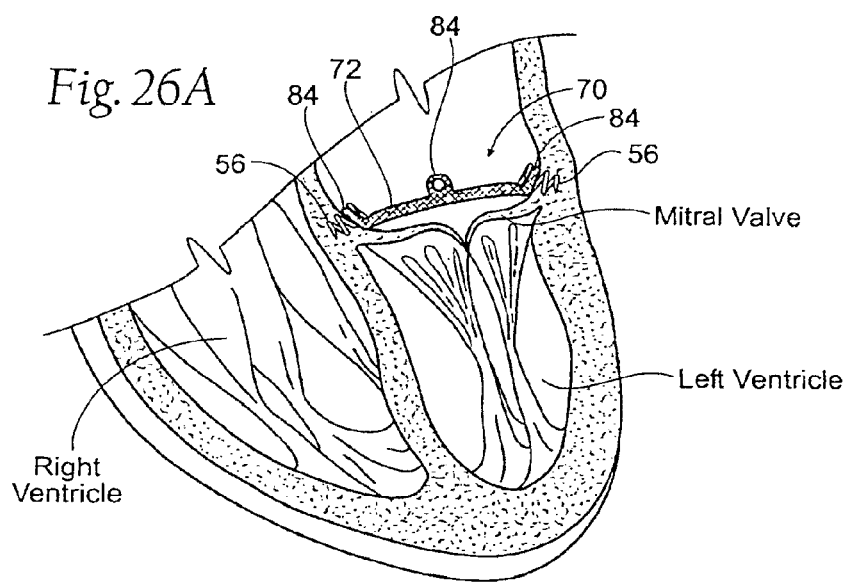
FIG. 26A shows a prosthesis as shown in FIG. 25 installed in or near an annulus of an aortic valve.
Figure 26B:
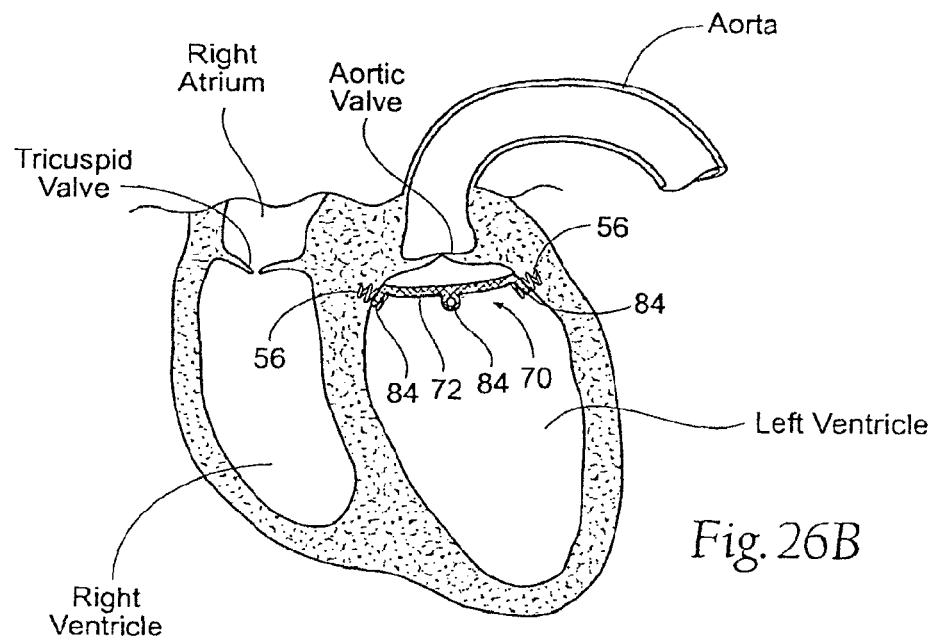
FIG. 26B shows a prosthesis as shown in FIG. 25 installed in or near an annulus of a mitral valve.

FIG. 26A shows for purposes of illustration the prosthesis 70 installed in or near the annulus of a mitral valve. FIG. 26B shows for the purpose of illustration the prosthesis 70 installed in or near the annulus of an aortic valve. The prosthesis 70 may be attached either inside the ventricle in or near the aortic valve (as FIG. 26B shows) or outside the ventricle within the aorta in or near the aortic valve.

Figure 27:
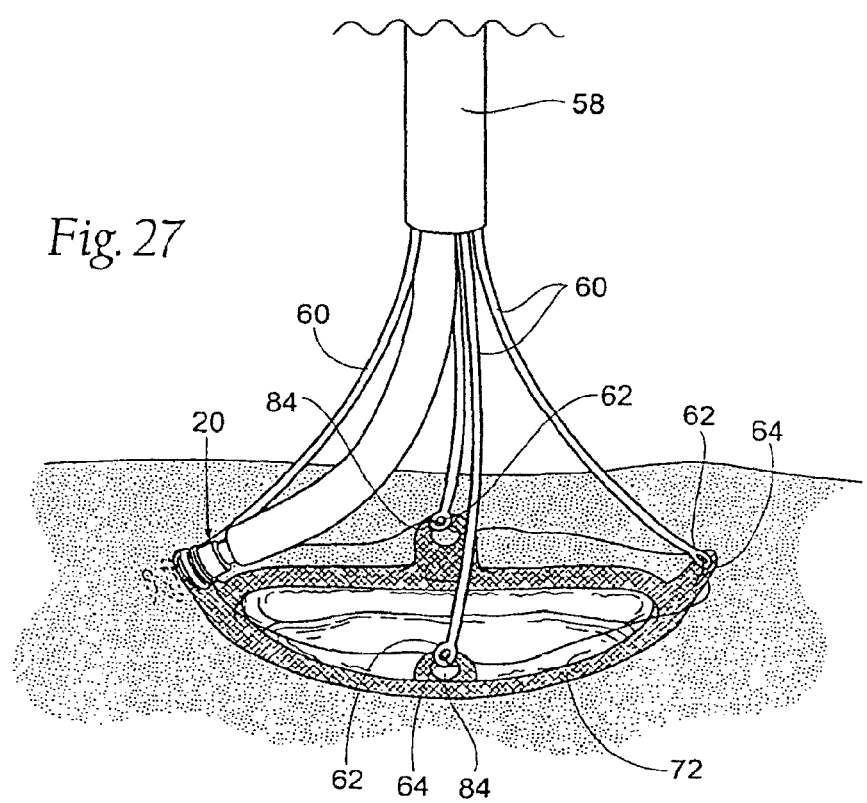
FIG. 27 is a catheter that deploys the prosthesis shown in FIG. 25 by intra-vascular access.

As FIG. 27 shows, the prosthesis body 72 can be delivered through intra-vascular access by a catheter 58 like that shown in FIG. 15B. The catheter 58 carries the prosthesis body 72 in a collapsed condition. Once positioned in the targeted heart annulus, the prosthesis body 72 can be released from the end of catheter 58 on guide elements 60. The guide elements 60 comprise wires with eyes 62, which are releasably secured to the eyelet regions 84 of the prosthesis body 72 by releasable sutures 64, as previously described. Once the prosthesis body is deployed and positioned, the prosthesis body can be attached to the annulus using the fasteners 56, and the sutures 64 then released to free the prosthesis body 72 from the catheter 58. As FIG. 15B shows, the applier instrument 20, previously described, may be deployed over the guide elements 60, or the applier instrument 20 may be deployed independent of the guide elements (as FIG. 27 shows) to apply the fasteners 56 to the eyelet regions.

The prosthesis 70 shown and described in foregoing FIGS. 25 to 27 can be used alone or in combination with the tissue support systems described and shown in FIGS. 8 and 9.

Figure 32:
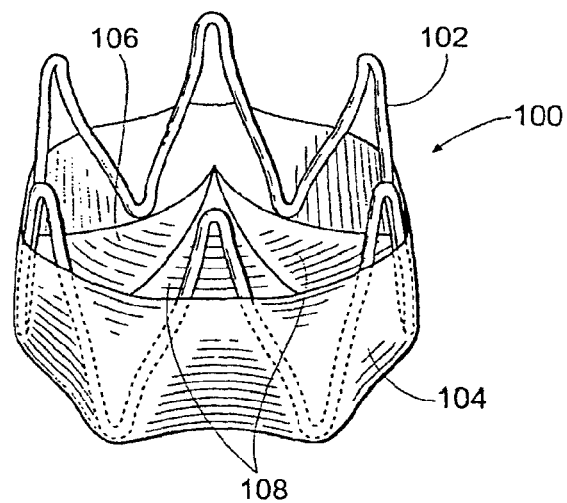
FIG. 32 shows a heart valve assembly having many of the features of the prosthesis shown in FIGS. 19A to 19F, being formed for placement in or near a heart valve annulus.

FIG. 32 shows a heart valve assembly 100 having a generally cylindrical shape formed by a collapsible scaffold-like structure 102. As shown, the scaffold-like structure 102 carries a prosthetic material 104, although the structure 102 can be free of a prosthetic material 104. As previously described with respect to the prosthesis 70, the prosthetic material 104 and/or scaffold-like structure 102 of the heart valve assembly 100 are sized and configured to assume a compressed or collapsed, low profile condition, to permit their intra-vascular introduction into a hollow body organ by a catheter. Also as previously discussed, the prosthetic material 104 and/or scaffold-like structure 102 are sized and configured for expansion, and preferably self-expansion, in situ from a collapsed condition into an expanded condition in contact with tissue in the targeted region. For example, the scaffold-like structure 102 can comprise a self-expanding plastic or metal material (e.g., from Nitinol® wire) that can be compressed in the presence of a force, but self-expands upon removal of the compressive force. As illustrated, the scaffold-like structure 102 comprises zigzag type stent rings.

The valve assembly 100 includes a flexible valve member 106. In the illustrated embodiment, the valve member comprises three, coapting leaflets 108, although the number of leaflets 108 can vary, e.g., between two and four.

Figure 33:
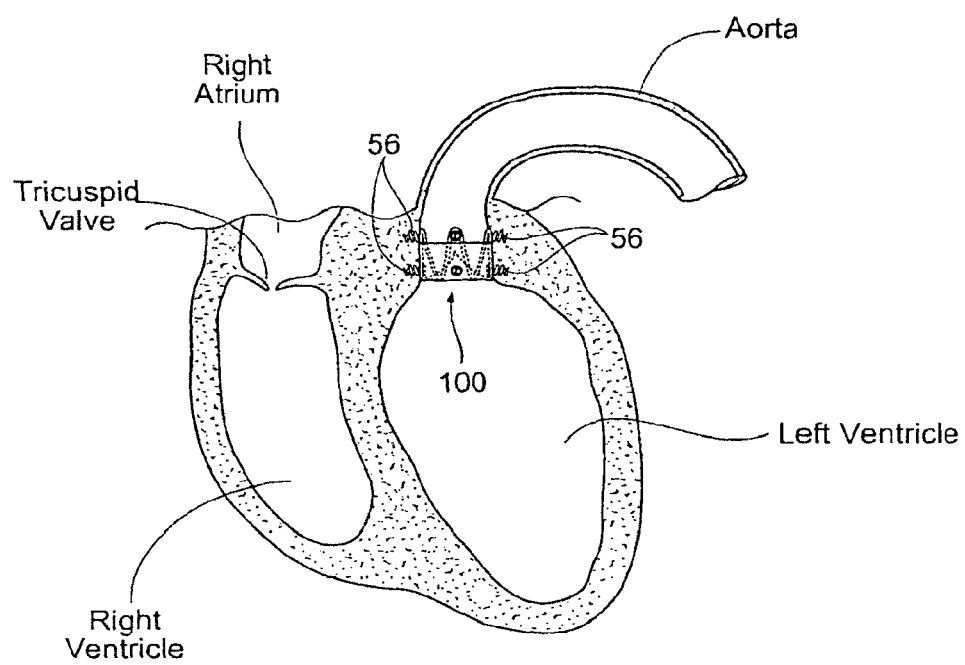
FIG. 33 shows an assembly as shown in FIG. 32 installed in or near an annulus of an aortic valve.

In use (see FIG. 33), the valve assembly 100 is installed at or near a heart valve annulus. In FIG. 33, the targeted heart valve annulus is the aortic valve. Desirably, as FIG. 33 shows, the valve assembly 100 accommodates the introduction of one or more fasteners 56 to anchor the assembly 100 in place either during or after its installation.

As previously described with respect to the prosthesis 70, regions of the scaffold-like structure 102 and/or prosthetic material 104 can be specially sized and configured for the receipt and retention of fasteners 56. The fasteners 56 can be variously constructed. They can, e.g., comprise staples or (as shown) helical fasteners, like that shown in FIG. 4A, but without the tether element 18.

The valve assembly 100 as just described can be installed in the region of a heart valve annulus by intra-vascular approach. However, it should be appreciated that the assembly 100 can be installed using an open surgical procedure.

Figure 34A:
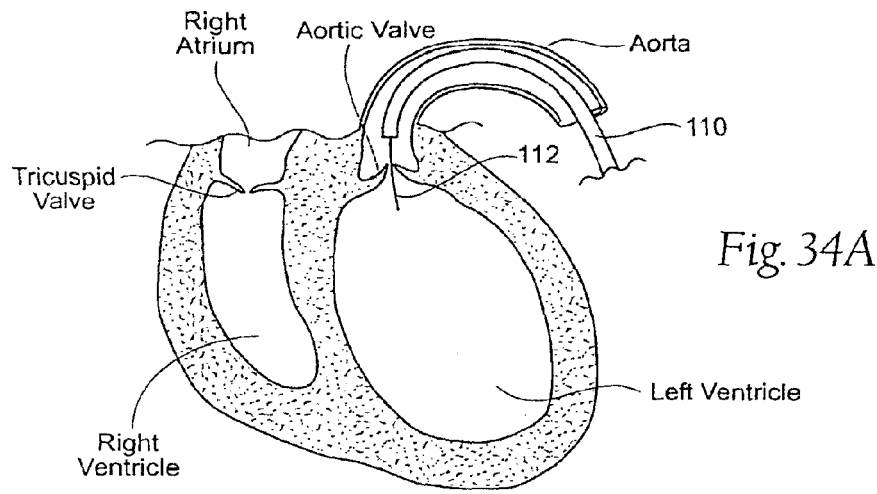
FIGS. 34A to 34C show the steps in installing, by use of intra-vascular tools and techniques, the heart valve assembly shown in FIG. 32 in or near an annulus of an aortic valve.

Using an intra-vascular approach (see FIG. 34A), the assembly 100 may be deployed by first folding and/or compressing the assembly 100 into a lumen of a trans-vascular catheter 110 for delivery. The catheter 110 may be advanced through the vasculature into the heart through a retrograde arterial route (via, e.g., the femoral artery or subclavian artery) (as FIG. 34A shows) or an antegrade venous and then trans-septal route, if left heart access is needed from a peripheral vessel access. Use of a standard available guide wire 112 and/or guide sheath can assist the operator in delivering and deploying the catheter 110 into position.

Figure 34B:
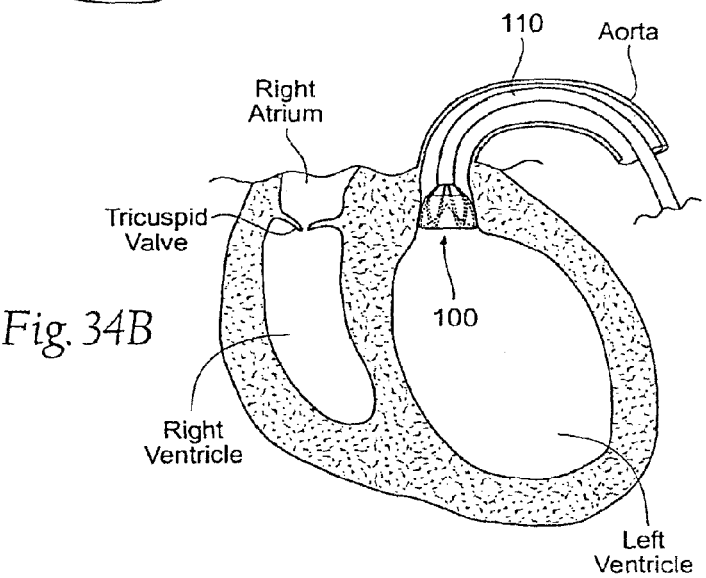
Figure 34C:
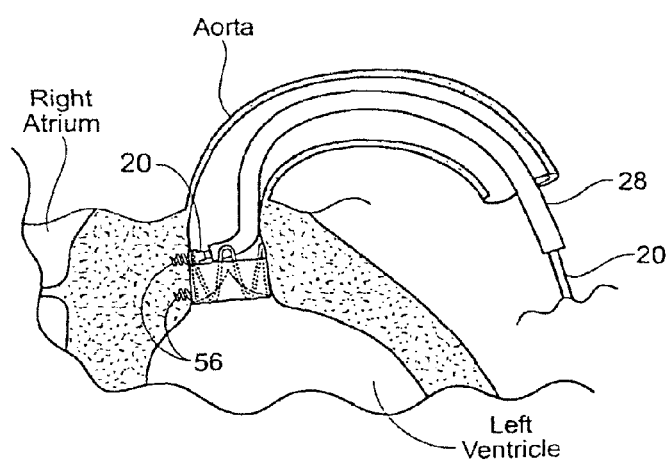

The valve assembly 100 is then be pushed out of the lumen of the catheter 110 (as FIG. 34B shows). The assembly 100 self-expands into the desired shape and tension when released in situ (as FIG. 34C shows). After either partial or complete expansion of the valve assembly 100, the catheter 110 is withdrawn, and the guide component 28 (previously described) is delivered over the guide wire 112. The guide component 28 is maneuvered to each region where a fastener 56 is to be applied. The applier instrument 20 (previously described) is introduced through the guide component 28, as FIG. 34C shows.

The applier instrument 20 carries a helical fastener 56. The applier instrument 20 rotates the fastener 56, causing it to penetrate the myocardium. FIG. 34C shows the guide component 28 braced against a wall of the aorta to apply a counterbalancing resolution force to the implantation force. The guide component 28 is repositioned in succession to each intended attachment site for the fastener 56. At each site, the applier instrument 20 is actuated to place a fastener 56. In this way, a desired pattern of fasteners 56 is applied, securing the valve assembly 100 at or near the targeted heart valve annulus. The applier instrument 20 and guide component 28 are then withdrawn.

The valve assembly 100 has been installed to repair, or replace, or supplement a native heart valve.

The valve assembly 100 shown and described in foregoing FIGS. 32 to 34 can be used alone or in combination with the tissue support systems described and shown in FIGS. 8 and 9.

IV. Implants for Internally Supporting Tissue in a Hollow Body Organ

Figures 30A, 30B:
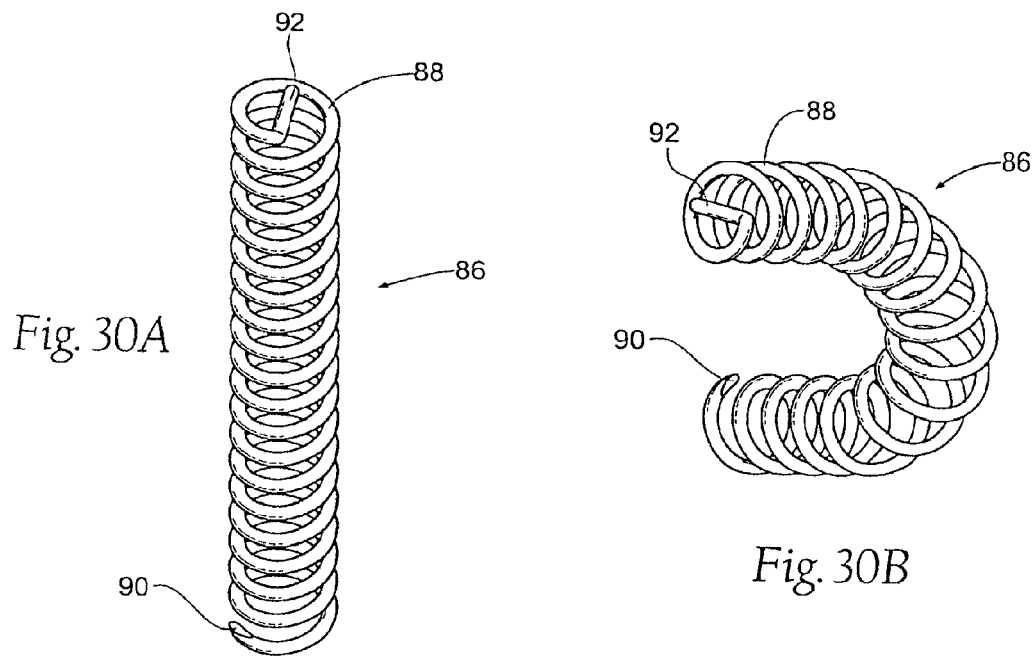
FIGS. 30A and 30B show various embodiments of an elongated implant that can be implanted in a hollow body organ to shape the organ and prevent its enlargement, FIG. 30A showing an implant having a generally linear shape, and FIG. 30B showing an implant having a generally curvilinear shape.

FIGS. 30A and 30B show an implant 86 sized and configured for placement in a hollow body organ. The implant 86 includes an elongated body 88 that can be made from a formed plastic or metal or ceramic material suited for implantation in the body.

The body 88 can possess a generally straight or linear configuration, as FIG. 30A shows. Alternatively, the body 88 can possess a curvilinear configuration, as FIG. 30B shows. As shown in FIGS. 30A and 30B, the body 88 possesses a helical coil configuration.

The body 88 includes a distal region 90. The distal region 90 is sized and configured to penetrate tissue.

The body 88 also includes a proximal region 92. As shown in FIGS. 30A and 30B, the proximal region 92 comprises an L-shaped leg. Like the L-shaped leg 16 shown in FIG. 4A, the L-shape leg 92 shown in FIGS. 30A and 30B desirably bisects the entire interior diameter of the coil body 88. As before described, the L-shaped leg 92 serves as a stop to prevent the coil body 88, when rotated, from penetrating too far into tissue. Furthermore, the rotatable implant drive mechanism 22 on the applier instrument 20 (shown in FIG. 4B) is sized and configured to engage the L-shaped leg 92 and impart rotation to the coil body 88 to achieve implantation in tissue.

Figure 31:
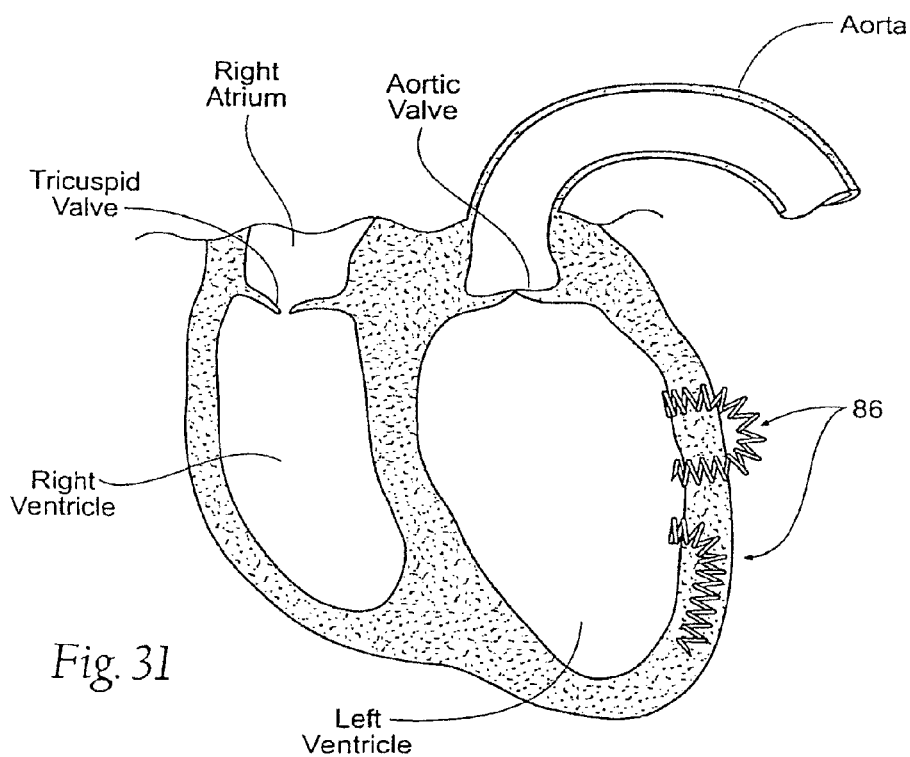
FIG. 31 shows the elongated implant shown in FIGS. 30A and 30B implanted in a left ventricle of a heart.

The body 88 and its distal region 90 are sized and configured to be implanted within or partially within tissue in a hollow body organ. The linear body 88 shown in FIG. 30A can run either longitudinally or circumferentially within tissue, as FIG. 31 shows. The curvilinear body 88 shown in FIG. 30B exits tissue and then re-enters tissue in a serpentine path, as FIG. 31 also shows. When implanted, the implants 86 resist enlargement of the interior of a hollow body organ. However, the implants 86 desirably do not interfere with contraction of the hollow body organ to a lesser interior volume.

FIG. 31 shows the implants 86 implanted, for the purpose of illustration, in a left ventricle of a heart. The presence of the implants 86 prevents enlargement of the heart chamber due to, e.g., congestive heart failure. Of course, the implants 86 can be implanted in other hollow body organs and achieve a comparable therapeutic effect.

Like the implants 10 previously described, the implants 86 shown in FIGS. 30A and 30B can be installed by intra-vascular deployment using the instruments and techniques previously described. Alternatively, the implants 86 can be installed using conventional open heart surgical techniques or by thoracoscopic surgery techniques.

In the many catheter-based implantation techniques described above, the catheter used to place a given prosthesis in contact with tissue is usually manipulated to be detached from the prosthesis prior to the placement of fasteners. If desired, the catheter and prosthesis can remain coupled together during the fastening procedure. In this way, control of the prosthesis can be maintained up to and during the fastening procedure.

Other embodiments and uses of the invention will be apparent to those skilled in the art from consideration of the specification and practice of the invention disclosed herein. The specification and examples should be considered exemplary and merely descriptive of key technical; features and principles, and are not meant to be limiting. The true scope and spirit of the invention are defined by the following claims. As will be easily understood by those of ordinary skill in the art, variations and modifications of each of the disclosed embodiments can be easily made within the scope of this invention as defined by the following claims.

What is claimed is:

1. A method to reduce the volume or modify the shape of the heart, the method comprising:
   providing at least one implant, wherein the implant comprises a helical fastener;
   introducing a guide component from a remote access site into the interior of the heart, wherein the guide component has a deflectable distal tip;
   advancing an applier instrument through the guide component, wherein the guide component and/or the applier instrument is configured to possess sufficient column strength to resolve at least a portion of an implantation force, and wherein the implantation force comprises a force necessary to cause the helical fastener to penetrate heart tissue;
   bracing a distal portion of the guide component against an interior wall of the heart to apply a resolution force to counteract the implantation force; and
   rotating the helical fastener into the heart tissue with the applier instrument to anchor the implant to the heart tissue.

2. The method according to claim 1, wherein the implant is configured to engage the applier instrument and the applier instrument is configured to apply the implantation force to cause the helical fastener to penetrate the heart tissue.

3. The method according to claim 2, wherein the implant comprises a tether element.

4. The method according to claim 3, further comprising anchoring at least two implants, wherein each of the at least two implants comprises a tether element.

5. The method according to claim 4, further comprising:
   providing a clip;
   coupling the tether elements together with the clip; and
   applying a tensioning force to the tethering elements, wherein the clip maintains tension of the tethering elements.

6. The method according to claim 1, wherein the guide component is manipulated to provide at least one deflected curve in the distal tip.

7. The method according to claim 1,
   wherein the interior wall is a first interior wall of the heart,
   wherein the heart tissue forms a portion of a second interior wall of the heart, and
   wherein the first interior wall is substantially opposite the second interior wall.

* * * * *